(12) United States Patent
Geissler et al.

(10) Patent No.: US 10,548,952 B2
(45) Date of Patent: *Feb. 4, 2020

(54) INJECTABLE SOLUTION AT PH7 COMPRISING AT LEAST ONE BASAL INSULIN THE PI OF WHICH IS FROM 5.8 TO 8.5, A PRANDIAL INSULIN AND/OR A GASTROINTESTINAL HORMONE, AND A CO-POLYAMINO ACID BEARING CARBOXYLATE CHARGES AND HYDROPHOBIC RADICALS

(71) Applicant: ADOCIA, Lyons (FR)

(72) Inventors: Alexandre Geissler, Lyons (FR); Ségolène Laage, Lyons (FR); Richard Charvet, Rillieux la Pape (FR); Olivier Soula, Meyzieu (FR)

(73) Assignee: ADOCIA, Lyons (FR)

( * ) Notice: Subject to any disclaimer, the term of this patent is extended or adjusted under 35 U.S.C. 154(b) by 19 days.

This patent is subject to a terminal disclaimer.

(21) Appl. No.: 15/616,470

(22) Filed: Jun. 7, 2017

(65) Prior Publication Data

US 2017/0348396 A1    Dec. 7, 2017

(30) Foreign Application Priority Data

Jun. 7, 2016 (FR) .................................... 16 55222

(51) Int. Cl.
| | | |
|---|---|---|
| *A61K 38/28* | (2006.01) | |
| *A61K 47/56* | (2017.01) | |
| *A61K 9/00* | (2006.01) | |
| *A61K 9/08* | (2006.01) | |
| *A61K 38/26* | (2006.01) | |
| *A61K 47/34* | (2017.01) | |

(52) U.S. Cl.
CPC ............ *A61K 38/28* (2013.01); *A61K 9/0019* (2013.01); *A61K 9/08* (2013.01); *A61K 38/26* (2013.01); *A61K 47/34* (2013.01); *A61K 47/56* (2017.08)

(58) Field of Classification Search
CPC ........ A61K 47/34; A61K 9/08; A61K 9/0019; A61K 47/36; A61K 38/28
See application file for complete search history.

(56) References Cited

U.S. PATENT DOCUMENTS

| | | |
|---|---|---|
| 4,826,818 A | 5/1989 | Mori et al. |
| 5,656,722 A | 8/1997 | Dorschug |
| 6,100,376 A | 8/2000 | Dorschug |
| 2006/0099264 A1 | 5/2006 | Chan et al. |
| 2013/0065826 A1* | 3/2013 | Soula ..................... A61K 38/28 514/6.2 |
| 2013/0178415 A1 | 7/2013 | Soula |

FOREIGN PATENT DOCUMENTS

| | | |
|---|---|---|
| FR | 2 801 226 A1 | 5/2001 |
| FR | 2 840 614 A1 | 12/2003 |
| FR | 2 985 429 A1 | 7/2013 |
| WO | 01/37809 A1 | 5/2001 |
| WO | 03/053339 A2 | 7/2003 |
| WO | 2004/096854 A2 | 11/2004 |
| WO | 2013/021143 A1 | 2/2013 |
| WO | 2013/104861 A1 | 7/2013 |
| WO | 2014/124993 A1 | 8/2014 |
| WO | 2014/124994 A1 | 8/2014 |

OTHER PUBLICATIONS

Timothy J. Deming, "Facile Synthesis of Block Copolypeptides of Defined Architecture", Nature, (1997) vol. 390, pp. 386-389.
Hua Lu et al., "N-Trimethylsilyl Amines for Controlled Ring-Opening Polymerization of Amino Acid N-Carboxyanhydrides and Facile End Group Functionalization of Polypeptides" J. Am. Chemical Society, vol. 130, No. 38, (2008) pp. 12562-12563.
Hua Lu et al., "Hexamethyldisilazane-Mediated Controlled Polymerization of α-Amino Acid N-Carboxyanhydrides" J. Am. Chemical Society, vol. 129, No. 46, (2007) pp. 14114-14115.
Timothy J. Deming, "Polypeptide and Polypeptide Hybrid Copolymer Synthesis via NCA Polymerization" Advance Polymerization Science (2006) vol. 202, pp. 1-18.
The U.S. Appl. No. 15/616,128, filed Jun. 7, 2017 in the name of Alexandre Geissler et al.
Sep. 27, 2018 Office Action issued in U.S. Appl. No. 15/616,128.
Joshi, et al., "The degradation pathways of glucagon in acidic solutions," International Journal of Pharmaceutics, 203, 2000, pp. 115-125.
Jan. 31, 2017 Search Report issued in French Patent Application No. FR1655222.
Aug. 9, 2017 International Search Report filed in Patent Application No. PCT/EP2017/063886.
Aug. 9, 2017 International Search Report filed in Patent Application No. PCT/EP2017/063865.

* cited by examiner

*Primary Examiner* — Sudhakar Katakam
(74) *Attorney, Agent, or Firm* — Oliff PLC

(57) ABSTRACT

A physically stable compositions in the form of an injectable aqueous solution, the pH of which is from 6.0 to 8.0: a basal insulin of which the isoelectric point (pI) is from 5.8 to 8.5, a prandial insulin or a gastrointestinal hormone, and a co-polyamino acid bearing carboxylate charges and at least one hydrophobic radical.

36 Claims, 4 Drawing Sheets

Figure 1:
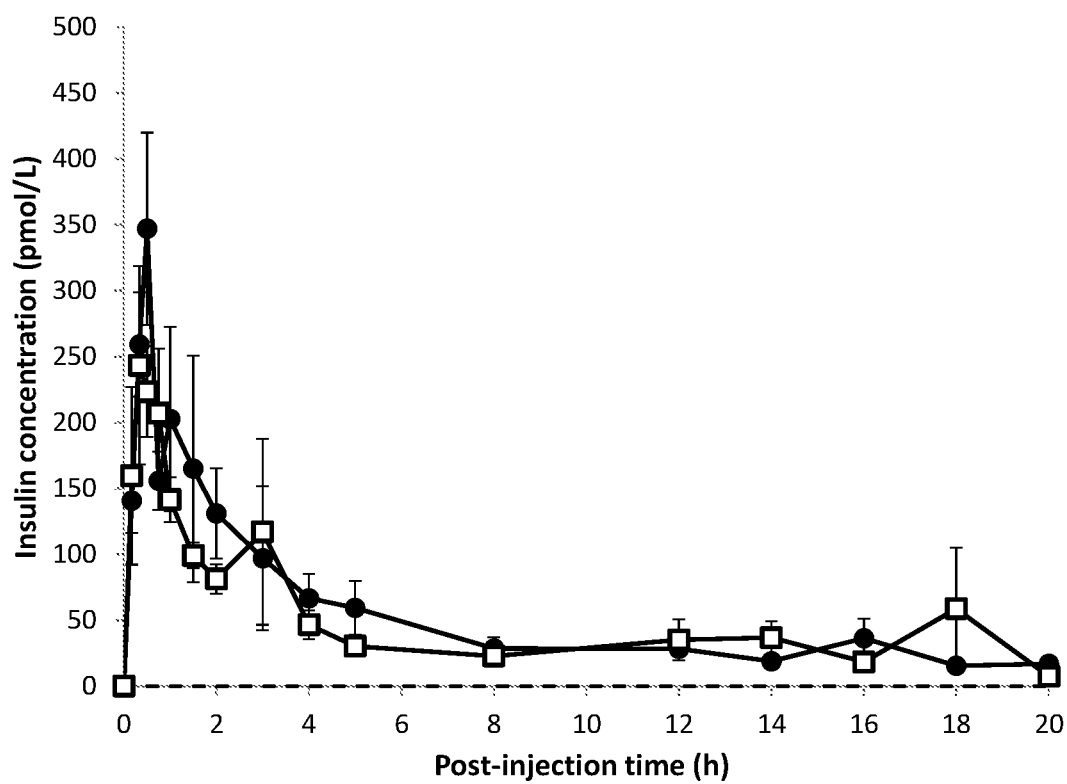

INJECTABLE SOLUTION AT PH7 COMPRISING AT LEAST ONE BASAL INSULIN THE PI OF WHICH IS FROM 5.8 TO 8.5, A PRANDIAL INSULIN AND/OR A GASTROINTESTINAL HORMONE, AND A CO-POLYAMINO ACID BEARING CARBOXYLATE CHARGES AND HYDROPHOBIC RADICALS

The invention relates to the therapies by injection of insulin(s) for treating diabetes.

The invention relates to physically stable compositions in the form of an injectable aqueous solution, the pH of which is from 6.0 to 8.0, comprising at least one basal insulin of which the isoelectric point (pI) is from 5.8 to 8.5, in combination with a prandial insulin, or a gastrointestinal insulin hormone, or a prandial insulin and a gastrointestinal hormone, and a co-polyamino acid bearing carboxylate charges and hydrophobic radicals.

Insulin therapy, or the therapy for diabetes by injection of insulin, has undergone remarkable progress in recent years, in particular thanks to the development of novel insulins which offer a better correction of the glycemia of patients in comparison to human insulin, and which make it possible to better simulate the physiological activity of the pancreas.

When type II diabetes is diagnosed in a patient, a gradual treatment is instituted. First, the patient takes oral antidiabetic drugs (OAD) such as metformin. When the OAD alone are no longer sufficient for regulating the glucose level in the blood, a change in treatment must be made, and, depending on the specificities of the patients, different combinations of treatments can be instituted. For example, the patient can have a treatment based on a basal insulin of the insulin glargine or insulin detemir type in addition to the OAD, and then, depending on the development of the pathology, a treatment based on basal insulin and on prandial insulin.

Moreover, today, in order to ensure the transition of the treatments with OAD to a basal insulin/prandial insulin treatment when the former treatments are no longer able to control the blood glucose level, the injection of analogs of GLP-1 RA is recommended.

The GLP-1 RA, standing for glucagon-like peptide-1 receptor agonists, are insulinotropic peptides or incretins and belong to the family of the gastrointestinal hormones (or gut hormones) which stimulate the secretion of insulin when the glycemia is too high, for example, after a meal.

The gastrointestinal hormones (gut hormones) are also referred to as satiety hormones. They comprise, in particular, GLP-1 RA (glucagon-like peptide-1 receptor agonist) and GIP (glucose-dependent insulinotropic peptide), oxyntomodulin (a derivative of proglucagon), peptide YY, amylin, cholecystokinin, pancreatic polypeptide (PP), ghrelin and enterostatin which have peptide or protein structures. They also stimulate the secretion of insulin, in response to glucose and fatty acids, and, as such, they are potential candidates for the treatment of diabetes.

Among said gastrointestinal hormones, GLP-1 RA are those that, to date, have contributed the best results in the development of drugs. They have made it possible for patients suffering from type II diabetes to lose weight while at the same time having a better control of their glycemia.

Analogs or derivatives of GLP-1 RA have also been developed, in particular in order to improve their stability.

Moreover, a diabetic patient, to cover his/her daily insulin needs, currently has available, in a simplified manner, two types of insulins having complementary actions: the prandial insulins (or so-called rapid-acting insulins) and the basal insulins (or so-called short-acting insulins).

The prandial insulins allow a rapid management (metabolization and/or storage) of the glucose ingested in meals and snacks. The patient must self-administer an injection of a prandial insulin before each ingestion of food, namely approximately 2 to 3 injections per day. The prandial insulins used the most are: human recombinant insulin, Novolog® (insulin aspart from NOVO NORDISK), Humalog® (insulin lispro from ELI LILLY) and Apidra® (insulin glulisine from SANOFI).

The basal insulins ensure the maintenance of the glycemic homeostasis of the patient outside periods of food intake. They act essentially by blocking the endogenous glucose production (hepatic glucose). The daily dose of basal insulin generally corresponds to 40-50% of the total daily insulin needs. Depending on the basal insulin used, this dose is administered in 1 or 2 injections distributed regularly over the course of the day. The basal insulins used the most are Levemir® (insulin detemir from NOVO NORDISK) and Lantus® (insulin glargine from SANOFI).

For the sake of completeness it should be noted that NPH (insulin NPH standing for neutral protamine Hagedorn insulin; Humuline NPH®, Insulatard®) is the oldest basal insulin. This formulation is the result of a precipitation of human insulin (anionic at neutral pH) by a cationic protein, the protamine. The microcrystals thus formed are dispersed in an aqueous suspension and dissolve slowly after subcutaneous injection. This slow dissolution ensures a prolonged release of the insulin. However, this release does not ensure a constant insulin concentration over time. The release profile is bell-shaped and lasts only from 12 to 16 hours. Therefore, said insulin is injected twice daily. This basal insulin NPH here is much less effective than the modern basal insulins, Levemir® and Lantus®. NPH is an intermediate-acting basal insulin.

The principle of NPH has evolved with the appearance of the rapid insulin analogs giving rise to so-called "premix" products that offer rapid action and intermediate action simultaneously. NovoLog Mix® (NOVO NORDISK) and Humalog Mix® (ELI LILLY) are formulations comprising a rapid insulin analog, Novolog® and Humalog®, complexed partially by the protamine. These formulations thus contain microcrystals of insulin analog, the action of which is referred to as intermediate, and, a portion of insulin that has remained soluble, the action of which is rapid. These formulations indeed offer the advantage of a rapid insulin, but they also have the defect of NPH, that is to say a duration of action limited to from 12 to 16 hours and a "bell" shaped insulin release profile. However, these products make it possible for the patient to self-administer a single injection of an intermediate-acting basal insulin together with a rapid-acting prandial insulin. However, many patients want to reduce their number of injections.

The currently marketed basal insulins can be classified based on the technical solution that makes it possible to obtain the prolonged action, and, to date, two approaches are used.

The first approach, that of insulin detemir, is in vivo binding to albumin. This involves an analog, soluble at pH 7, which comprises a side chain of fatty acid (tetradecanoyl) bound at position B29 which, in vivo, allows this insulin to combine with albumin. Its prolonged action is primarily due to this affinity for albumin after subcutaneous injection.

However, its pharmacokinetic profile cannot cover a day, and as a result it is usually used in two injections daily.

Another insulin which is soluble at pH 7 is insulin degludec marketed under the name of Tresiba®$^d$. It also comprises a side chain of fatty acid bound to the insulin (hexadecandioyl-γ-L-Glu).

The second approach, that of insulin glargine, is the precipitation at physiological pH. Insulin glargine is an analog of human insulin obtained by elongation of the C-terminal portion of the B chain of human insulin by two arginine residues and by substitution of the asparagine residue A21 with a glycine residue (U.S. Pat. No. 5,656, 722). The addition of two arginine residues was intended to adjust the pI (isoelectric point) of insulin glargine at physiological pH, and, in this manner, to make this analog of human insulin insoluble in a physiological medium.

In addition, the substitution of A21 was intended to make the insulin glargine stable at acidic pH and to be able to formulate it in the form of a solution which is an injectable solution at acidic pH. During the subcutaneous injection, the passage of insulin glargine from an acidic pH (pH 4-4.5) to a physiological pH (neutral pH) causes its precipitation under the skin. The slow redissolution of the insulin glargine microparticles ensures a slow and prolonged action.

The hypoglycemic effect of insulin glargine is nearly constant for a duration of 24 hours, which allows most of the patients to limit themselves to a single injection daily.

Insulin glargine is considered today to be the basal insulin used the most.

However, the necessarily acidic pH of the formulations of basal insulins, the isoelectric point of which is from 5.8 to 8.5, of the insulin glargine type can be a real disadvantage, since this acidic pH of the formulation of insulin glargine sometimes causes pain to the patients during the injection and especially it stops any formulation with other proteins, particularly with the prandial insulins, since the latter are not stable at acidic pH. The impossibility of formulating a prandial insulin at acidic pH is due to the fact that, under these conditions, a prandial insulin undergoes a secondary reaction of deamidation in position A21, which does not allow it to meet the stability requirements applicable to injectable drugs.

To date, in the applications WO 2013/021143 A1, WO 2013/104861 A1, WO 2014/124994 A1 and WO 2014/124993 A1, it was demonstrated that it was possible to solubilize these basal insulins of the insulin glargine type, the isoelectric point of which is from 5.8 to 8.5, at neutral pH, while at the same time maintaining a solubility differential between the in-vitro medium (which contains it) and the in-vivo medium (under the skin) independently of the pH.

In particular, the application WO 2013/104861 A1 describes compositions in the form of an injectable aqueous solution, the pH of which is from 6.0 to 8.0, comprising at least (a) a basal insulin, the isoelectric point pI of which is from 5.8 to 8.5, and (b) a co-polyamino acid which bears carboxylate charges and which is substituted with hydrophobic radicals.

These compositions of the prior art have the main disadvantage that they are not sufficiently stable to meet the specifications applicable to the pharmaceutical formulations.

In the examples of the experimental part of the present patent application, it is demonstrated that the compositions described, in particular, in WO 2013/104861 A1 present an unsatisfactory stability over time.

Therefore, there is a need to find a solution which makes it possible to dissolve a basal insulin of which the isoelectric point (pI) is from 5.8 to 8.5, while preserving the basal profile thereof after injection, but which also makes it possible to meet the standard physical stability conditions for the pharmaceutical products based on insulin.

Surprisingly, the applicant has found that the co-polyamino acids bearing carboxylate charges and hydrophobic radicals according to the invention make it possible to obtain compositions in the form of solutions which not only meet the requirements described in WO 2013/104861 A1, but which, in addition, are capable of conferring an improved physical stability to said composition without the need to increase the quantity of excipients used.

These performances never reached a priori are, in addition, maintained when the basal insulin of which the isoelectric point is from 5.8 to 8.5, is combined in the composition with a prandial insulin and/or a gastrointestinal hormone.

Thus, surprisingly, the affinity of the co-polyamino acids according to the invention for insulin glargine has been increased, in that it makes it possible to obtain a solubilization and a stabilization of the solutions of insulin glargine at a [Hy]/[basal insulin] ratio below that of the prior art; in addition, these results are obtained without alteration, and even with an improvement, of the propensity of insulin glargine to precipitate, as is demonstrated in the experimental part.

This improvement of the affinity moreover makes it possible to limit the level of exposure to said excipients in the context of chronic treatments.

The co-polyamino acids bearing carboxylate charges and hydrophobic radicals Hy according to the invention present an excellent resistance to hydrolysis. This can be shown, in particular, under accelerated conditions, for example, by hydrolysis tests at alkaline pH (pH 12).

In addition, forced oxidation tests, for example, of the Fenton oxidation type, show that the co-polyamino acids bearing carboxylate charges and hydrophobic radicals Hy present a good resistance to oxidation.

The invention thus relates to physically stable compositions in the form of an injectable aqueous solution, the pH of which is from 6.0 to 8.0, comprising at least:

a) one basal insulin, the isoelectric point (pI) of which is from 5.8 to 8.5, and b) a prandial insulin and/or a gastrointestinal hormone, and c) a co-polyamino acid bearing carboxylate charges and at least one hydrophobic radical of formula I.

In an embodiment, the invention relates to a composition in the form of an injectable aqueous solution, the pH of which is from 6.0 to 8.0, comprising at least:

a) one basal insulin, the isoelectric point (pI) of which is from 5.8 to 8.5, and b) a prandial insulin, and c) a co-polyamino acid bearing carboxylate charges and at least one hydrophobic radical of formula I.

In an embodiment, the invention relates to a composition in the form of an injectable aqueous solution, the pH of which is from 6.0 to 8.0, comprising at least:

a) one basal insulin, the isoelectric point (pI) of which is from 5.8 to 8.5, and b) a gastrointestinal hormone, and c) a co-polyamino acid bearing carboxylate charges and at least one hydrophobic radical of formula I.

In an embodiment, the invention relates to a composition in the form of an injectable aqueous solution, the pH of which is from 6.0 to 8.0, comprising at least:

a) one basal insulin, the isoelectric point (pI) of which is from 5.8 to 8.5, and b) a prandial insulin and a gastrointestinal hormone, and
c) a co-polyamino acid bearing carboxylate charges and at least one hydrophobic radical of formula I.

In an embodiment, said co-polyamino acid bearing carboxylate charges and hydrophobic radicals Hy consists of glutamic or aspartic units, and said hydrophobic radicals Hy are radicals of the following formula I:

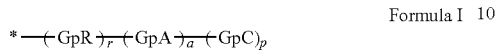

Formula I in which
GpR is a radical: of formula II or II':

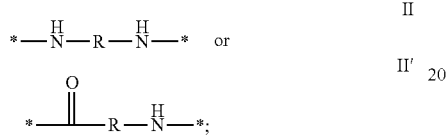

GpA is a radical: of formula III or III':

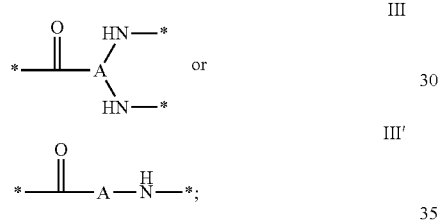

GpC is a radical of formula IV:

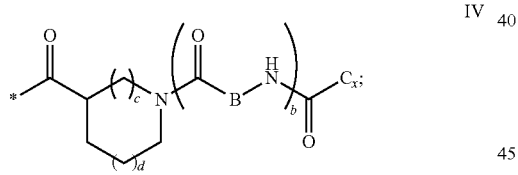

IV

Hy comprises more than 30 carbon atoms,
the * indicate the sites of attachment of the different groups bound by amide functions;
  a is a whole number equal to 0 or 1;
  b is a whole number equal to 0 or 1;
  p is a whole number equal to 1 or 2, and
    if p is equal to 1, then a is equal to 0 or 1 and GpA is a radical of formula III', and
    if p is equal to 2, then a is equal to 1 and GpA is a radical of formula III;
  c is a whole number equal to 0 or 1, and, if c is equal to 0, then d is equal to 1 or 2;
  d is a whole number equal to 0, to 1 or 2;
  r is a whole number equal to 0 or 1, and
    if r is equal to 0, then the hydrophobic radical of formula I is bound to the polyamino acid via a covalent bond between a carbonyl of the hydrophobic radical and a nitrogen atom in N-terminal position of the co-polyamino acid, thus forming an amide function originating from the reaction of an amine function in N-terminal position of the precursor of the co-polyamino acid and an acid function borne by the precursor of the hydrophobic radical, and
    if r is equal to 1, then the hydrophobic radical of formula I is bound to the co-polyamino acid:
      a via a covalent bond between a nitrogen atom of the hydrophobic radical and a carbonyl of the co-polyamino acid, thus forming an amide function originating from the reaction of an amine function of the precursor of the hydrophobic radical and an acid function borne by the precursor of the co-polyamino acid, or
      a via a covalent bond between a carbonyl of the hydrophobic radical and a nitrogen atom in N-terminal position of the co-polyamino acid, thus forming an amide function originating from the reaction of an acid function of the precursor of the hydrophobic radical and an amine function in N-terminal position borne by the precursor of the co-polyamino acid;
  R is a radical selected from the group consisting of:
    a linear or branched divalent alkyl radical comprising, if GpR is a radical of formula II, from 2 to 12 carbon atoms, or, if GpR is a radical of formula II', from 1 to 11 carbon atoms;
    a linear or branched divalent alkyl radical comprising, if GpR is a radical of formula II, from 2 to 11 carbon atoms, or, if GpR is a radical of formula II', from 1 to 11 carbon atoms, said alkyl radical bearing one or more —$CONH_2$ functions, and
    an un-substituted ether or polyether radical comprising from 4 to 14 carbon atoms and from 1 to 5 oxygen atoms;
  A is a linear or branched alkyl radical comprising from 1 to 6 carbon atoms;
  B is a linear or branched alkyl radical, optionally comprising an aromatic ring, comprising from 1 to 9 carbon atoms;
  $C_x$ is a linear or branched monovalent alkyl radical, in which x indicates the number of carbon atoms, and:
    if p is equal to 1, x is from 11 to 25 ($11 \leq x \leq 25$);
    if p is equal to 2, x is from 9 to 15 ($9 \leq x \leq 15$),
  the ratio i between the number of hydrophobic radicals and the number of glutamic or aspartic units being between $0 < i \leq 0.5$;
  when several hydrophobic radicals are borne by a co-polyamino acid, then they are identical or different,
  the degree of polymerization DP in glutamic or aspartic units is from 5 to 250;
  the free acid functions being in the form of a salt of an alkaline cation selected from the group consisting of $Na^+$ and $K^+$.

The pH of the compositions according to the invention is from 6.0 to 8.0, preferably from 6.6 to 7.8, or more preferably from 6.8 to 7.6.

Said co-polyamino acid bearing carboxylate charges and hydrophobic radicals Hy is soluble in an aqueous solution at a pH from 6 to 8, at a temperature of 25° C., and at a concentration of less than 60 mg/mL.

"Physically stable composition" is understood to mean compositions that satisfy the criteria of the visual inspection described in the European, American and International Pharmacopoeias, that is to say compositions which are clear and contain no visible particles, but which are also colorless.

"Injectable aqueous solution" is understood to mean solutions of which the solvent is water, which meet the conditions of the EP and US Pharmacopoeias.

"Co-polyamino acid consisting of glutamic or aspartic units" is understood to mean noncyclic linear chains of glutamic acid or aspartic acid units bound to one another by peptide bonds, said chains having a C-terminal part corresponding to the carboxylic acid of one end, and an N-terminal part corresponding to the amine of the other end of the chain.

"Soluble" is understood to mean capable of enabling the preparation of a clear solution which is free of particles at a concentration of less than 60 mg/mL in distilled water at 25° C.

"Alkyl radical" is understood to mean a linear or branched carbon chain which comprises no heteroatom.

The co-polyamino acid is a statistical co-polyamino acid in the chain of the glutamic and/or aspartic units.

In the formulas, the * indicate the sites of attachments of the different elements represented.

In an embodiment, the composition according to the invention is characterized in that Hy comprises more than 30 carbon atoms.

In an embodiment, the composition according to the invention is characterized in that Hy comprises from 30 to 70 carbon atoms.

In an embodiment, when p=1, x is from 11 to 25 (11≤x≤25). In particular, when x is from 15 to 16 (x=15 or 16), then r=1 and R is an ether or polyether radical, and, when x is greater than 17 (x≥17), then r=1 and R is an ether or polyether radical.

In an embodiment, when p=2, x is from 9 to 15 (9≤x≤15).

In an embodiment, the composition according to the invention is characterized in that said hydrophobic radicals are selected from the hydrophobic radicals of formula I in which p=1, represented by the following formula V:

formula V

GpR, GpA, GpC, r and a have the definitions given above.

In an embodiment, the composition according to the invention is characterized in that the hydrophobic radical is a radical of formula V, in which r is equal to 1 (r=1), and a is equal to 0 (a=0).

In an embodiment, the composition according to the invention is characterized in that the hydrophobic radical is a radical of formula V in which r is equal to 1 (r=1) and a is equal to 1 (a 1).

In an embodiment, the composition according to the invention is characterized in that the 5 hydrophobic radical is a radical of formula V in which GpR is a radical of formula II.

In an embodiment, the composition according to the invention is characterized in that the hydrophobic radical is a radical of formula V in which GpR is a radical of formula II, in which R is a divalent linear alkyl radical comprising from 2 to 12 carbon atoms.

In an embodiment, the composition according to the invention is characterized in that the hydrophobic radical is a radical of formula V in which GpR is a radical of formula II in which R is a divalent alkyl radical comprising from 2 to 6 carbon atoms.

In an embodiment, the composition according to the invention is characterized in that the hydrophobic radical is a radical of formula V in which GpR is a radical of formula II in which R is a divalent linear alkyl radical comprising from 2 to 6 carbon atoms.

In an embodiment, the composition according to the invention is characterized in that the hydrophobic radical is a radical of formula V in which GpR is a radical of formula II in which R is a divalent alkyl radical comprising from 2 to 4 carbon atoms.

In an embodiment, the composition according to the invention is characterized in that the hydrophobic radical is a radical of formula V in which GpR is a radical of formula II in which R is a divalent linear alkyl radical comprising from 2 to 4 carbon atoms.

In an embodiment, the composition according to the invention is characterized in that the hydrophobic radical is a radical of formula V in which GpR is a radical of formula II in which R is a divalent alkyl radical comprising 2 carbon atoms.

In an embodiment, the composition according to the invention is characterized in that the hydrophobic radical is a radical of formula V in which GpR is a radical of formula II in which R is a divalent alkyl radical comprising 6 carbon atoms.

In an embodiment, the composition according to the invention is characterized in that the hydrophobic radical is a radical of formula V in which GpR is a radical of formula II'.

In an embodiment, the composition according to the invention is characterized in that the hydrophobic radical is a radical of formula V in which GpR is a radical of formula II' in which R is a divalent linear alkyl radical comprising from 1 to 11 carbon atoms.

In an embodiment, the composition according to the invention is characterized in that the hydrophobic radical is a radical of formula V in which GpR is a radical of formula II' in which R is a divalent alkyl radical comprising from 1 to 6 carbon atoms.

In an embodiment, the composition according to the invention is characterized in that the hydrophobic radical is a radical of formula V in which GpR is a radical of formula II or II', in which R is a divalent alkyl radical comprising from 2 to 5 carbon atoms and bearing one or more amide functions (—CONH$_2$).

In an embodiment, the composition according to the invention is characterized in that the hydrophobic radical is a radical of formula V in which GpR is a radical of formula II' or II, in which R is a divalent linear alkyl radical comprising from 2 to 5 carbon atoms and bearing one or more amide functions (—CONH$_2$).

In an embodiment, the composition according to the invention is characterized in that the hydrophobic radical is a radical of formula V in which GpR is a radical of formula II or II' in which R is a radical selected from the group consisting of the radicals represented by the formulas below:

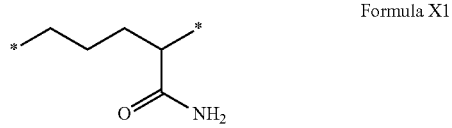

Formula X1

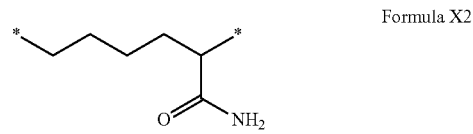

Formula X2

In an embodiment, the composition is characterized in that the hydrophobic radical of formula V in which GpR is a radical of formula II or II' in which R is a radical of formula X1.

In an embodiment, the composition is characterized in that the hydrophobic radical of formula V in which GpR is a radical of formula II or II', in which R is a radical of formula X2.

In an embodiment, the composition according to the invention is characterized in that the radical R is bound to the co-polyamino acid via an amide function borne by the carbon in delta or epsilon position (or in position 4 or 5 with respect to the amide function (—CONH$_2$).

In an embodiment, the composition according to the invention is characterized in that the hydrophobic radical is a radical of formula V in which GpR is a radical of formula II or 11', in which R is an unsubstituted linear ether or polyether radical comprising from 4 to 14 carbon atoms and from 1 to 5 oxygen atoms.

In an embodiment, the composition according to the invention is characterized in that the hydrophobic radical is a radical of formula V in which GpR is a radical of formula II or II', in which R is an ether radical.

In an embodiment, the composition according to the invention is characterized in that the hydrophobic radical is a radical of formula V in which GpR is a radical of formula II or II', in which R is an ether radical comprising from 4 to 6 carbon atoms.

In an embodiment, the composition according to the invention is characterized in that the hydrophobic radical is a radical of formula V in which GpR is a radical of formula II or II' in which R is an ether radical represented by the formula

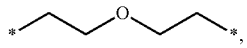

of formula X7.

In an embodiment, the composition according to the invention is characterized in that the hydrophobic radical is a radical of formula V in which GpR is a radical of formula II or II, in which R is a polyether radical.

In an embodiment, the composition according to the invention is characterized in that the hydrophobic radical is a radical of formula V in which GpR is a radical of formula II or II', in which R is a linear polyether radical comprising from 6 to 10 carbon atoms and from 2 to 3 oxygen atoms.

In an embodiment, the composition according to the invention is characterized in that the hydrophobic radical of formula V in which GpR is a radical of formula II or II', in which R is a polyether radical selected from the group consisting of the radicals represented by the formulas below:

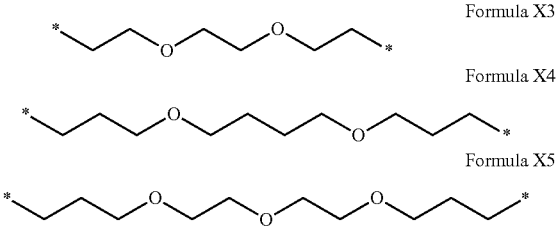

Formula X3

Formula X4

Formula X5

Formula X6

In an embodiment, the composition is characterized in that the hydrophobic radical of formula V in which GpR is a radical of formula II or II', in which R is a radical of formula X3.

In an embodiment, the composition is characterized in that the hydrophobic radical of formula V in which GpR is a radical of formula II or II', in which R is a radical of formula X4.

In an embodiment, the composition is characterized in that the hydrophobic radical of formula V in which GpR is a radical of formula II or II', in which R is a radical of formula X5.

In an embodiment, the composition is characterized in that the hydrophobic radical of formula V in which GpR is a radical of formula II or II', in which R is a radical of formula X6.

In an embodiment, the composition according to the invention is characterized in that the hydrophobic radical of formula V in which GpR is a radical in which R is a polyether radical selected from the group consisting of the radicals represented by the formulas below:

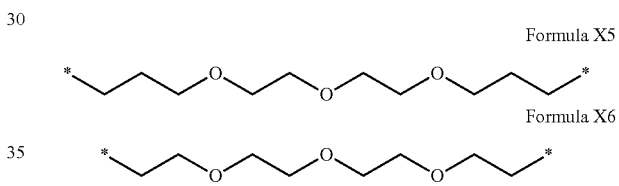

Formula X5

Formula X6

In an embodiment, the composition is characterized in that the hydrophobic radical of formula V in which GpR is a radical of formula II in which R is a polyether radical of formula X5.

In an embodiment, the composition is characterized in that the hydrophobic radical of formula V in which GpR is a radical of formula II in which R is a polyether radical of formula X6.

In an embodiment, the composition according to the invention is characterized in that the hydrophobic radical is a radical of formula V in which a is equal to 0 (a=0) and r is equal to 0 (r 0).

In an embodiment, the composition according to the invention is characterized in that the hydrophobic radical is a radical of formula V in which a is equal to 1 (a=1), and the radical GpA of formula III' is selected from the group consisting of the radicals represented by the formulas below:

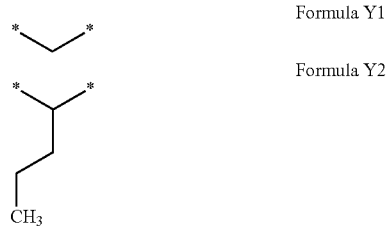

Formula Y1

Formula Y2

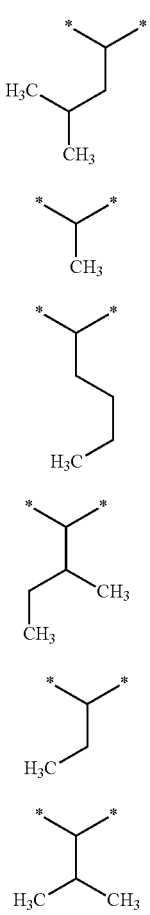

Formula Y3

Formula Y4

Formula Y5

Formula Y6

Formula Y7

Formula Y8

In an embodiment, the composition is characterized in that the hydrophobic radical is a radical of formula V in which a is equal to 1 (a=1), and the radical GpA of formula III' is a radical of formula Y1.

In an embodiment, the composition is characterized in that the hydrophobic radical is a radical of formula V in which a is equal to 1 (a=1), and the radical GpA of formula III' is a radical of formula Y2.

In an embodiment, the composition is characterized in that the hydrophobic radical is a radical of formula V in which a is equal to 1 (a=1) and the radical GpA of formula III' is a radical of formula Y3.

In an embodiment, the composition is characterized in that the hydrophobic radical is a radical of formula V in which a is equal to 1 (a=1) and the radical GpA of formula III' is a radical of formula Y4.

In an embodiment, the composition is characterized in that the hydrophobic radical is a radical of formula V in which a is equal to 1 (a=1) and the radical GpA of formula III' is a radical of formula Y5.

In an embodiment, the composition is characterized in that the hydrophobic radical is a radical of formula V in which a is equal to 1 (a=1) and the radical GpA of formula III' is a radical of formula Y6.

In an embodiment, the composition is characterized in that the hydrophobic radical is a radical of formula V in which a is equal to 1 (a=1) and the radical GpA of formula III' is a radical of formula Y7.

In an embodiment, the composition is characterized in that the hydrophobic radical is a radical of formula V in which a is equal to 1 (a=1) and the radical GpA of formula III' is a radical of formula Y8.

In an embodiment, the composition according to the invention is characterized in that the hydrophobic radical is a radical of formula V in which the radical GpC of formula IV is selected from the group consisting of the radicals of formula IVa, IVb or IVc represented hereafter:

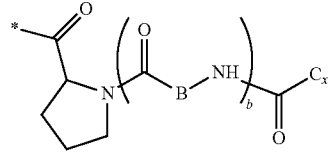

Formula IVa

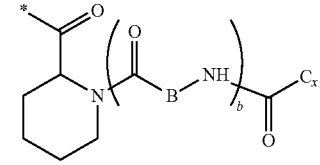

Formula IVb

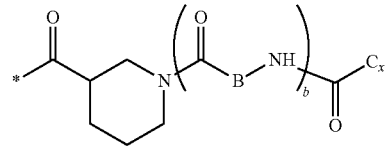

Formula IVc

In an embodiment, the composition according to the invention is characterized in that the hydrophobic radical is a radical of formula V in which the radical GpC is of formula IVa.

In an embodiment, the composition according to the invention is characterized in that the hydrophobic radical is a radical of formula V in which the radical GpC of formula IV is selected from the group consisting of the radicals of formula IVa, IVb or IVc in which b is equal to 0, having formulas IVd, IVe and IVf respectively, represented hereafter

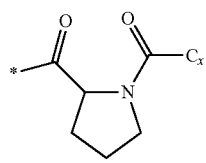

Formula IVd

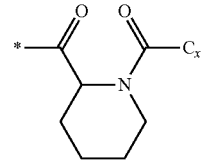

Formula IVe

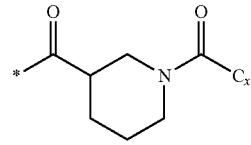

Formula IVf

In an embodiment, the composition according to the invention is characterized in that the hydrophobic radical is a radical of formula V in which the radical GpC corresponds to formula IV or IVa in which b=0, and corresponds to formula IVd.

In an embodiment, the composition according to the invention is characterized in that the hydrophobic radical is a radical of formula V in which the radical GpC of formula IV in which b=1 is selected from the group consisting of the radicals in which B is an amino acid residue selected from the group consisting of the radicals represented by the formulas below:

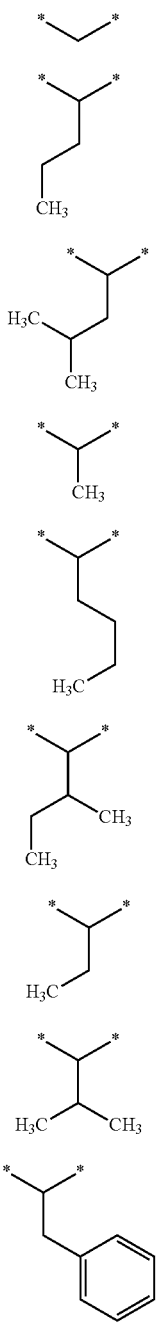

Formula Y1

Formula Y2

Formula Y3

Formula Y4

Formula Y5

Formula Y6

Formula Y7

Formula Y8

Formula Y9

In an embodiment, the composition according to the invention is characterized in that the hydrophobic radical is a radical of formula V in which the radical GpC of formula IV or IVa in which b=1, is selected from the group consisting of the radicals in which B is an amino acid residue selected from the group consisting of the radicals represented by the formulas below:

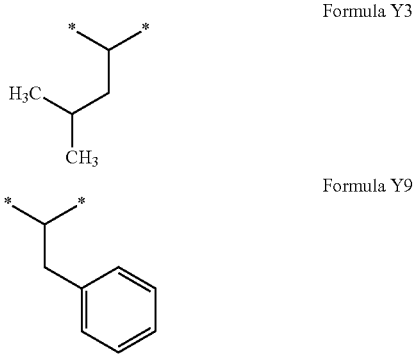

Formula Y3

Formula Y9

In an embodiment, the composition according to the invention is characterized in that the hydrophobic radical is a radical of formula V in which the radical GpC of formula IV is selected from the group consisting of the radicals in which Cx is selected from the group consisting of the linear alkyl radicals.

In an embodiment, the composition according to the invention is characterized in that the hydrophobic radical is a radical of formula V in which the radical GpC of formula IV is selected from the group consisting of radicals in which Cx is selected from the group consisting of the branched alkyl radicals.

In an embodiment, the composition according to the invention is characterized in that the hydrophobic radical is a radical of formula V in which the radical GpC of formula IV is selected from the group consisting of radicals in which Cx is selected from the group consisting of the radicals comprising from 11 to 14 carbon atoms.

In an embodiment, the composition according to the invention is characterized in that the hydrophobic radical is a radical of formula V in which the radical GpC of formula IV is selected from the group consisting of radicals in which Cx is selected from the group consisting of the radicals represented by the formulas below:

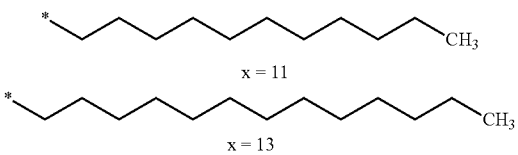

x = 11 x = 13

In an embodiment, the composition according to the invention is characterized in that the hydrophobic radical is a radical of formula V in which the radical GpC of formula IV is selected from the group consisting of the radicals in which Cx is selected from the group consisting of the alkyl radicals comprising from 15 to 16 carbon atoms.

In an embodiment, the composition according to the invention is characterized in that the hydrophobic radical is a radical of formula V in which the radical GpC of formula IV is selected from the group consisting of the radicals in which Cx is selected from the group consisting of the radicals represented by the formulas below:

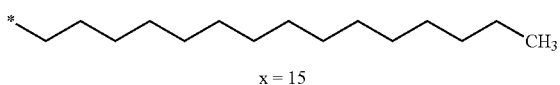

x = 15

In an embodiment, the composition according to the invention is characterized in the hydrophobic radical is a radical of formula V in which the radical GpC of formula IV is selected from the group consisting of the radicals in which Cx is selected from the group consisting of the radicals represented by the formulas below:

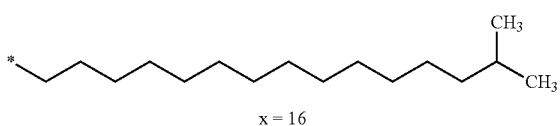

x = 16

In an embodiment, the composition according to the invention is characterized in that the hydrophobic radical is a radical of formula V in which the radical GpC of formula IV is selected from the group consisting of the radicals in which Cx is selected from the group consisting of the alkyl radicals comprising from 17 to 25 carbon atoms.

In an embodiment, the composition according to the invention is characterized in that the hydrophobic radical is a radical of formula V in which the radical GpC of formula IV is selected from the group consisting of the radicals in which Cx is selected from the group consisting of the alkyl radicals comprising from 17 to 18 carbon atoms.

In an embodiment, the composition according to the invention is characterized in that the hydrophobic radical is a radical of formula V in which the radical GpC of formula IV is selected from the group consisting of the radicals in which Cx is selected from the group consisting of the alkyl radicals represented by the formulas below:

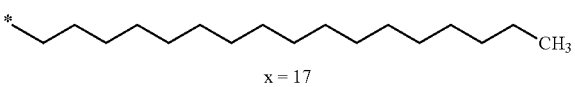

x = 17

In an embodiment, the composition according to the invention is characterized in that the hydrophobic radical is a radical of formula V in which the radical GpC of formula IV is selected from the group consisting of the radicals in which Cx is selected from the group consisting of the alkyl radicals comprising from 19 to 25 carbon atoms.

In an embodiment, the composition according to the invention is characterized in that the hydrophobic radical is a radical of formula V in which the radical GpC of formula IV is selected from the group consisting of the radicals in which Cx is selected from the group consisting of the alkyl radicals represented by the formulas below:

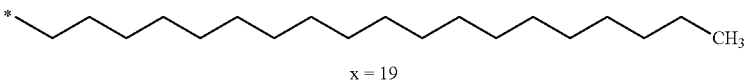

x = 19

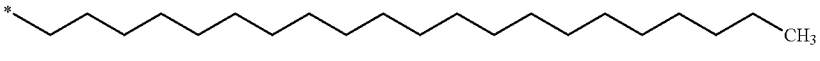

x = 21

In an embodiment, the composition according to the invention is characterized in that the hydrophobic radical is a radical of formula V in which the radical GpC of formula IV is selected from the group consisting of the radicals in which Cx is selected from the group consisting of the alkyl radicals comprising from 18 to 19 carbon atoms In an embodiment, the composition according to the invention is characterized in that said hydrophobic radicals of formula I are selected from the hydrophobic radicals of formula I in which a=1 and p=2, represented by the following formula VI:

Formula VI

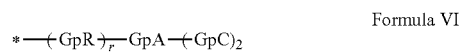

in which
GpR, GpA, GpC, r and a have the definitions given above.

In an embodiment, the composition according to the invention is characterized in that the hydrophobic radical is a radical of formula VI in which GpR is a radical of formula II.

In an embodiment, the composition according to the invention is characterized in that the hydrophobic radical is a radical of formula VI in which GpR is a radical of formula II in which R is a divalent linear alkyl radical comprising from 2 to 12 carbon atoms.

In an embodiment, the composition according to the invention is characterized in that the hydrophobic radical is a radical of formula VI in which GpR is a radical of formula II in which R is a divalent alkyl radical comprising from 2 to 6 carbon atoms.

In an embodiment, the composition according to the invention is characterized in that the hydrophobic radical is a radical of formula VI in which GpR is a radical of formula II in which R is a divalent linear alkyl radical comprising from 2 to 6 carbon atoms.

In an embodiment, the composition according to the invention is characterized in that the hydrophobic radical is a radical of formula VI in which GpR is a radical of formula II in which R is at least one alkyl radical comprising 2 to 4 carbon atoms.

In an embodiment, the composition according to the invention is characterized in that the hydrophobic radical is a radical of formula VI in which GpR is a radical of formula II in which R is a divalent linear alkyl radical comprising from 2 to 4 carbon atoms.

In an embodiment, the composition according to the invention is characterized in that the hydrophobic radical is a radical of formula VI in which GpR is a radical of formula II in which R is a divalent linear alkyl radical comprising 2 carbon atoms.

In an embodiment, the composition according to the invention is characterized in that the hydrophobic radical is a radical of formula VI in which GpR is a radical of formula II'.

In an embodiment, the composition according to the invention is characterized in that the hydrophobic radical is a radical of formula VI in which GpR is a radical of formula II' in which R is a divalent linear alkyl radical comprising from 1 to 11 carbon atoms.

In an embodiment, the composition according to the invention is characterized in that the hydrophobic radical is a radical of formula VI in which GpR is a radical of formula II' in which R is a divalent alkyl radical comprising from 1 to 6 carbon atoms.

In an embodiment, the composition according to the invention is characterized in that the hydrophobic radical is a radical of formula VI in which GpR is a radical of formula II or II', in which R is a divalent alkyl radical comprising from 2 to 5 carbon atoms and bearing one or more amide functions (—CONH2).

In an embodiment, the composition according to the invention is characterized in that the hydrophobic radical is a radical of formula VI in which GpR is a radical of formula II or II', in which R is a divalent linear alkyl radical comprising from 2 to 5 carbon atoms and bearing one or more amide functions (—CONH2).

In an embodiment, the composition according to the invention is characterized in that the hydrophobic radical is a radical of formula VI in which GpR is a radical of formula II or II' in which R is a radical selected from the group consisting of the radicals represented by the formulas below:

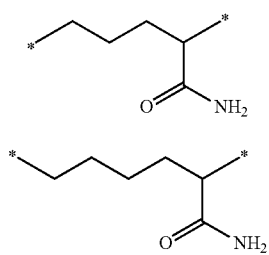

Formula X1

Formula X2

In an embodiment, the composition according to the invention is characterized in that the hydrophobic radical is a radical of formula VI in which the amine function of the GpR radical involved in the formation of the amide function which binds said GpR radical to the co-polyamino acid is borne by a carbon in delta or epsilon position (or in position 4 or 5) with respect to the amide function (—CONH2).

In an embodiment, the composition according to the invention is characterized in that the hydrophobic radical is a radical of formula VI in which GpR is a radical of formula II or II', in which R is an unsubstituted linear ether or polyether radical comprising from 4 to 14 carbon atoms and from 1 to 5 oxygen atoms.

In an embodiment, the composition according to the invention is characterized in that the hydrophobic radical is a radical of formula VI in which GpR is a radical of formula II or II' in which R is an ether radical.

In an embodiment, the composition according to the invention is characterized in that the ether radical R is a radical comprising from 4 to 6 carbon atoms.

In an embodiment, the composition according to the invention is characterized in that the ether radical is

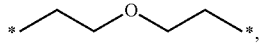

formula X7.

In an embodiment, the composition according to the invention is characterized in that the hydrophobic radical is a radical of formula VI in which GpR is a radical of formula II or IF, in which R is a polyether radical.

In an embodiment, the composition according to the invention is characterized in that the hydrophobic radical is a radical of formula VI in which GpR is a radical of formula II or IF, in which R is a linear polyether radical comprising from 6 to 10 carbon atoms and from 2 to 3 oxygen atoms.

In an embodiment, the composition according to the invention is characterized in that the hydrophobic radical is a radical of formula VI in which GpR is a radical of formula II or II' in which R is a linear polyether radical selected from the group consisting of the radicals represented by the formulas below:

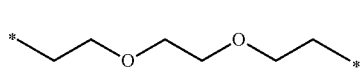

Formula X3

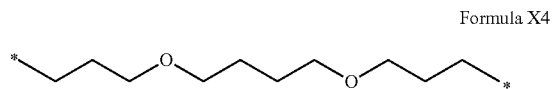

Formula X4

Formula X5

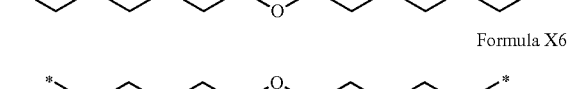

Formula X6

In an embodiment, the composition is characterized in that the hydrophobic radical is a radical of formula VI in which GpR is a radical of formula II or II' in which R is a linear polyether radical of formula X3.

In an embodiment, the composition is characterized in that the hydrophobic radical is a radical of formula VI in which GpR is a radical of formula II or II' in which R is a linear polyether radical of formula X4.

In an embodiment, the composition is characterized in that the hydrophobic radical is a radical of formula VI in which GpR is a radical of formula II or II' in which R is a linear polyether radical of formula X5.

In an embodiment, the composition is characterized in that the hydrophobic radical is a radical of formula VI in which GpR is a radical of formula II or II' in which R is a linear polyether radical of formula X6.

In an embodiment, the composition according to the invention is characterized in that the hydrophobic radical is a radical of formula VI in which the radical GpA of formula III is selected from the group consisting of the radicals of formulas IIIa and IIIb represented hereafter:

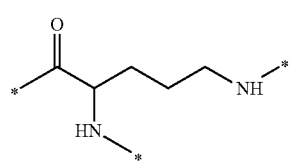

Formula IIIa

-continued

Formula IIIb

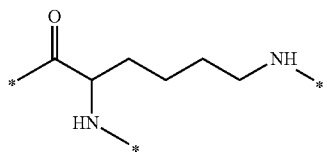

Formula IIIc

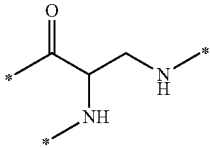

In an embodiment, the composition according to the invention is characterized in that the hydrophobic radical is a radical of formula VI in which the radical GpA of formula III is a radical of formula IIIb represented hereafter Formula IIIb

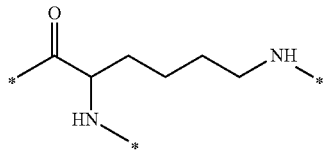

In an embodiment, the composition according to the invention is characterized in that the hydrophobic radical is a radical of formula VI in which the radical GpA of formula III is a radical of formula IIIc.

In an embodiment, the composition according to the invention is characterized in that the hydrophobic radical is a radical of formula VI in which the radical GpC of formula IV is selected from the group consisting of the radicals of formulas IVa, IVb and IVc represented hereafter Formula IVa

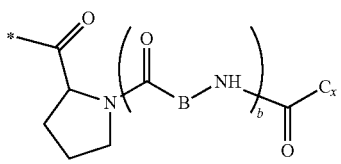

Formula IVb

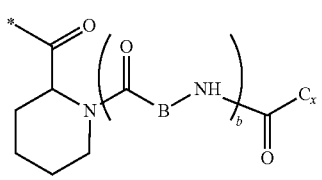

Formula IVc

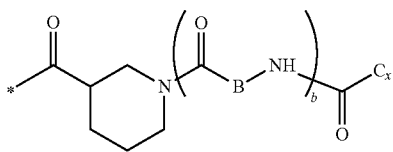

In an embodiment, the composition according to the invention is characterized in that the hydrophobic radical is a radical of formula VI in which the radical GpC is of formula IVa.

In an embodiment, the composition according to the invention is characterized in that the hydrophobic radical is a radical of formula VI in which the radical GpC of formula IV is selected from the group consisting of the radicals of formula IVa, IVb or IVc in which b is equal to 0, corresponding to the formulas IVd, IVe and IVf, respectively, represented hereafter:

Formula IV$_d$

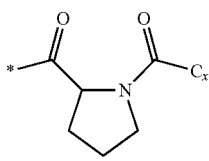

Formula IV$_e$

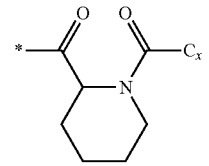

Formula IV$_f$

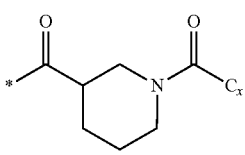

In an embodiment, the composition according to the invention is characterized in that the hydrophobic radical is a radical of formula VI in which the radical GpC corresponds to formula IV or IVa in which b=0, and it corresponds to formula IVd.

In an embodiment, the composition according to the invention is characterized in that the hydrophobic radical is a radical of formula VI in which the radical GpC of formula IV is selected from the group consisting of the radicals in which Cx is selected from the group consisting of the linear alkyl radicals comprising from 9 to 15 carbon atoms.

In an embodiment, the composition according to the invention is characterized in that the hydrophobic radical is a radical of formula VI in which the radical GpC of formula IV is selected from the group consisting of the radicals in which Cx is selected from the group consisting of the branched alkyl radicals comprising from 9 to 15 carbon atoms.

In an embodiment, the composition according to the invention is characterized in that the hydrophobic radical is a radical of formula VI in which the radical GpC of formula IV is selected from the group consisting of the radicals in which Cx is selected from the group consisting of the alkyl radicals comprising 9 or 10 carbon atoms.

In an embodiment, the composition according to the invention is characterized in that the hydrophobic radical is a radical of formula VI in which the radical GpC of formula IV is selected from the group consisting of the radicals in which Cx is selected from the group consisting of the radicals represented by the formulas below:

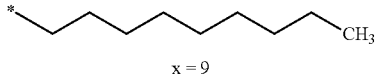

x = 9

In an embodiment, the composition according to the invention is characterized in that the hydrophobic radical is a radical of formula VI in which the radical GpC of formula IV is selected from the group consisting of the radicals in which Cx is selected from the group consisting of the alkyl radicals comprising from 11 to 15 carbon atoms.

In an embodiment, the composition according to the invention is characterized in that the hydrophobic radical is a radical of formula VI in which the radical GpC of formula IV is selected from the group consisting of the radicals in which Cx is selected from the group consisting of the alkyl radicals comprising from 11 to 13 carbon atoms.

In an embodiment, the composition according to the invention is characterized in that the hydrophobic radical is a radical of formula VI in which the radical GpC of formula IV is selected from the group consisting of the radicals in which Cx is selected from the group consisting of the radicals represented by the formulas below:

*~~~~~~~~~~~CH$_3$ x = 11

*~~~~~~~~~~~~~CH$_3$ x = 13

In an embodiment, the composition according to the invention is characterized in that the hydrophobic radical is a radical of formula VI in which the radical GpC of formula IV is selected from the group consisting of the radicals in which Cx is selected from the group consisting of the alkyl radicals comprising 14 or 15 carbon atoms.

In an embodiment, the composition according to the invention is characterized in that the hydrophobic radical is a radical of formula VI in which the radical GpC of formula IV is selected from the group consisting of the radicals in which Cx is selected from the group consisting of the radicals represented by the formulas below:

*~~~~~~~~~~~~~~~CH$_3$ x = 15

In formulas I, V and VI, the * indicate the sites of attachment of the hydrophobic radicals to co-polyamino acid. The radicals Hy are attached to the co-polyamino acid via amide functions.

In formulas II and II', the * indicate, from left to right, respectively, the sites of attachment of GpR:
to the co-polyamino acid and
to GpA if a=1, or to GpC if a=0.

In formulas III and III', the * indicate, from left to right, respectively, the sites of attachment of GpA:
to GpR if r=1, or to the co-polyamino acid if r=0, and
to GpC.

In formula IV, the * indicates the site of attachment of GpC:
to GpA if a=1, GpR if r=1 and a=0, or to the co-polyamino acid if r=0 and a=0.

All the attachments between the different groups GpR, GpA and GpC are amide functions.

The radicals Hy, GpR, GpA, GpC and D are each independently identical or different from one residue to the other.

When the co-polyamino acid comprises one aspartic unit or several aspartic units, it/they can undergo structural rearrangements.

In an embodiment, the composition according to the invention is characterized in that the co-polyamino acid which bears carboxylate charges and hydrophobic radicals is selected from the co-polyamino acids of the following formula VII:

Formula VII in which,

D represents, independently, either a —CH$_2$— group (aspartic unit) or a —CH$_2$—CH$_2$— group (glutamic unit), Hy is a hydrophobic radical selected from the hydrophobic radicals of formula I, V or VI, in which r=1 and GpR is a radical of Formula II, R$_1$ is a hydrophobic radical selected from the hydrophobic radicals of formula I, V or VI in which r=0 or r=1 and GpR is a radical of Formula II', or a radical selected from the group consisting of H, a C2 to C10 linear acyl group, a C4 to C10 branched acyl group, benzyl, a terminal "amino acid" unit and a pyroglutamate, R$_2$ is a hydrophobic radical selected from the hydrophobic radicals of formula I, V or VI in which r=1 and GpR is a radical of Formula II, an —NR'R" radical, R' and R" which are identical or different being selected from the group consisting of H, the C2 to C10 linear or branched or cyclic alkyls, benzyl, and said alkyl R' and R" together optionally forming one or more saturated, unsaturated and/or aromatic carbon rings and/or optionally comprising heteroatoms selected from the group consisting of O, N and S;

X represents a cationic entity selected from the group comprising the alkaline cations;

n+m represents the degree of polymerization DP of the co-polyamino acid, that is to say the average number of monomer units per co-polyamino acid chain, and 5≤n+m≤250.

In an embodiment, the composition according to the invention is characterized in that, when the co-polyamino acid comprises aspartate units, then the co-polyamino acid can, in addition, comprise monomer units of formula VIII and/or VIII':

Formula VIII

-continued

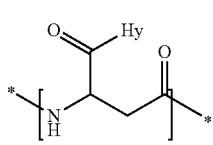

Formula VIII'

"Co-polyamino acid with statistical grafting" is used to denote a co-polyamino acid bearing carboxylate charges and at least one hydrophobic radical, a co-polyamino acid of formula VIIa.

In an embodiment, the composition according to the invention is characterized in that the co-polyamino acid bearing carboxylate charges and hydrophobic radicals is selected from the co-polyamino acids of formulas VII, in which $R_1=R'_1$ and $R_2=R'_2$, of following formula VIIa:

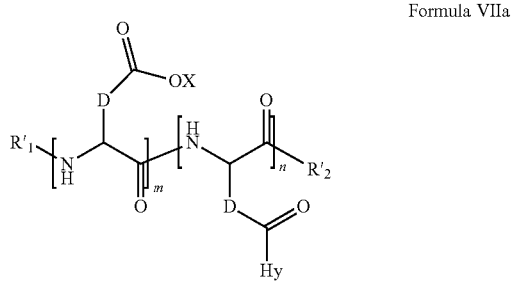

Formula VIIa in which
  m, n, X, D and Hy have the definitions given above,
  $R'_1$ is a radical selected from the group consisting of H, a C2 to C10 linear acyl group, a C4 to C10 branched acyl group, benzyl, a terminal "amino acid" unit and a pyroglutamate,
  $R'_2$ is a —NR'R" radical, R' and R" which are identical or different being selected from the group consisting of H, the C2 to C10 linear or branched or cyclic alkyls, benzyl, and said alkyl R' and R" together optionally forming one or more saturated, unsaturated and/or aromatic carbon rings and/or optionally comprising heteroatoms selected from the group consisting of O, N and S.

In an embodiment, the composition according to the invention is characterized in that the co-polyamino acid bearing carboxylate charges and hydrophobic radicals is selected from the co-polyamino acids of formula VIIa, in which Hy is a radical of formula V.

In an embodiment, the composition according to the invention is characterized in that the co-polyamino acid bearing carboxylate charges and hydrophobic radicals is selected from the co-polyamino acids of formula VIIa, in which Hy has formula V and GpC is a radical of formula IVd.

In an embodiment, the composition according to the invention is characterized in that the co-polyamino acid bearing carboxylate charges and hydrophobic radicals is selected from the co-polyamino acids of formula VIIa, in which Hy is of formula V and GpC is a radical of formula IVd in which x=19.

In an embodiment, the composition according to the invention is characterized in that the co-polyamino acid bearing carboxylate charges and hydrophobic radicals is selected from the co-polyamino acids of formula VIIa, in which Hy is a radical of formula VI.

In an embodiment, the composition according to the invention is characterized in that the co-polyamino acid bearing carboxylate charges and hydrophobic radicals is selected from the co-polyamino acids of formula VIIa, in which Hy is a radical of formula VI in which r=1.

In an embodiment, the composition according to the invention is characterized in that the co-polyamino acid bearing carboxylate charges and hydrophobic radicals is selected from the co-polyamino acids of formula VIIa, in which Hy is a radical of formula VI in which r=1, and for GpC, b=0.

In an embodiment, the composition according to the invention is characterized in that the co-polyamino acid bearing carboxylate charges and hydrophobic radicals is selected from the co-polyamino acids of formula VIIa, in which Hy is of formula VI and GpC is a radical of formula IVd.

In an embodiment, the composition according to the invention is characterized in that the co-polyamino acid bearing carboxylate charges and hydrophobic radicals is selected from the co-polyamino acids of formula VIIa, in which Hy is of formula VI, and GpC is a radical of formula IVd and r=1.

In an embodiment, the composition according to the invention is characterized in that the co-polyamino acid bearing carboxylate charges and hydrophobic radicals is selected from the co-polyamino acids of formula VIIa, in which Hy is of formula VI and GpC is a radical of formula IVd in which x is from 11 to 15.

"Co-polyamino acid with defined grafting" denotes a co-polyamino acid bearing carboxylate charges and at least one hydrophobic radical, a co-polyamino acid of formula VIIb.

In an embodiment, the composition according to the invention is characterized in that the co-polyamino acid bearing carboxylate charges and hydrophobic radicals is selected from the co-polyamino acids of formula VII in which n=0 of following formula VIIb:

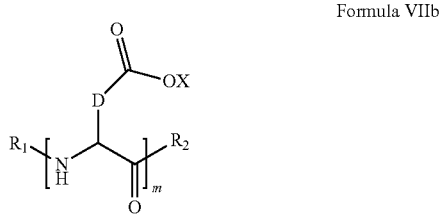

Formula VIIb in which m, X, D, R, and $R_2$ have the definitions given above and at least $R_1$ or $R_2$ is a hydrophobic radical of formula I. V or VI.

In an embodiment, the composition according to the invention is characterized in that the co-polyamino acid bearing carboxylate charges and hydrophobic radicals is selected from the co-polyamino acids of formula VIIb, in which R1=R'1, of formula VIIb':

Formula VIIb'

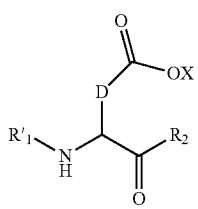

in which m, X, D, R'$_1$ and R$_2$ have the definitions given above and at least R$_2$ is a hydrophobic radical of formula I, V or VI.

In an embodiment, the composition according to the invention is characterized in that the co-polyamino acid bearing carboxylate charges and hydrophobic radicals is selected from the co-polyamino acids of formula VIIb, in which R$_2$=R'$_2$, of formula VIIb":

Formula VIIb"

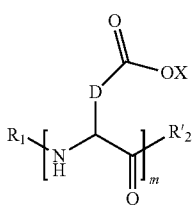

in which m, X, D, R$_1$ and R'$_2$ have the meanings given above and at least R$_1$ is a hydrophobic radical of formula I, V or VI.

In an embodiment, the composition according to the invention is characterized in that the co-polyamino acid bearing carboxylate charges and hydrophobic radicals is selected from the co-polyamino acids of formula VII in which n=0 of formula VIIb and R1 or R2 is a hydrophobic radical of formula L V or VI.

In an embodiment, the composition according to the invention is characterized in that the co-polyamino acid bearing carboxylate charges and hydrophobic radicals is selected from the co-polyamino acids of formula VIIb or VIIb" in which R$_1$ is a hydrophobic radical of formula I, V or VI in which r=0 or r=1 and GpR is of Formula II.

In an embodiment, the composition according to the invention is characterized in that the co-polyamino acid bearing carboxylate charges and hydrophobic radicals is selected from the co-polyamino acids of formula VIIb or VIIb" in which R$_1$ is a hydrophobic radical of formula VI and GpR is of formula II'.

In an embodiment, the composition according to the invention is characterized in that the co-polyamino acid bearing carboxylate charges and hydrophobic radicals is selected from the co-polyamino acids of formula VIIb or VIIb" in which R, is a hydrophobic radical of formula VI and GpR is of formula II' and GpC is of formula Va.

In an embodiment, the composition according to the invention is characterized in that the co-polyamino acid bearing carboxylate charges and hydrophobic radicals is selected from the co-polyamino acids of formula VIIb or VIIb" in which R$_1$ is a hydrophobic radical of formula VI and GpR is of formula II' and GpC is of formula IVd.

In an embodiment, the composition according to the invention is characterized in that the co-polyamino acid bearing carboxylate charges and hydrophobic radicals is selected from the co-polyamino acids of formula VIIb or VIIb' in which R$_2$ is a hydrophobic radical of formula I, V or VI in which r=1 and GpR is of formula II.

In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1 and GpR is of Formula II and a=0.

In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1, GpR is of Formula II and a=0 and GpC is of formula IVa or IVc.

In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1, GpR is of Formula II and a=0 and GpC is of formula IVa.

In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1, GpR is of Formula II and a=0 and GpC is of formula IVc.

In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1, GpR is of Formula II and a=0 and GpC is of formula IVd or IVf. In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1, GpR is of Formula II and a=0 and GpC is of formula IVd.

In an embodiment, the composition according to the invention is characterized in that the co-polyamino acid bearing carboxylate charges and hydrophobic radicals is selected from the co-polyamino acids of formula VIIb' in which R$_2$ is a hydrophobic radical of formula V in which r=1, GpR is of formula II and a=0 and GpC is of formula IVf.

In an embodiment, the composition according to the invention is characterized in that the co-polyamino acid bearing carboxylate charges and hydrophobic radicals is selected from the co-polyamino acids of formulas VIIb' in which R$_2$ is a hydrophobic radical of formula VI in which r=1 and GpR is of Formula II and a=1.

In an embodiment, the composition according to the invention is characterized in that the co-polyamino acid bearing carboxylate charges and hydrophobic radicals is selected from the co-polyamino acids of formulas VIIb' in which R$_2$ is a hydrophobic radical of formula VI in which r=1, GpR is of Formula II, a=1 and GpC is of formula IVa or IVd.

In an embodiment, the composition according to the invention is characterized in that the co-polyamino acid bearing carboxylate charges and hydrophobic radicals is selected from the co-polyamino acids of formulas VIIb' in which $R_2$ is a hydrophobic radical of formula VI in which r=1, GpR is of Formula II, a=1 and GpC is of formula IVd.

In an embodiment, the composition according to the invention is characterized in that the co-polyamino acid bearing carboxylate charges and hydrophobic radicals is selected from the co-polyamino acids of formulas VIIb' in which $R_2$ is a hydrophobic radical of formula VI in which r=1, GpR is of Formula II, a=1 and GpC is of formula IVd, with x=11.

In an embodiment, the composition according to the invention is characterized in that the co-polyamino acid bearing carboxylate charges and hydrophobic radicals is selected from the co-polyamino acids of formulas VIIb' in which $R_2$ is a hydrophobic radical of formula VI in which r=1, GpR is of Formula II, a=1 and GpC is of formula IVd, with x=13.

In an embodiment, the composition according to the invention is characterized in that the co-polyamino acid bearing carboxylate charges and hydrophobic radicals is selected from the co-polyamino acids of formulas VIIb' in which $R_2$ is a hydrophobic radical of formula VI in which r=1, GpR is of Formula II, a=1 and GpC is of formula IVd with x=15.

In an embodiment, the composition is characterized in that the co-polyamino acid bearing carboxylate charges and hydrophobic radicals is selected from the co-polyamino acids of following formula XX:

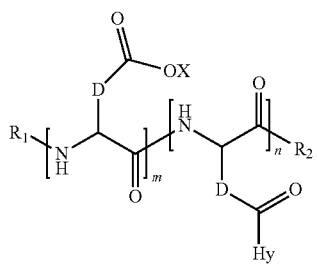

Formula XX in which,

D represents, independently, either a —$CH_2$— group (aspartic unit) or a —$CH_2$—$CH_2$— group (glutamic unit), Hy is a hydrophobic radical selected from the hydrophobic radicals of formula I, V or VI, in which r=1 and GpR is a radical of Formula II, $R_1$ is a hydrophobic radical selected from the hydrophobic radicals of formula I, V or VI in which r=0 or r=1 and GpR is a radical of Formula II', or a radical selected from the group consisting of H, a C2 to C10 linear acyl group, a C3 to C10 branched acyl group, benzyl, a terminal "amino acid" unit and a pyroglutamate, $R_2$ is a hydrophobic radical selected from the hydrophobic radicals of formula I, V or VI in which r=1 and GpR is a radical of Formula II, or a —NR'R" radical, R' and R", which are identical or different, being selected from the group consisting of H, the C2 to C10 linear or branched or cyclic alkyls, benzyl and said alkyl R' and R" together optionally forming one or more saturated, unsaturated and/or aromatic carbon rings and/or optionally comprising heteroatoms, selected from the group consisting of O, N and S, at least one of the $R_1$ or $R_2$ is a hydrophobic radical as defined above, X represents H or a cationic entity selected from the group comprising the metallic cations;

n+m represents the degree of polymerization DP of the co-polyamino acid, that is to say the average number of monomer units per co-polyamino acid chain and 5≤n+m≤250.

In an embodiment, the composition according to the invention is characterized in that $R_1$ is a radical selected from the group consisting of a $C_2$ to $C_{10}$ linear acyl group, a $C_4$ to $C_{10}$ branched acyl group, benzyl, a terminal "amino acid" group and a pyroglutamate.

In an embodiment, the composition according to the invention is characterized in that R, is a radical selected from the group consisting of a $C_2$ to $C_{10}$ linear acyl group or a $C_4$ to $C_{10}$ branched acyl group.

In an embodiment, the composition according to the invention is characterized in that the co-polyamino acid bearing carboxylate charges and hydrophobic radicals is selected from the co-polyamino acids of formula VII, VIIa or VIIb in which the co-polyamino acid is selected from the co-polyamino acids in which group D is a —$CH_2$— group (aspartic unit).

In an embodiment, the composition according to the invention is characterized in that the co-polyamino acid bearing carboxylate charges and hydrophobic radicals is selected from the co-polyamino acids of formula VII, VIIa or VIIb in which the co-polyamino acid is selected from the co-polyamino acids in which group D is a —$CH_2$—$CH_2$— group (glutamic unit).

The ratio of hydrophobic radical to basal insulin is defined to be the ratio of their respective molar concentrations: [Hy]/[basal insulin] (mol/mol) until obtaining the expected performances, namely the solubilization of basal insulin at a pH from 6.0 to 8.0, the precipitation of the basal insulin, and the stability of the compositions according to the invention.

The minimum value of the ratio of hydrophobic radical to basal insulin [Hy]/[basal insulin] measured is the value at which the basal insulin is solubilized, since the solubilization is the minimum effect to be obtained: this solubilization determines all the other technical effects which can be observed only if the basal insulin is solubilized at a pH from 6.0 to 8.0.

In the compositions according to the invention, the ratio of hydrophobic radical over basal insulin [Hy]/[basal insulin] can be greater than the minimum value determined by the solubilization limit.

In an embodiment, the ratio of hydrophobic radical over basal insulin [Hy]/[basal insulin]≤2.

In an embodiment, the ratio of hydrophobic radical over basal insulin [Hy]/[basal insulin]≤1.75.

In an embodiment, the ratio of hydrophobic radical over basal insulin [Hy]/[basal insulin]≤1.5.

In an embodiment, the ratio of hydrophobic radical over basal insulin [Hy]/[basal insulin]≤1.25.

In an embodiment, the ratio of hydrophobic radical over basal insulin [Hy]/[basal insulin]≤1.00.

In an embodiment, the ratio of hydrophobic radical over basal insulin [Hy]/[basal insulin]≤0.75.

In an embodiment, the ratio of hydrophobic radical over basal insulin [Hy]/[basal insulin]≤0.5.

In an embodiment, the ratio of hydrophobic radical over basal insulin [Hy]/[basal insulin]≤0.25

In an embodiment, the composition according to the invention is characterized in that the ratio i between the number of hydrophobic radicals and the number of glutamic or aspartic units is from 0.007 to 0.3.

In an embodiment, the composition according to the invention is characterized in that the ratio i between the number of hydrophobic radicals and the number of glutamic or aspartic units is from 0.01 to 0.3.

In an embodiment, the composition according to the invention is characterized in that the ratio i between the number of hydrophobic radicals and the number of glutamic or aspartic units is from 0.02 to 0.2.

In an embodiment, the composition according to the invention is characterized in that the hydrophobic radical corresponds to formula VI, and the ratio i between the number of hydrophobic radicals and the number of glutamic or aspartic units is from 0.007 to 0.15.

In an embodiment, the composition according to the invention is characterized in that the hydrophobic radical corresponds to formula VI, and the ratio i between the number of hydrophobic radicals and the number of glutamic or aspartic units is from 0.01 to 0.1.

In an embodiment, the composition according to the invention is characterized in that the hydrophobic radical corresponds to formula VI, and the ratio i between the number of hydrophobic radicals and the number of glutamic or aspartic units is from 0.02 to 0.08.

In an embodiment, the composition according to the invention is characterized in that the hydrophobic radical corresponds to formula VI in which the radical Cx comprises from 9 to 10 carbon atoms, and the ratio i between the number of hydrophobic radicals and the number of glutamic or aspartic units is from 0.03 to 0.15.

In an embodiment, the composition according to the invention is characterized in that the hydrophobic radical corresponds to formula VI in which the radical Cx comprises from 11 to 12 carbon atoms, and the ratio i between the number of hydrophobic radicals and the number of glutamic or aspartic units is from 0.015 to 0.1.

In an embodiment, the composition according to the invention is characterized in that the hydrophobic radical corresponds to formula VI in which the radical Cx comprises from 11 to 12 carbon atoms, and the ratio i between the number of hydrophobic radicals and the number of glutamic or aspartic units is from 0.02 to 0.08.

In an embodiment, the composition according to the invention is characterized in that the hydrophobic radical corresponds to formula VI in which the radical Cx comprises from 13 to 15 carbon atoms, and the ratio i between the number of hydrophobic radicals and the number of glutamic or aspartic units is from 0.01 to 0.1.

In an embodiment, the composition according to the invention is characterized in that the hydrophobic radical corresponds to formula VI in which the radical Cx comprises from 13 to 15 carbon atoms, and the ratio i between the number of hydrophobic radicals and the number of glutamic or aspartic units is from 0.01 to 0.06.

In an embodiment, the composition according to the invention is characterized in that the hydrophobic radical corresponds to formula V, and the ratio i between the number of hydrophobic radicals and the number of glutamic or aspartic units is from 0.007 to 0.3.

In an embodiment, the composition according to the invention is characterized in that the hydrophobic radical corresponds to formula V, and the ratio i between the number of hydrophobic radicals and the number of glutamic or aspartic units is from 0.01 to 0.3.

In an embodiment, the composition according to the invention is characterized in that the hydrophobic radical corresponds to formula V, and the ratio i between the number of hydrophobic radicals and the number of glutamic or aspartic units is from 0.015 to 0.2.

In an embodiment, the composition according to the invention is characterized in that the hydrophobic radical corresponds to formula V in which the radical Cx comprises from 11 to 14 carbon atoms, and the ratio i between the number of hydrophobic radicals and the number of glutamic or aspartic units is from 0.1 to 0.2.

In an embodiment, the composition according to the invention is characterized in that the hydrophobic radical corresponds to formula V in which the radical Cx comprises from 15 to 16 carbon atoms, and the ratio i between the number of hydrophobic radicals and the number of glutamic or aspartic units is from 0.04 to 0.15.

In an embodiment, the composition according to the invention is characterized in that the hydrophobic radical corresponds to formula V in which the radical Cx comprises from 17 to 18 carbon atoms, and the ratio i between the number of hydrophobic radicals and the number of glutamic or aspartic units is from 0.02 to 0.06.

In an embodiment, the composition according to the invention is characterized in that the hydrophobic radical corresponds to formula V in which the radical Cx comprises from 19 to 25 carbon atoms, and the ratio i between the number of hydrophobic radicals and the number of glutamic or aspartic units is from 0.01 to 0.06.

In an embodiment, the composition according to the invention is characterized in that the hydrophobic radical corresponds to formula V in which the radical Cx comprises from 19 to 25 carbon atoms, and the ratio i between the number of hydrophobic radicals and the number of glutamic or aspartic units is from 0.01 to 0.05.

In an embodiment, the composition according to the invention is characterized in that n+m is from 10 to 200.

In an embodiment, the composition according to the invention is characterized in that n+m is from 15 to 150.

In an embodiment, the composition according to the invention is characterized in that n+m is from 15 to 100.

In an embodiment, the composition according to the invention is characterized in that n+m is from 15 to 80.

In an embodiment, the composition according to the invention is characterized in that n+m is from 15 to 65.

In an embodiment, the composition according to the invention is characterized in that n+m is from 20 to 60.

In an embodiment, the composition according to the invention is characterized in that n+m is from 20 to 50.

In an embodiment, the composition according to the invention is characterized in that n+m is from 20 to 40.

In an embodiment, the at least one hydrophobic radical of formula I is selected from the radicals of formula I in which r=1, a=0, p=1, GpR corresponds to formula II in which R is

*~~O~~O~~O~~*,

GpC corresponds to formula IVd in which x=15 and Cx is

*~~~~~~~$CH_3$.

In an embodiment, the at least one hydrophobic radical of formula I is selected from the radicals of formula I in which r=1, a=0, p 1, GpR corresponds to formula II in which R is

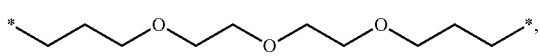

GpC corresponds to formula IVd in which x=19 and Cx is

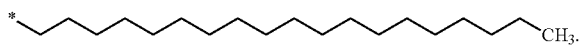

In an embodiment, the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=9 and Cx is

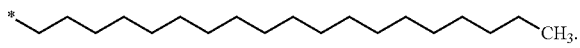

In an embodiment, the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

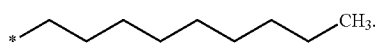

In an embodiment, the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=13 and Cx is

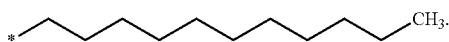

In an embodiment, the at least one hydrophobic radical of formula I is selected from the radicals of formula I in which r=1, a=1, p=2, GpR corresponds to formula II in which R is

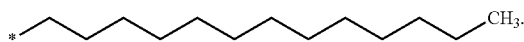

GpA corresponds to formula IIIb, GpC corresponds to formula IVd in which x=13 and Cx is

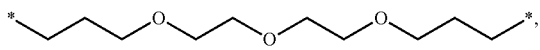

In an embodiment, the co-polyamino acid bearing carboxylate charges and hydrophobic radicals is a co-polyamino acid of formula VII or VIIa, in which DP=22+/−5, i=0.05+/−0.02, and the at least one hydrophobic radical of formula I is selected from the radicals of formula I in which r=1, a=0, p=1, GpR corresponds to formula II in which R is

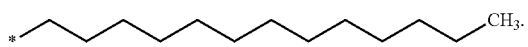

GpC corresponds to formula IVd in which x=19 and Cx is

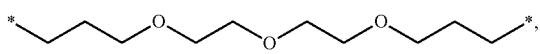

The values of the degree of polymerization DP and of ratio i are estimated by $^1$H NMR in D$_2$O by comparing the integration of the signals originating from the hydrophobic groups with that of the signals originating from the main chain of the co-polyamino acid.

In an embodiment, the co-polyamino acid bearing carboxylate charges and hydrophobic radicals is a co-polyamino acid of formula VII or VIIa, in which DP=25+/−5, i=0.07+/−0.02, and the at least one hydrophobic radical of formula I is selected from the radicals of formula I in which r=1, a=0, p=1, GpR corresponds to formula II in which R is

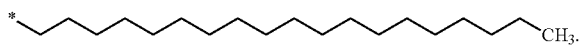

GpC corresponds to formula IVd in which x=15 and Cx is

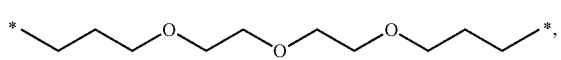

In an embodiment, the co-polyamino acid bearing carboxylate charges and hydrophobic radicals is a co-polyamino acid of formula VII or VIIa, in which DP=23+/−5, i=0.05+/−0.02, and the at least one hydrophobic radical of formula I is selected from the radicals of formula I in which r=1, a=0, p=1, GpR corresponds to formula II in which R is

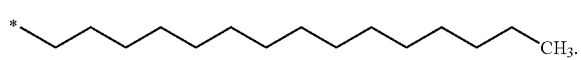

GpC corresponds to formula IVd in which x=19 and Cx is

In an embodiment, the co-polyamino acid bearing carboxylate charges and hydrophobic radicals is a co-polyamino acid of formula VII or VIIb, in which DP=25+/−5, 0.033≤i≤0.05, and the hydrophobic radical of formula I is selected from the radicals of formula I in which r=1, a=0, p=1, GpR corresponds to formula II in which R is

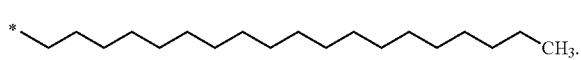

GpC corresponds to formula IVd in which x=19 and Cx is

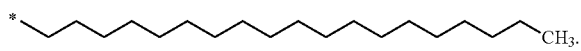 [SMILES: CCCCCCCCCCCCCCCCCCCC]

In an embodiment, the co-polyamino acid bearing carboxylate charges and hydrophobic radicals is a co-polyamino acid of formula VII or VIIa, in which DP=22+/−5, i=0.05+/−0.02, and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

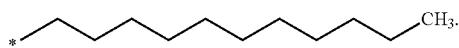

In an embodiment, the co-polyamino acid bearing carboxylate charges and hydrophobic radicals is a co-polyamino acid of formula VII or VIIa, in which DP=35+/−5, i=0.05+/−0.02, and the at least one hydrophobic radical of formula I is selected from the radicals of formula I in which r=1, a=1, p=2, GpR corresponds to formula II and in which R is —CH2-CH2-, GpA corresponds to formula IIIb, GpC corresponds to formula IVd in which x=11 and Cx is

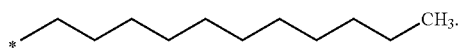

In an embodiment, the co-polyamino acid bearing carboxylate charges and hydrophobic radicals is a co-polyamino acid of formula VII or VIIa, in which DP=65+/−5, i=0.05+/−0.02, and the at least one hydrophobic radical of formula I is selected from the radicals of formula I in which r=1, a=1, p=2, GpR corresponds to formula II in which R is —CH$_2$—CH$_2$—, GpA corresponds to formula IIIb, GpC corresponds to formula IVd in which x=11 and Cx is

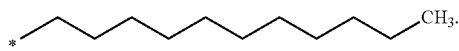

In an embodiment, the co-polyamino acid bearing carboxylate charges and hydrophobic radicals is a co-polyamino acid of formula VII or VIIa, in which DP=22+/−5, i=0.04+/−0.02, and the at least one hydrophobic radical of formula I is selected from the radicals of formula I in which r=1, a=1, p=2, GpR corresponds to formula I in which R is —CH$_2$—CH$_2$—, GpA corresponds to formula IIIb, GpC corresponds to formula IVd in which x=13 and Cx is

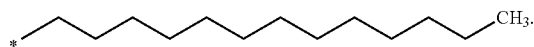

In an embodiment, the co-polyamino acid bearing carboxylate charges and hydrophobic radicals is a co-polyamino acid of formula VII or VIIa, in which DP=22+/−5, i=0.03+/−0.01, and the at least one hydrophobic radical of formula I is selected from the radicals of formula I in which r=1, a=1, p=2, GpR corresponds to formula II in which R is

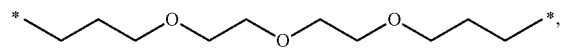

GpA corresponds to formula IIIb, GpC corresponds to formula IVd in which x=13 and Cx is

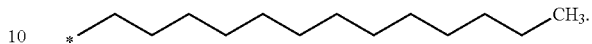

In an embodiment, the co-polyamino acid bearing carboxylate charges and hydrophobic radicals is a co-polyamino acid of formula VII or VIIa, in which DP=22+/−5, i=0.07+/−0.02, and the at least one hydrophobic radical of formula I is selected from the radicals of formula I in which r=1, a=1, p=2, GpR corresponds to formula II in which R is

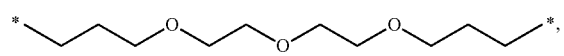

GpA corresponds to formula IIIb, GpC corresponds to formula IVd in which x=9 and Cx is

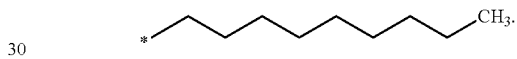

In an embodiment, the co-polyamino acid bearing carboxylate charges and hydrophobic radicals is a co-polyamino acid of formula VII or VIIb, in which DP=27+/−5, 0.031≤i≤0.045, and the at least one hydrophobic radical of formula I is selected from the radicals of formula I in which r=1, a=, p=2, GpR corresponds to formula II in which R is —CH2-CH2-, GpA corresponds to formula IIIb, GpC corresponds to formula IVd in which x=11 and Cx is

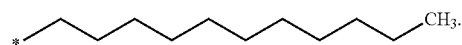

In an embodiment, the co-polyamino acid bearing carboxylate charges and hydrophobic radicals is a co-polyamino acid of formula VII or VIIb, in which DP=22+/−5, 0.037≤i≤0.055, and the at least one hydrophobic radical of formula I is selected from the radicals of formula I in which r=, a=1, p=2, GpR corresponds to formula II in which R is —CH2-C$_2$—, GpA corresponds to formula IIIb, GpC corresponds to formula IVd in which x=13 and Cx is

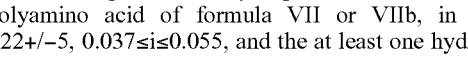

In an embodiment, the co-polyamino acid bearing carboxylate charges and hydrophobic radicals is a co-polyamino acid of formula VII or VIIb, in which DP=22+/−5, 0.037≤i≤0.055, and the at least one hydrophobic radical of formula I is selected from the radicals of formula I in which r=1, a=1, p=2, GpR corresponds to formula II in which R is

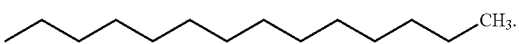

*〜〜〜O〜〜O〜〜O〜〜*,

GpA corresponds to formula IIIb, GpC corresponds to formula IVd in which x=13 and Cx is

*〜〜〜〜〜〜CH₃.

In an embodiment, the co-polyamino acid bearing carboxylate charges and hydrophobic radicals is a co-polyamino acid of formula VII or VIIb, in which DP=60+/−10, $0.014 \leq i \leq 0.02$, and the at least one hydrophobic radical of formula I is selected from the radicals of formula I in which r=1, a=1, p=2, GpR corresponds to formula II in which R is —CH₂—CH₂—, GpA corresponds to formula IIIb, GpC corresponds to formula IVd in which x=13 and Cx is

*〜〜〜〜〜〜CH₃.

In an embodiment, the co-polyamino acid bearing carboxylate charges and hydrophobic radicals is a co-polyamino acid of formula VII or VIIb, in which DP=40+/−5, $0.022 \leq i \leq 0.029$, and the at least one hydrophobic radical of formula I is selected from the radicals of formula I in which r=1, a=1, p=2, GpR corresponds to formula II in which R is —CH₂—CH₂—, GpA corresponds to formula IIIb, GpC corresponds to formula IVd in which x=13 and Cx is

*〜〜〜〜〜〜CH₃.

The invention also relates to said co-polyamino acids bearing carboxylate charges and hydrophobic radicals of formula I, V or VI.

In an embodiment, the invention also relates to the precursors of said hydrophobic radicals of formulas I', V' and VI':

H—(GpR)$_r$—(GpA)$_a$—(GpC)$_p$   formula I'

H—(GpR)$_r$—(GpA)$_a$—GpC   formula V'

H—(GpR)$_r$—GpA—(GpC)$_2$   formula VI'

GpR, GpA, GpC, r, a, p have the meanings given above.

The invention also relates to a method for preparing stable injectable solutions.

In an embodiment, the composition according to the invention is characterized in that the co-polyamino acid originates from a polyamino acid obtained by polymerization.

In an embodiment, the composition according to the invention is characterized in that the co-polyamino acid originates from a polyamino acid obtained by ring-opening polymerization of a glutamic acid N-carboxyanhydride derivative or an aspartic acid N-carboxyanhydride derivative.

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative described in the review article Adv. Polym. Sci. 2006, 202, 1-18 (Deming, T. J.).

In an embodiment, the composition according to the invention is characterized in that the co-polyamino acid originates from a polyamino acid obtained by polymerization of a glutamic acid N-carboxyanhydride derivative.

In an embodiment, the composition according to the invention is characterized in that the co-polyamino acid originates from a polyamino acid obtained by polymerization of a glutamic acid N-carboxyanhydride derivative selected from the group consisting of methyl polyglutamate N-carboxyanhydride (GluOMe-NCA), benzyl polyglutamate N-carboxyanhydride (GluOBzl-NCA), and t-butyl polyglutamate N-carboxyanhydride (GluOtBu-NCA).

In an embodiment, the glutamic acid N-carboxyanhydride derivative is methyl poly-L-glutamate N-carboxyanhydride (L-GluOMe-NCA).

In an embodiment, the glutamic acid N-carboxyanhydride derivative is benzyl poly-L-glutamate N-carboxyanhydride (L-GluOBzl-NCA).

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative using, using as initiator an organometallic complex of a transition metal, as described in the publication Nature 1997, 390, 386-389 (Deming, T. J.).

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative, using as initiator ammonia or a primary amine as described in the patent FR 2,801,226 (Touraud, F.; et al.) and the references cited in this patent.

In an embodiment, the composition according to the invention is characterized in that the co-polyamino acid originates from a polyamino acid obtained by polymerization of a glutamic acid N-carboxyanhydride derivative or of an aspartic acid N-carboxyanhydride derivative, using as initiator hexamethyldisilazane as described in the publication J. Am. Chem. Soc. 2007, 129, 14114-14115 (Lu H.; et al.) or a silylated amine as described in the publication J. Am. Chem. Soc. 2008, 130, 12562-12563 (Lu H.; et al.).

In an embodiment, the composition according to the invention is characterized in that the method for synthetizing the polyamino acid obtained by polymerization of a glutamic acid N-carboxyanhydride derivative or an aspartic acid N-carboxyanhydride derivative from which the co-polyamino acid originates comprises a step of hydrolysis of ester functions.

In an embodiment, this step of hydrolysis of ester functions can consist of a hydrolysis in an acidic medium or a hydrolysis in an alkaline medium or it can be carried out by hydrogenation.

In an embodiment, this step of hydrolysis of ester groups is a hydrolysis in an acidic medium.

In an embodiment, this step of hydrolysis of ester groups is carried out by hydrogenation.

In an embodiment, the composition according to the invention is characterized in that the co-polyamino acid originates from a polyamino acid obtained by depolymerization of a polyamino acid of higher molecular weight.

In an embodiment, the composition according to the invention is characterized in that the co-polyamino acid originates from a polyamino acid obtained by enzymatic depolymerization of a polyamino acid of higher molecular weight.

In an embodiment, the composition according to the invention is characterized in that the co-polyamino acid originates from a polyamino acid obtained by chemical depolymerization of a polyamino acid of higher molecular weight.

In an embodiment, the composition according to the invention is characterized in that the co-polyamino acid originates from a polyamino acid obtained by enzymatic and chemical depolymerization of a polyamino acid of higher molecular weight.

In an embodiment, the composition according to the invention is characterized in that the co-polyamino acid originates from a polyamino acid obtained by depolymerization of a polyamino acid of higher molecular weight selected from the group consisting of sodium polyglutamate and sodium polyaspartate.

In an embodiment, the composition according to the invention is characterized in that the co-polyamino acid originates from a polyamino acid obtained by depolymerization of a sodium polyglutamate of higher molecular weight.

In an embodiment, the composition according to the invention is characterized in that the co-polyamino acid originates from a polyamino acid obtained by depolymerization of a sodium polyaspartate of higher molecular weight.

In an embodiment, the composition according to the invention is characterized in that the co-polyamino acid is obtained by grafting a hydrophobic group onto a poly-L-glutamic acid or poly-L-aspartic acid using the methods for forming amide bonds, which are well known to the person skilled in the art.

In an embodiment, the composition according to the invention is characterized in that the co-polyamino acid is obtained by grafting of a hydrophobic group onto a poly-L-glutamic acid or poly-L-aspartic acid using the methods for forming amide bonds, used for peptide synthesis.

In an embodiment, the composition according to the invention is characterized in that the co-polyamino acid is obtained by grafting of a hydrophobic group onto a poly-L-glutamic acid or poly-L-aspartic acid as described in the patent FR 2,840,614 (Chan, Y. P.; et al.).

Below, the units used for the insulins are those recommended by the pharmacopoeias; the associated correspondences in mg/mL are given in the table below:

A basal insulin of which the isoelectric point is from 5.8 to 8.5 is understood to mean an insulin which is insoluble at pH 7 and the duration of action of which is from 8 to 24 hours or more in the standard diabetes models.

These basal insulins whose isoelectric point is from 5.8 to 8.5 are recombinant insulins of which the primary structure has been modified primarily by the introduction of alkaline amino acids such as arginine or lysine. They are described, for example, in the following patents, patent applications or publications WO 2003/053339, WO 2004/096854, U.S. Pat. Nos. 5,656,722 and 6,100,376 the content of which is incorporated by reference.

In an embodiment, the basal insulin of which the isoelectric point is from 5.8 to 8.5 is insulin glargine. Insulin glargine is marketed under the trade name of Lantus® (100 U/mL) or Toujeo® (300 U/mL) by SANOFI.

In an embodiment, the basal insulin of which the isoelectric point is from 5.8 to 8.5 is a biosimilar insulin glargine.

A biosimilar insulin glargine is in the process of being marketed under the trade name of Abasaglar® or Basaglar® by ELI LILLY.

In an embodiment, the compositions according to the invention comprise from 40 to 500 U/mL of basal insulin of which the isoelectric point is from 5.8 to 8.5.

In an embodiment, the compositions according to the invention comprise 40 U/mL of a basal insulin of which the isoelectric point is from 5.8 to 8.5.

In an embodiment, the compositions according to the invention comprise 100 U/mL (or approximately 3.6 mg/mL) of basal insulin of which the isoelectric point is from 5.8 to 8.5.

In an embodiment, the compositions according to the invention comprise 150 U/mL of basal insulin of which the isoelectric point is from 5.8 to 8.5.

In an embodiment, the compositions according to the invention comprise 200 U/mL of basal insulin of which the isoelectric point is from 5.8 to 8.5.

In an embodiment, the compositions according to the invention comprise 225 U/mL of basal insulin of which the isoelectric point is from 5.8 to 8.5.

In an embodiment, the compositions according to the invention comprise 250 U/mL of basal insulin of which the isoelectric point is from 5.8 to 8.5.

In an embodiment, the compositions according to the invention comprise 300 U/mL of basal insulin of which the isoelectric point is from 5.8 to 8.5.

In an embodiment, the compositions according to the invention comprise 400 U/mL of basal insulin of which the isoelectric point is from 5.8 to 8.5.

In an embodiment, the compositions according to the invention comprise 500 U/mL of basal insulin of which the isoelectric point is from 5.8 to 8.5.

In an embodiment, the weight ratio between the basal insulin of which the isoelectric point is from 5.8 to 8.5 and the co-polyamino acid, or co-polyamino acid/basal insulin, is from 0.2 to 8.

| Insulin | EP Pharmacopoeia EP 8.0 (2014) | US Pharmacopoeia - USP38 (2015) |
|---|---|---|
| Aspart | 1 U = 0.0350 mg of insulin aspart | 1 USP = 0.0350 mg of insulin aspart |
| Lispro | 1 U = 0.0347 mg of insulin lispro | 1 USP = 0.0347 mg of insulin lispro |
| Human | 1 IU = 0.0347 mg of human insulin | 1 USP = 0.0347 mg of human insulin |
| Glargine | 1 U = 0.0364 mg of insulin glargine | 1 USP = 0.0364 mg of insulin glargine |
| Pork | 1 IU = 0.0345 mg of pork insulin | 1 USP = 0.0345 mg of pork insulin |
| Beef | 1 IU = 0.0342 mg of beef insulin | 1 USP = 0.0342 mg of beef insulin |

In an embodiment, the weight ratio is from 0.2 to 6.
In an embodiment, the weight ratio is from 0.2 to 5.
In an embodiment, the weight ratio is from 0.2 to 4.
In an embodiment, the weight ratio is from 0.2 to 3.
In an embodiment, the weight ratio is from 0.2 to 2.
In an embodiment, the weight ratio is from 0.2 to 1.

In an embodiment, the concentration of co-polyamino acid bearing carboxylate charges and hydrophobic radicals is at most 60 mg/mL.

In an embodiment, the concentration of co-polyamino acid bearing carboxylate charges and hydrophobic radicals is at most 40 mg/mL.

In an embodiment, the concentration of co-polyamino acid bearing carboxylate charges and hydrophobic radicals is at most 20 mg/mL.

In an embodiment, the concentration of co-polyamino acid bearing carboxylate charges and hydrophobic radicals is at most 10 mg/mL.

In an embodiment, the concentration of co-polyamino acid bearing carboxylate charges and hydrophobic radicals is at most 5 mg/mL.

In an embodiment, the concentration of co-polyamino acid bearing carboxylate charges and hydrophobic radicals is at most 2.5 mg/mL.

In an embodiment, the compositions according to the invention comprise a prandial insulin. The prandial insulins are soluble at pH 7.

A prandial insulin is understood to mean a so-called rapid or "regular" insulin.

The so-called rapid prandial insulins are insulins that have to respond to the needs induced by the ingestion of proteins and saccharides during a meal; they must act within less than 30 minutes.

In an embodiment, the so-called "regular" prandial insulin is human insulin.

In an embodiment, the prandial insulin is a recombinant human insulin as described in the European Pharmacopoeia and the American Pharmacopoeia.

The human insulin is marketed under the trade names of Humulin® (ELI LILLY) and Novolin® (NOVO NORDISK), for example.

The so-called very rapid (fast acting) prandial insulins are insulins which are obtained by recombination and the primary structure of which was modified in order to decrease their time of action.

In an embodiment, the so-called very rapid (fast acting) prandial insulins are selected from the group comprising the insulin lispro (Humalog®), insulin glulisine (Apidra®), and the insulin aspart (NovoLog®).

In an embodiment, the prandial insulin is insulin lispro.
In an embodiment, the prandial insulin is insulin glulisine.
In an embodiment, the prandial insulin is insulin aspart.

In an embodiment, the compositions according to the invention comprise in total from 60 to 800 U/mL of insulin with a combination of prandial insulin and of basal insulin of which the isoelectric point is from 5.8 to 8.5.

In an embodiment, the compositions according to the invention comprise in total from 100 to 500 U/mL of insulin with a combination of prandial insulin and of basal insulin of which the isoelectric point is from 5.8 to 8.5.

In an embodiment, the compositions according to the invention comprise in total 800 U/mL of insulin with a combination of prandial insulin and of basal insulin of which the isoelectric point is from 5.8 to 8.5.

In an embodiment, the compositions according to the invention comprise in total 700 U/mL of insulin with a combination of prandial insulin and of basal insulin of which the isoelectric point is from 5.8 to 8.5.

In an embodiment, the compositions according to the invention comprise in total 600 U/mL of insulin with a combination of prandial insulin and of basal insulin of which the isoelectric point is from 5.8 to 8.5.

In an embodiment, the compositions according to the invention comprise in total 500 U/mL of insulin with a combination of prandial insulin and of basal insulin of which the isoelectric point is from 5.8 to 8.5.

In an embodiment, the compositions according to the invention comprise in total 400 U/mL of insulin with a combination of prandial insulin and of basal insulin of which the isoelectric point is from 5.8 to 8.5.

In an embodiment, the compositions according to the invention comprise in total 300 U/mL of insulin with a combination of prandial insulin and of basal insulin of which the isoelectric point is from 5.8 to 8.5.

In an embodiment, the compositions according to the invention comprise in total 266 U/mL of insulin with a combination of prandial insulin and of basal insulin of which the isoelectric point is from 5.8 to 8.5.

In an embodiment, the compositions according to the invention comprise in total 200 U/mL of insulin with a combination of prandial insulin and of basal insulin of which the isoelectric point is from 5.8 to 8.5.

In an embodiment, the compositions according to the invention comprise in total 100 U/mL of insulin with a combination of prandial insulin and of basal insulin of which the isoelectric point is from 5.8 to 8.5.

The proportions between the basal insulin of which the isoelectric point is from 5.8 to 8.5, and the prandial insulin are, for example, expressed in percentage, 25/75, 30/70, 40/60, 50/50, 60/40, 63/37, 70/30, 75/25, 80/20, 83/17, 90/10 for formulations as described above comprising 60 to 800 U/mL. However, any other proportion can be used.

In an embodiment, the compositions according to the invention comprise a gastrointestinal hormone.

"Gastrointestinal hormones" is understood to mean the hormones selected from the group consisting of GLP-1 RA (glucagon like peptide-1 receptor agonist) and GIP (glucose-dependent insulinotropic peptide), oxyntomoduline (a proglucagon derivative), the peptide YY, amylin, cholecystokinin, the pancreatic polypeptide (PP), ghrelin and enterostatin, the analogs or derivatives thereof and/or the pharmaceutically acceptable salts thereof.

In an embodiment, the gastrointestinal hormones are GLP-1 RA analogs or derivatives selected from the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), the analogs or derivatives thereof and the pharmaceutically acceptable salts thereof.

In an embodiment, the gastrointestinal hormone is pramlintide or Symlin® (ASTRA-ZENECA).

In an embodiment, the gastrointestinal hormone is exenatide or Byetta®, the analogs or derivatives thereof and the pharmaceutically acceptable salts thereof.

In an embodiment, the gastrointestinal hormone is liraglutide or Victoza®, the analogs or derivatives thereof and the pharmaceutically acceptable salts thereof.

In an embodiment, the gastrointestinal hormone is lixisenatide or Lyxumia®, the analogs or derivatives thereof and the pharmaceutically acceptable salts thereof.

In an embodiment, the gastrointestinal hormone is albiglutide or Tanzeum®, the analogs or derivatives thereof and the pharmaceutically acceptable salts thereof.

In an embodiment, the gastrointestinal hormone is dulaglutide or Trulicity®, the analogs or derivatives thereof and the pharmaceutically acceptable salts thereof.

In an embodiment, the gastrointestinal hormone is pramlintide or Symlin®, the analogs or derivatives thereof and the pharmaceutically acceptable salts thereof.

"Analog," when used in reference to a peptide or a protein, is understood to mean a peptide or a protein in which one or more constitutive residues of amino acids have been substituted by other residues of amino acids and/or in which one or more constitutive residues of amino acids have been eliminated and/or in which one or more constitutive residues of amino acids have been added. The admissible percentage of homology for the present definition of an analog is 50%.

"Derivative," when used in reference to a peptide or a protein, is understood to mean a peptide or a protein or an analog which has been chemically modified by a substituent which is not present in the peptide or the protein or the analog of reference, that is to say a peptide or a protein which has been made by creation of covalent bonds, in order to introduce substituents.

In an embodiment, the substituent is selected from the group consisting of fatty chains.

In an embodiment, the concentration of gastrointestinal hormone is in an interval from 0.01 to 100 mg/mL.

In an embodiment, the concentration of exenatide, the analogs or derivatives thereof and the pharmaceutically acceptable salts thereof is in an interval from 0.04 to 0.5 mg/mL.

In an embodiment, the concentration of liraglutide, the analogs or derivatives thereof and the pharmaceutically acceptable salts thereof is in an interval from 1 to 10 mg/mL.

In an embodiment, the concentration of lixisenatide, the analogs or derivatives thereof and the pharmaceutically acceptable salts thereof is in an interval from 0.01 to 1 mg/mL.

In an embodiment, the concentration of albiglutide, the analogs or derivatives thereof and the pharmaceutically acceptable salts thereof is from 5 to 100 mg/mL.

In an embodiment, the concentration of dulaglutide, the analogs or derivatives thereof and the pharmaceutically acceptable salts thereof is from 0.1 to 10 mg/mL.

In an embodiment, the concentration of pramlintide, the analogs or derivatives thereof and the pharmaceutically acceptable salts thereof is from 0.1 to 5 mg/mL.

In an embodiment, the compositions according to the invention are produced by mixing commercial solutions of basal insulin of which the isoelectric point is from 5.8 to 8.5, and commercial solutions of GLP-1 RA, of GLP-1 RA analog or derivative in ratios by volume in an interval from 10/90 to 90/10.

In an embodiment, the composition according to the invention comprises a daily dose of basal insulin and a daily dose of gastrointestinal hormone.

In an embodiment, the compositions according to the invention comprise from 40 U/mL to 500 U/mL of basal insulin of which the isoelectric point is from 5.8 to 8.5, and from 0.05 to 0.5 mg/mL of exenatide.

In an embodiment, the compositions according to the invention comprise from 40 U/mL to 500 U/mL of basal insulin of which the isoelectric point is from 5.8 to 8.5, and from 1 to 10 mg/mL of liraglutide.

In an embodiment, the compositions according to the invention comprise from 40 U/mL to 500 U/mL of basal insulin of which the isoelectric point is from 5.8 to 8.5, and from 0.01 to 1 mg/mL of lixisenatide.

In an embodiment, the compositions according to the invention comprise from 40 U/mL to 500 U/mL of basal insulin of which the isoelectric point is from 5.8 to 8.5, and from 5 to 100 mg/mL of albiglutide.

In an embodiment, the compositions according to the invention comprise from 40 U/mL to 500 U/mL of basal insulin of which the isoelectric point is from 5.8 to 8.5, and from 0.1 to 10 mg/mL/of dulaglutide.

In an embodiment, the compositions according to the invention comprise 500 U/mL of basal insulin of which the isoelectric point is from 5.8 to 8.5, and from 0.04 to 0.5 mg/mL of exenatide.

In an embodiment, the compositions according to the invention comprise 500 U/mL of basal insulin of which the isoelectric point is from 5.8 to 8.5, and from 1 to 10 mg/mL of liraglutide.

In an embodiment, the compositions according to the invention comprise 500 U/mL of basal insulin of which the isoelectric point is from 5.8 to 8.5, and from 0.01 to 1 mg/mL of lixisenatide.

In an embodiment, the compositions according to the invention comprise 500 U/mL of basal insulin of which the isoelectric point is from 5.8 to 8.5, and from 5 to 100 mg/mL of albiglutide.

In an embodiment, the compositions according to the invention comprise 500 U/mL of basal insulin of which the isoelectric point is from 5.8 to 8.5, and from 0.1 to 10 mg/mL of dulaglutide.

In an embodiment, the compositions according to the invention comprise 400 U/mL of basal insulin of which the isoelectric point is from 5.8 to 8.5, and from 0.04 to 0.5 mg/mL of exenatide.

In an embodiment, the compositions according to the invention comprise 400 U/mL of basal insulin of which the isoelectric point is from 5.8 to 8.5, and from 1 to 10 mg/mL of liraglutide.

In an embodiment, the compositions according to the invention comprise 400 U/mL of basal insulin of which the isoelectric point is from 5.8 to 8.5, and from 0.01 to 1 mg/mL of lixisenatide.

In an embodiment, the compositions according to the invention comprise 400 U/mL of basal insulin of which the isoelectric point is from 5.8 to 8.5, and from 5 to 100 mg/mL of albiglutide.

In an embodiment, the compositions according to the invention comprise 400 U/mL of basal insulin of which the isoelectric point is from 5.8 to 8.5, and from 0.1 to 10 mg/mL of dulaglutide.

In an embodiment, the compositions according to the invention comprise 300 U/mL of basal insulin of which the isoelectric point is from 5.8 to 8.5, and from 0.04 to 0.5 mg/mL of exenatide.

In an embodiment, the compositions according to the invention comprise 300 U/mL of basal insulin of which the isoelectric point is from 5.8 to 8.5, and from 1 to 10 mg/mL of liraglutide.

In an embodiment, the compositions according to the invention comprise 300 U/mL of basal insulin of which the isoelectric point is from 5.8 to 8.5, and from 0.01 to 1 mg/mL of lixisenatide.

In an embodiment, the compositions according to the invention comprise 300 U/mL of basal insulin of which the isoelectric point is from 5.8 to 8.5, and from 5 to 100 mg/mL of albiglutide.

In an embodiment, the compositions according to the invention comprise 300 U/mL of basal insulin of which the isoelectric point is from 5.8 to 8.5, and from 0.1 to 10 mg/mL of dulaglutide.

In an embodiment, the compositions according to the invention comprise 225 U/mL of basal insulin of which the isoelectric point is from 5.8 to 8.5, and from 0.04 to 0.5 mg/mL of exenatide.

In an embodiment, the compositions according to the invention comprise 225 U/mL of basal insulin of which the isoelectric point is from 5.8 to 8.5, and from 1 to 10 mg/mL of liraglutide.

In an embodiment, the compositions according to the invention comprise 225 U/mL of basal insulin of which the isoelectric point is from 5.8 to 8.5, and from 0.01 to 1 mg/mL of lixisenatide.

In an embodiment, the compositions according to the invention comprise 225 U/mL of basal insulin of which the isoelectric point is from 5.8 to 8.5, and from 5 to 100 mg/mL of albiglutide.

In an embodiment, the compositions according to the invention comprise 225 U/mL of basal insulin of which the isoelectric point is from 5.8 to 8.5, and from 0.1 to 10 mg/mL of dulaglutide.

In an embodiment, the compositions according to the invention comprise 200 U/mL of basal insulin of which the isoelectric point is from 5.8 to 8.5, and from 0.04 to 0.5 mg/mL of exenatide.

In an embodiment, the compositions according to the invention comprise 200 U/mL of basal insulin of which the isoelectric point is from 5.8 to 8.5, and from 1 to 10 mg/mL of liraglutide.

In an embodiment, the compositions according to the invention comprise 200 U/mL of basal insulin of which the isoelectric point is from 5.8 to 8.5, and from 0.01 to 1 mg/mL of lixisenatide.

In an embodiment, the compositions according to the invention comprise 200 U/mL of basal insulin of which the isoelectric point is from 5.8 to 8.5, and from 5 to 100 mg/mL, of albiglutide.

In an embodiment, the compositions according to the invention comprise 200 U/mL of basal insulin of which the isoelectric point is from 5.8 to 8.5, and from 0.1 to 10 mg/mL of dulaglutide.

In an embodiment, the compositions according to the invention comprise 100 U/mL (or approximately 3.6 mg/mL) of basal insulin of which the isoelectric point is from 5.8 to 8.5, and from 0.04 to 0.5 mg/mL of exenatide.

In an embodiment, the compositions according to the invention comprise 100 U/mL (or approximately 3.6 mg/mL) of basal insulin of which the isoelectric point is from 5.8 to 8.5, and from 1 to 10 mg/mL of liraglutide.

In an embodiment, the compositions according to the invention comprise 100 U/mL (or approximately 3.6 mg/mL) of basal insulin of which the isoelectric point is from 5.8 to 8.5, and from 0.01 to 1 mg/mL of lixisenatide.

In an embodiment, the compositions according to the invention comprise 100 U/mL of basal insulin of which the isoelectric point is from 5.8 to 8.5, and from 5 to 100 mg/mL of albiglutide.

In an embodiment, the compositions according to the invention comprise 100 U/mL of basal insulin of which the isoelectric point is from 5.8 to 8.5, and from 0.1 to 10 mg/mL of dulaglutide.

In an embodiment, the compositions according to the invention comprise 40 U/mL of basal insulin of which the isoelectric point is from 5.8 to 8.5, and from 0.04 to 0.5 mg/mL of exenatide.

In an embodiment, the compositions according to the invention comprise 40 U/mL of basal insulin of which the isoelectric point is from 5.8 to 8.5, and from 1 to 10 mg/mL of liraglutide.

In an embodiment, the compositions according to the invention comprise 40 U/mL of basal insulin of which the isoelectric point is from 5.8 to 8.5, and from 0.01 to 1 mg/mL of lixisenatide.

In an embodiment, the compositions according to the invention comprise 40 U/mL of basal insulin of which the isoelectric point is from 5.8 to 8.5, and from 5 to 100 mg/mL of albiglutide.

In an embodiment, the compositions according to the invention comprise 40 U/mL of basal insulin of which the isoelectric point is from 5.8 to 8.5, and from 0.1 to 10 mg/mL of dulaglutide.

In an embodiment, the compositions according to the invention furthermore comprise zinc salts at a concentration from 0 to 5000 µM.

In an embodiment, the compositions according to the invention furthermore comprise zinc salts at a concentration from 0 to 4000 µM.

In an embodiment, the compositions according to the invention furthermore comprise zinc salts at a concentration from 0 to 3000 µM.

In an embodiment, the compositions according to the invention furthermore comprise zinc salts at a concentration from 0 to 2000 µM.

In an embodiment, the compositions according to the invention furthermore comprise zinc salts at a concentration from 0 to 1000 µM.

In an embodiment, the compositions according to the invention furthermore comprise zinc salts at a concentration from 50 to 600 µM.

In an embodiment, the compositions according to the invention furthermore comprise zinc salts at a concentration from 100 to 500 µM.

In an embodiment, the compositions according to the invention furthermore comprise zinc salts at a concentration from 200 to 500 µM.

In an embodiment, the compositions according to the invention furthermore comprise buffers.

In an embodiment, the compositions according to the invention comprise buffers at concentrations from 0 to 100 mM.

In an embodiment, the compositions according to the invention comprise buffers at concentrations from 15 to 50 mM.

In an embodiment, the compositions according to the invention comprise a buffer selected from the group consisting of a phosphate buffer, tris (trishydroxymethylaminomethane) and sodium citrate.

In an embodiment, the buffer is sodium phosphate.

In an embodiment, the buffer is tris (trishydroxymethylaminomethane).

In an embodiment, the buffer is sodium citrate.

In an embodiment, the compositions according to the invention furthermore comprise preservatives.

In an embodiment, the preservatives are selected from the group consisting of m-cresol and phenol, alone or in a mixture.

In an embodiment, the concentration of preservatives is from 10 to 50 mM.

In an embodiment, the concentration of preservatives is from 10 to 40 mM.

In an embodiment, the compositions according to the invention furthermore comprise a surfactant.

In an embodiment, the surfactant is selected from the group consisting of propylene glycol and polysorbate.

The compositions according to the invention can furthermore comprise additives such as tonicity agents.

In an embodiment, the tonicity agents are selected from the group consisting of glycerol, sodium chloride, mannitol and glycine.

The compositions according to the invention can comprise, in addition, all the excipients in conformity with the pharmacopoeias and compatible with the insulins used at the conventional concentrations.

The invention also relates to a pharmaceutical formulation according to the invention, characterized in that it is obtained by drying and/or lyophilization.

In the case of local and systemic releases, the modes of administration considered are by intravenous, subcutaneous, intradermal or intramuscular route.

The transdermal, oral, nasal, vaginal, ocular, buccal, pulmonary routes of administration are also considered.

The invention also relates to single-dose formulations at a pH from 6.0 to 8.0, comprising a basal insulin of which the isoelectric point is from 5.8 to 8.5, and a prandial insulin.

The invention also relates to single-dose formulations at a pH from 6.0 to 8.0, comprising a basal insulin of which the isoelectric point is from 5.8 to 8.5, and a gastrointestinal hormone as defined above.

The invention also relates to single-dose formulations at a pH from 6.0 to 8.0, comprising a basal insulin of which the isoelectric point is from 5.8 to 8.5, a prandial insulin, and a gastrointestinal hormone as defined above.

The invention also relates to single-dose formulations at a pH from 6.6 to 7.8, comprising a basal insulin of which the isoelectric point is from 5.8 to 8.5, and a prandial insulin.

The invention also relates to single-dose formulations at a pH from 6.6 to 7.8, comprising a basal insulin of which the isoelectric point is from 5.8 to 8.5, and a gastrointestinal hormone as defined above.

The invention also relates to single-dose formulations at a pH from 6.6 to 7.8, comprising a basal insulin of which the isoelectric point is from 5.8 to 8.5, a prandial insulin, and a gastrointestinal hormone as defined above.

The invention also relates to single-dose formulations at a pH from 6.6 to 7.6, comprising a basal insulin of which the isoelectric point is from 5.8 to 8.5, and a prandial insulin.

The invention also relates to single-dose formulations at a pH from 6.6 to 7.6, comprising a basal insulin of which the isoelectric point is from 5.8 to 8.5, and a gastrointestinal hormone as defined above.

The invention also relates to single-dose formulations at a pH from 6.6 to 7.6, comprising a basal insulin of which the isoelectric point is from 5.8 to 8.5, a prandial insulin, and a gastrointestinal hormone as defined above.

In an embodiment, the single-dose formulations comprise, in addition, a co-polyamino acid as defined above.

In an embodiment, the formulations are in the form of an injectable solution.

In an embodiment, the basal insulin of which the isoelectric point is from 5.8 to 8.5, is insulin glargine.

In an embodiment, the prandial insulin is human insulin.

In an embodiment, the insulin is a recombinant human insulin as described in the European Pharmacopoeia and the American Pharmacopoeia.

In an embodiment, the prandial insulin is selected from the group comprising insulin lispro (Humalog®), insulin glulisine (Apidra®) and insulin aspart (NovoLog®).

In an embodiment, the prandial insulin is insulin lispro.

In an embodiment, the prandial insulin is insulin glulisine.

In an embodiment, the prandial insulin is insulin aspart.

In an embodiment, the GLP-1 RA, the GLP-1 RA analog or derivative is selected from the group comprising exenatide (Byetta®), liraglutide (Victoza®), lixisenatide (Lyxumia®), albiglutide (Tanzeum®), dulaglutide (Trulicity®), or one of the derivatives thereof.

In an embodiment, the gastrointestinal hormone is exenatide.

In an embodiment, the gastrointestinal hormone is liraglutide.

In an embodiment, the gastrointestinal hormone is lixisenatide.

In an embodiment, the gastrointestinal hormone is albiglutide.

In an embodiment, the gastrointestinal hormone is dulaglutide.

The solubilization at a pH from 6.0 to 8.0 of the basal insulins, the isoelectric point of which is from 5.8 to 8.5, by the co-polyamino acids bearing carboxylate charges and at least one hydrophobic radical according to the invention can be observed and controlled simply with the naked eye thanks to a change in the appearance of the solution.

The solubilization at a pH from 6.6 to 7.8 of the basal insulins, the isoelectric point of which is from 5.8 to 8.5, by the co-polyamino acids bearing carboxylate charges and at least one hydrophobic radical according to the invention can be observed and controlled simply with the naked eye thanks to a change in the appearance of the solution.

Moreover and as importantly, the applicant was able to verify that a basal insulin of which the isoelectric point is from 5.8 to 8.5, solubilized at a pH from 6.0 to 8.0 in the presence of a co-polyamino acid bearing carboxylate charges and at least one hydrophobic radical according to the invention maintains its slow insulin action whether alone or in combination with a prandial insulin or a gastrointestinal hormone.

The applicant was also able to verify that a prandial insulin mixed at a pH from 6.0 to 8.0 in the presence of a co-polyamino acid bearing carboxylate charges and at least one hydrophobic radical according to the invention and of a basal insulin of which the isoelectric point is from 5.8 to 8.5 maintains its rapid insulin action.

The preparation of a composition according to the invention has the advantage that it can be carried out by simply mixing an aqueous solution of basal insulin of which the isoelectric point is from 5.8 to 8.5, and a co-polyamino acid bearing carboxylate charges and at least one hydrophobic radical according to the invention, in aqueous solution or in lyophilized form. If necessary, the pH of the preparation is adjusted to a pH from 6 to 8.

The preparation of a composition according to the invention has the advantage that it can be carried out by simply mixing an aqueous solution of basal insulin of which the isoelectric point is from 5.8 to 8.5, a solution of prandial insulin, and a co-polyamino acid bearing carboxylate charges and at least one hydrophobic radical according to the invention, in aqueous solution or in lyophilized form. If necessary, the pH of the preparation is adjusted to a pH from 6 to 8.

The preparation of a composition according to the invention has the advantage that it can be carried out by simply mixing an aqueous solution of basal insulin of which the isoelectric point is from 5.8 to 8.5, a solution of GLP-1 RA, a GLP-1 RA analog or derivative, and a co-polyamino acid bearing carboxylate charges and at least one hydrophobic radical according to the invention, in aqueous solution or in lyophilized form. If necessary, the pH of the preparation is adjusted to a pH from 6 to 8.

The preparation of a composition according to the invention has the advantage that it can be carried out by simply mixing an aqueous solution of basal insulin of which the isoelectric point is from 5.8 to 8.5, a solution of prandial insulin, a solution of GLP-1 RA, a GLP-1 RA analog or derivative, and a co-polyamino acid bearing carboxylate charges and at least one hydrophobic radical according to the invention, in aqueous solution or in lyophilized form. If necessary, the pH of the preparation is adjusted to a pH from 6 to 8.

In an embodiment, the mixture of basal insulin and co-polyamide is concentrated by ultrafiltration before the mixing with prandial insulin in aqueous solution or in lyophilized form.

If necessary, the composition of the mixture is adjusted with excipients such as glycerol, m-cresol, zinc chloride and polysorbate (Tween®) by adding concentration solution of these excipients within the mixture. If necessary, the pH of the preparation is adjusted to a pH from 6 to 8.

FIG. 1: Mean curves of deviation of the basal insulin level±standard deviation from the mean for the simultaneous administrations of insulin lispro (Humalog®) (100 U/mL, 0.20 IU/kg) (filled circles) and of insulin glargine (Lantus®) (100 U/mL, 0.60 U/kg), in comparison with the administration of a composition according to the invention described in Example CB3j (266 U/mL, 0.8 U/kg) (empty squares); the administrations having been carried out on dogs (n=10), by subcutaneous injection. (on the abscissa, the post-injection times, and on the ordinate, the delta concentration of insulin in pmol/L).

Figure 2:
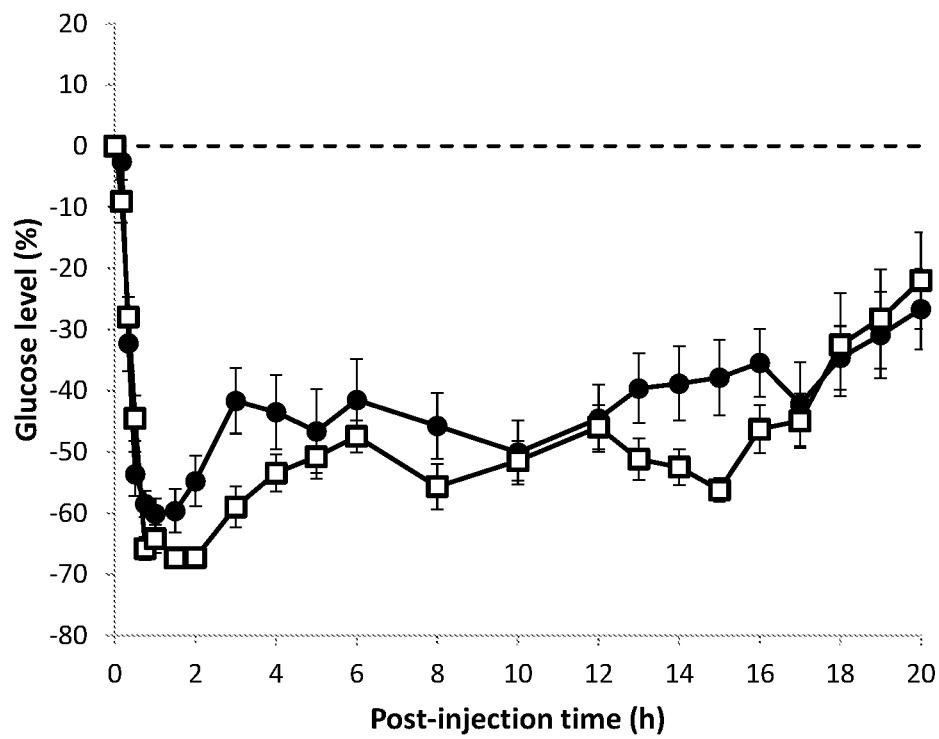

FIG. 2: Mean curves of glycemia±standard deviation from the mean for the simultaneous administrations of insulin lispro (Humalog®) (100 U/mL, 0.20 IU/kg) and of insulin glargine (Lantus®) (100 U/mL, 0.60 U/kg) (filled circles) in comparison with the administration of a composition according to the invention described in Example CB3j (266 U/mL, 0.8 U/kg) (empty squares); the administrations having been carried out on dogs (n=10), by subcutaneous injection. (on the abscissa, the post-injection time, and on the ordinate, the glucose level in percentage)

Figure 3:
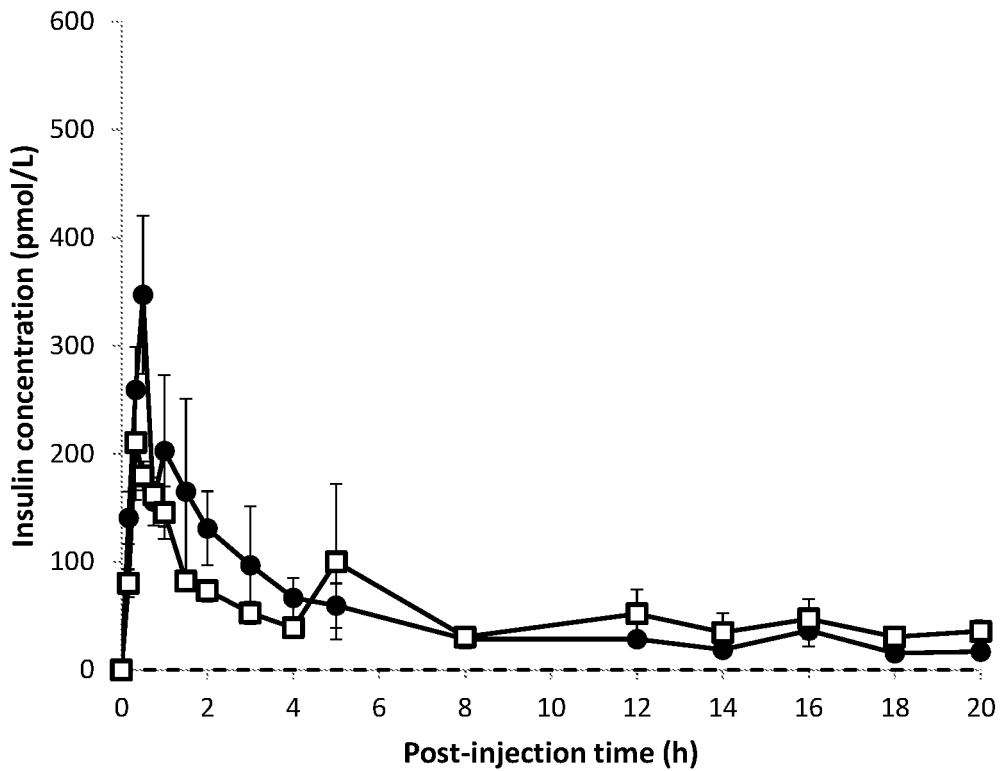

FIG. 3: Mean curves of deviation of the basal level of insulin t standard deviation from the mean for the simultaneous administrations of insulin lispro (Humalog®) (100 U/mL, 0.20 IU/kg) and of insulin glargine (Lantus®) (100 U/mL, 0.60 U/kg) (full circles) in comparison with the administration of a composition according to the invention (empty squares) described in Example CB3o (266 U/mL, 0.8 U/kg); the administrations having been carried out on dogs (n=10), by subcutaneous injection. (on the abscissa, the post-injection time, and on the ordinate, the delta concentration of insulin in pmol/L)

Figure 4:
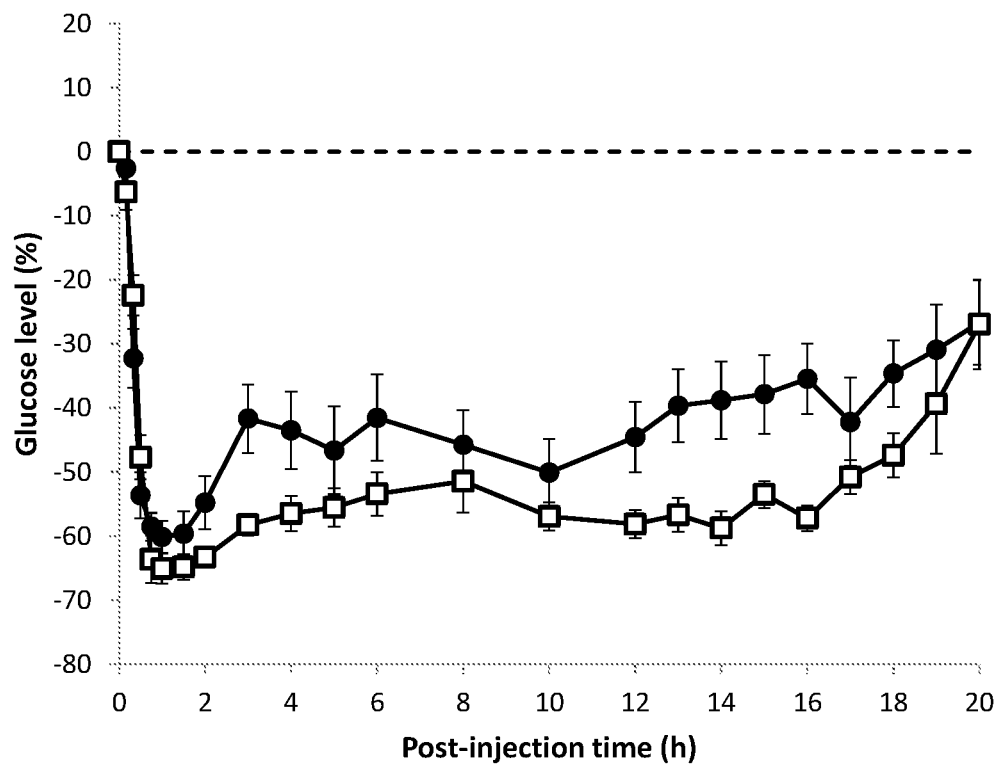

FIG. 4: Mean curves of glycemia±standard deviation from the mean for the simultaneous administrations of insulin lispro (Humalog®) (100 U/mL, 0.20 IU/kg) and of insulin glargine (Lantus®) (100 U/mL, 0.60 U/kg) (full circles) in comparison with the administration of a composition according to the invention (empty squares) described in Example CB3o (266 U/mL, 0.8 U/kg); the administrations having been carried out on dogs (n=10), by subcutaneous injection. (on the abscissa, the post-injection time, and on the ordinate, the glucose level in percentage)

Figure 5:
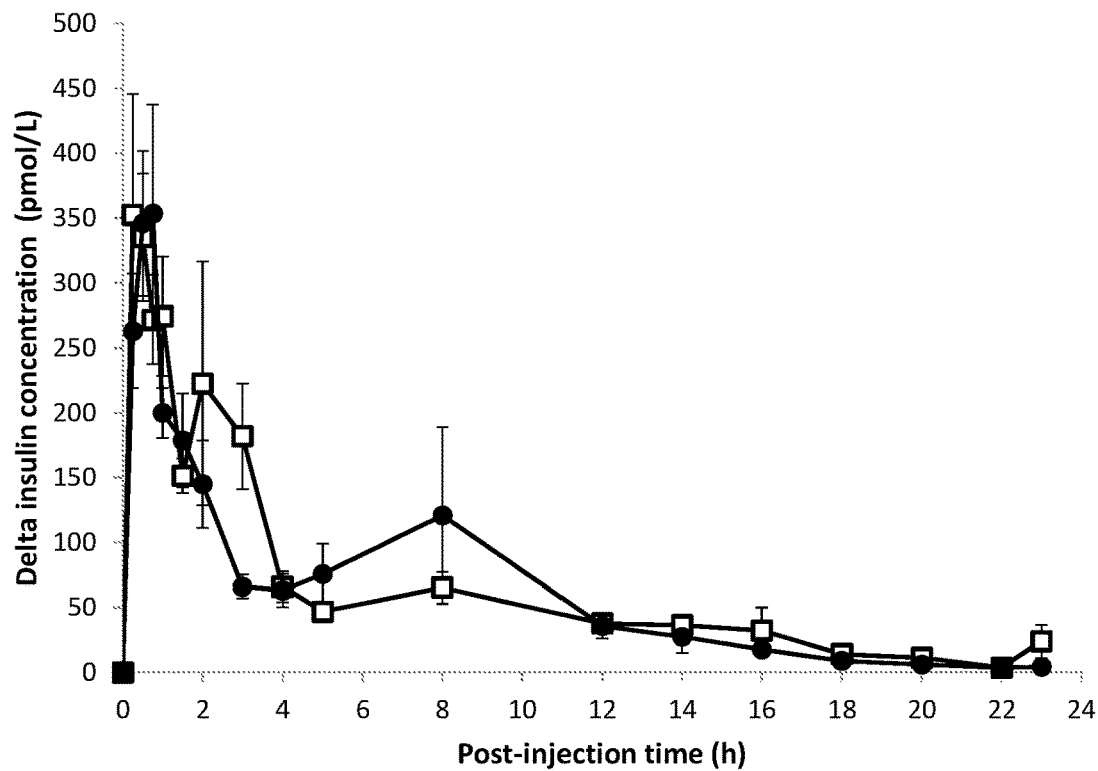

FIG. 5: Mean curves of deviation of the basal insulin level±standard deviation from the mean after the administration of composition CB2a (266 U/mL, 0.67 U/kg of insulin) (full circles) and of composition CB2c (266 U/mL, 0.67 U/kg of insulin, 0.125 µg/kg of exenatide) (empty squares); the administrations having been carried out on dogs (n=10), by subcutaneous injection. (on the abscissa, the post-injection time, and on the ordinate, the delta concentration of insulin in pmol/L)

Figure 6:
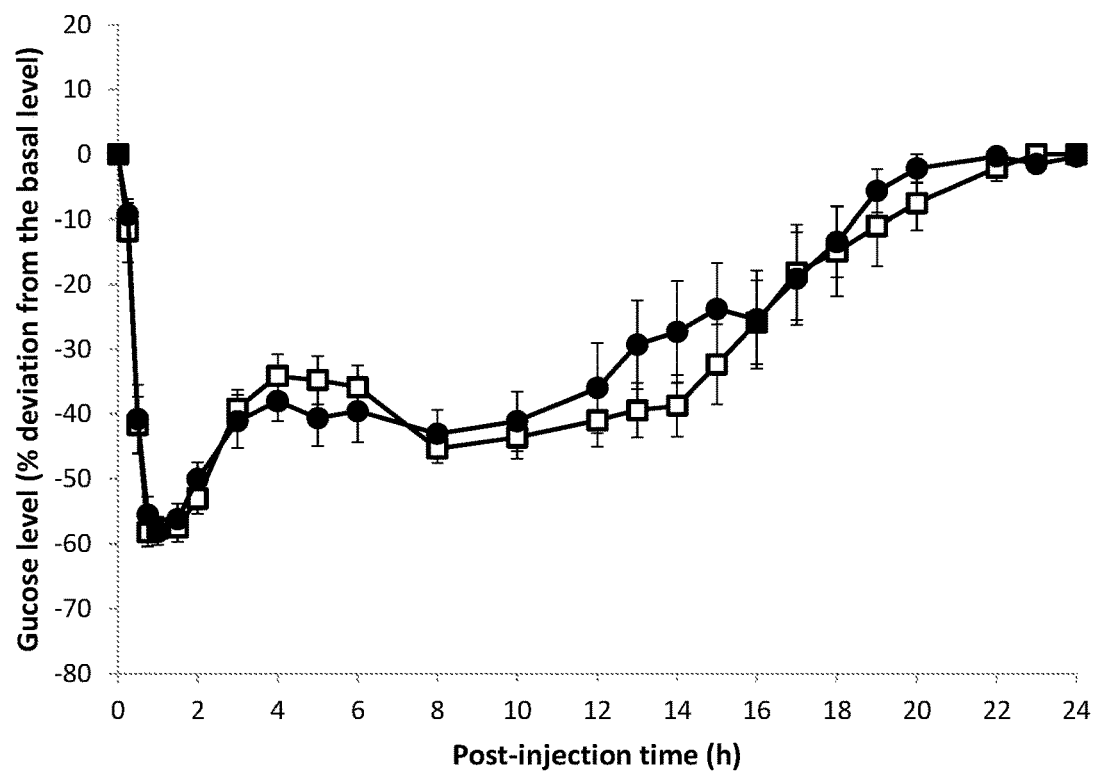

FIG. 6: Mean curves of glycemia in percentage of deviation of the basal level±standard deviation from the mean after the administration of composition CB2a (266 U/mL, 0.67 U/kg of insulin) (full circles) and of composition CB2c (266 U/mL, 0.67 U/kg of insulin, 0.125 µg/kg of exenatide) (empty squares); the administrations having been carried out on dogs (n=10), by subcutaneous injection. (on the abscissa, the post-injection time, and on the ordinate, the glucose level in percentage of deviation from the basal level)

Figure 7:
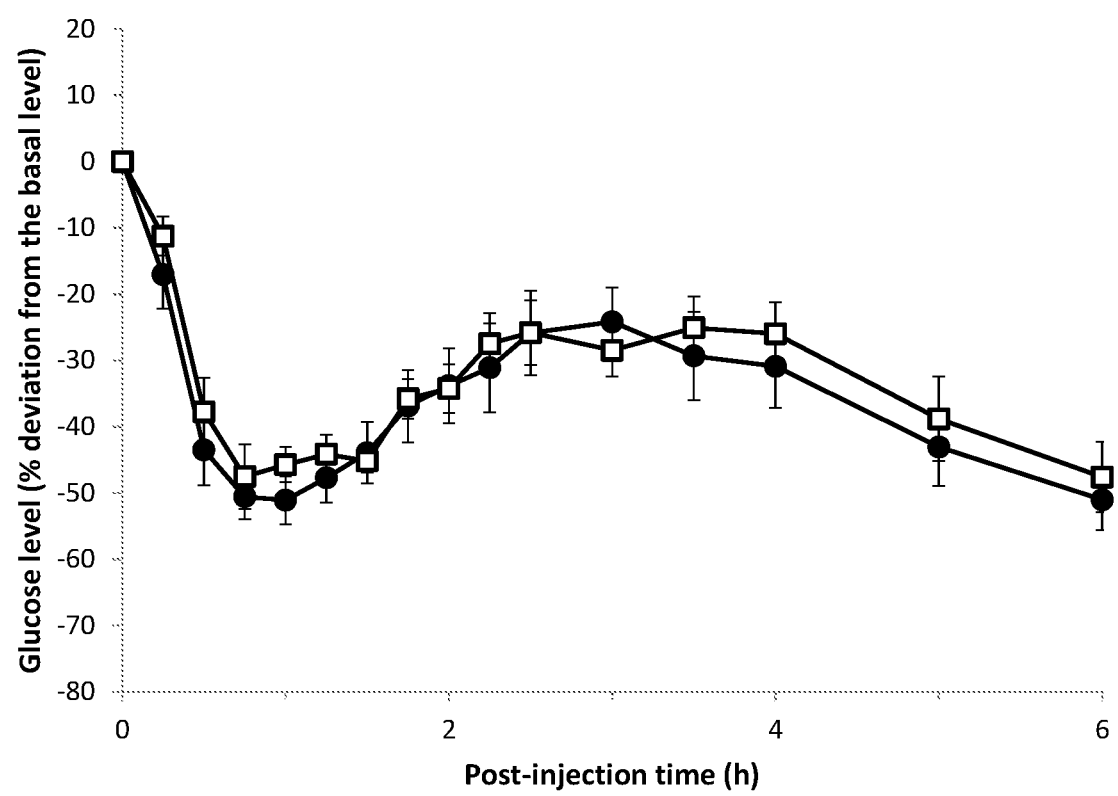

FIG. 7: Mean curves of glycemia in percentage of deviation from the basal level±standard deviation from the mean after the administration of composition CB2c (266 U/mL, 1 U/kg of insulin and 0.19 µg/kg of exenatide) (empty circles) and separate and simultaneous administrations of insulin lispro (Humalog®) (100 U/mL, 0.25 U/kg), of insulin glargine (Lantus®) (100 U/mL, 0.75 U/kg) and of exenatide (Byetta®) (0.25 mg/mL, 0.19 µg/kg) (full circles); the administrations having been carried out on dogs (n=10), by subcutaneous injection. (on the abscissa, the post-injection time, and on the ordinate, the glucose level in percentage of deviation from the basal level)

EXAMPLES

The invention is described in greater detail in reference to the following examples in a non-limiting manner.

Part A

AA: Synthesis of the hydrophobic molecules in which p=1

The radicals are represented in the following Table 1a by the corresponding hydrophobic molecule before grafting onto the co-polyamino acid.

TABLE 1a list and structure of the hydrophobic molecules synthesized according to the invention.

| No. | Structure of the hydrophobic molecule before grafting onto the co-polyamino acids |
|---|---|
| AA4 | H₂N~~O~~O~~O~~NH—C(=O)—[proline]—C(=O)—C₁₅H₃₁ |
| AA7 | H₂N~~O~~O~~O~~NH—C(=O)—[proline]—C(=O)—C₁₉H₃₉ |

Example AA4: Molecule AA4

Molecule A1: Product Obtained by the Reaction Between the Palmitoyl Chloride and L-Proline A solution of palmitoyl chloride (23.0 g, 83.7 mmol) in acetone (167 mL) is added dropwise within 90 minutes to a solution of L-proline (10.6 g, 92.1 mmol) in a 1 N aqueous sodium hydroxide solution (230 mL; 230 mmol). After 14 h of stirring at room temperature, the heterogeneous mixture is cooled to 0° C., then filtered through a sintered filter to yield a white solid which is washed with water (2×100 mL), then with diisopropyl ether (100 mL). The solid is dried at reduced pressure. The solid is then dissolved at reflux in 200 mL of water, then 8 mL of a 37% hydrochloric acid solution are added until obtaining a pH of 1. The opalescent reaction medium is then cooled to 0° C. The precipitate obtained is filtered through a sintered filter, then washed with water (5×50 mL) until filtrates of neutral pH are obtained, then it is dried overnight at 50° C. in an oven under a vacuum. The product is purified by recrystallization in diisopropyl ether. A white solid is obtained.

Yield: 22.7 g (77%).

$^1$H NMR (CDCl3, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H) 6.60-8.60 (1H).

Molecule A2: Product Obtained by the Reaction Between Molecule A1 and Boc-1-amino-4,7,10-trioxa-13-tridecaneamine N,N-diisopropylethylamine (DIPEA) (4.1 g, 31.8 mmol), 1-hydroxybenzotriazole (HOBt) (2.2 g, 16.4 mmol), then N-(3-dimethylaminopropyl)-N'-ethylcarbodiimide (EDC) (3.2 g, 16.6 mmol) are added successively at room temperature to a solution of molecule A1 (4.5 g, 12.7 mmol) in 90 mL of chloroform. After 15 minutes of stirring at room temperature, a solution of Boc-1-amino-4,7,10-trioxa-13-tridecaneamine (4.5 g, 14.0 mmol) in 5 mL of chloroform is added. After 18 h of stirring at room temperature, a 0.1 N HCl solution (100 mL), then a saturated NaCl solution (50 mL) are added. The phases are separated, then the organic phase is washed successively with a 0.1 N HCl solution/saturated NaCl solution (100 mL/50 mL), a saturated NaCl solution (100 mL), a saturated NaHCO₃ solution (100 mL), then a saturated NaCl solution (100 mL). The organic phase is dried over anhydrous sodium sulfate, filtered then concentrated at reduced pressure. A yellow oil is obtained after purification by flash chromatograph (methanol, dichloromethane).

Yield: 7.7 g (92%).

$^1$H NMR (CDCl₃, ppm): 0.88 (3H); 1.22-1.37 (24H); 1.44 (9H); 1.59-1.67 (2H); 1.67-2.00 (6H); 2.06-2.45 (4H); 3.18-3.76 (18H); 4.28 (0.2H); 4.52 (0.8H); 4.69-5.04 (1H); 6.77 (0.2H); 7.20 (0.8H).

Molecule AA4

At 0° C. a 4 M hydrochloric acid solution in dioxane (29.5 mL, 118 mmol) is added dropwise to a solution of molecule A2 (7.7 g, 11.8 mmol) in 90 mL of dichloromethane. After 3 h 30 of stirring at room temperature, the solution is concentrated at reduced pressure. The residue is purified by flash chromatography (methanol, dichloromethane) to yield a yellow oil. A co-evaporation with diisopropyl ether and drying at 50° C. under a vacuum make it possible to obtain molecule AA4 in hydrochloride salt form.

Yield: 5.4 g (76%).

$^1$H NMR (CDCl₃, ppm): 0.88 (3H); 1.08-1.40 (24H); 1.49-1.65 (2H); 1.76-2.39 (10H); 3.07-3.28 (3H); 3.34-3.80 (15H); 4.34 (0.05H); 4.64 (0.95H); 7.35 (0.05H); 7.66-8.58 (3.95H).

LC/MS (ESI): 556.7; (calculated ([M+H]$^+$): 556.5).

Example AA7: Molecule AA7

Molecule A3: Product Obtained by Reaction Between Arachidonic Acid and L-Proline Dicyclohexylcarbodiimide (DCC) (10.45 g, 50.6 mmol) and N-hydroxysuccinimide (NHS) (5.83 g, 50.6 mmol) are added successively to an arachidonic acid solution (15.51 g, 49.63 mmol) in THF (500 mL) at 0° C. After 17 h of stirring at room temperature, the medium is cooled to 0° C. for 20 min, filtered through a sintered filter. L-proline (6 g, 52.11 mmol), DIPEA (60.5 mL) and water (50 mL) are added to the filtrate. After 48 h of stirring at room temperature, the mixture is treated with a 1N aqueous HCl solution to pH 1, and the resulting solid is filtered through a sintered filter, washed with water until the pH of the mother liquors is neutral, then dried under a vacuum to yield a yellowish solid. After purification by chromatography on silica gel (cyclohexane, ethyl acetate), a white solid is obtained.

Yield: 10.96 g (54%).

$^1$H NMR (CDCl₃, ppm): 0.88 (3H); 1.28 (34H); 1.66 (2H); 1.95-2.15 (2H); 2.34 (2H); 2.45 (1H); 3.47 (1H); 3.56 (1H); 4.60 (1H).

LC/MS (ESI): 410.4; (calculated ([M+H]$^+$): 410.6).

Molecule A4: Product Obtained by the Reaction Between Molecule A3 and Boc-1-Amino-4,7,10-trioxa-13-tridecane DIPEA (9.32 mL) and 2-(1H-benzotriazol-1-yl)-1,1,3,3-tetramethyluronium tetrafluoroborate (TBTU) (9.45 g, 29.4 mmol) at room temperature are added to a solution of molecule A3 (10.96 g, 26.75 mmol) in THF (135 mL). After 30 min of stirring, Boc-1-amino-4,7,10-trioxa-13-tridecane (10.29 g, 32.11 mmol) is added. After stirring at room temperature for 18 h, the solvent is evaporated at reduced pressure, and the residue is diluted with ethyl acetate (400 mL). The organic phase is washed with a saturated NaHCO$_3$ solution, a 1N aqueous HCl solution, water, an aqueous saturated NaCl solution, then dried over Na$_2$SO$_4$, filtered and concentrated under a vacuum. The residue is purified by flash chromatography (cyclohexane, ethyl acetate, methanol) to yield a colorless oil which solidifies. A solid is obtained.

Yield: 14.2 g (75%).

$^1$H NMR (CDCl$_3$, ppm): 0.88 (3H); 1.24 (32H); 1.43 (9H); 1.57-2.00 (8H); 2.10-2.45 (4H); 3.20-3.75 (18H); 4.30 (0.20H); 4.55 (0.80H); 5.03 (1H); 6.75 (0.20H); 7.20 (0.80H).

LC/MS (ESI): 712.8; (calculated ([M+H]$^+$): 713.1)

Molecule AA7

A 4N HCl solution in dioxane (25 mL) is added to a solution of molecule A4 (14.25 g, 20.01 mmol) in dichloromethane (100 mL) at 0° C. After 20 h of stirring at 0° C. and 4 h of stirring at 25° C., the medium is concentrated under a vacuum. The residue is dissolved four times in methanol and evaporated at reduced pressure to yield a white solid of molecule AA7 in hydrochloride salt form.

Yield: 12.7 g (98%).

$^1$H NMR (DMSO-d$_6$, ppm): 0.85 (3H); 1.23 (32H); 1.45 (2H); 1.64 (2H); 1.70-2.05 (6H); 2.10-2.30 (2H); 2.82 (2H); 3.08 (2H); 3.30-3.60 (14H); 4.15-4.30 (1H); 7.73-8.13 (4H).

LC/MS (ESI): 612.7; (calculated ([M+H]$^+$): 612.9).

AB: Synthesis of the Co-Polyamino Acids

Co-Polyamino Acids with Statistical Grafting (Formula VII or VIIa)

TABLE 1b list of the co-polyamino acids synthesized according to the invention

| No. | co-polyamino acids bearing carboxylate charges and hydrophobic radicals |
|---|---|
| AB6 | 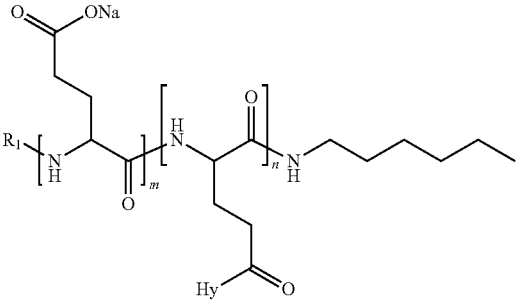<br>$i = 0.025$, DP $(m + n) = 20$<br>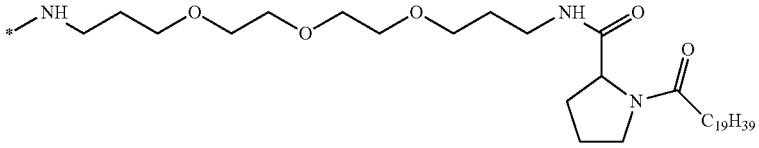<br>Hy =<br>R$_1$ = H or pyroglutamate |
| AB7 | 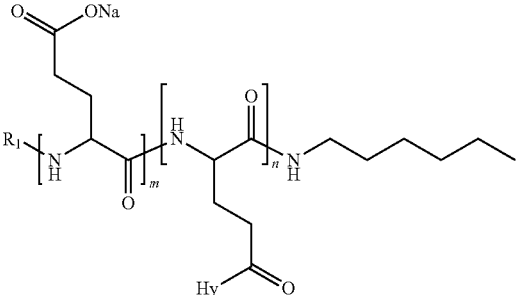<br>$i = 0.03$, DP $(m + n) = 21$ |

TABLE 1b-continued
list of the co-polyamino acids synthesized according to the invention
| No. | co-polyamino acids bearing carboxylate charges and hydrophobic radicals |
|---|---|
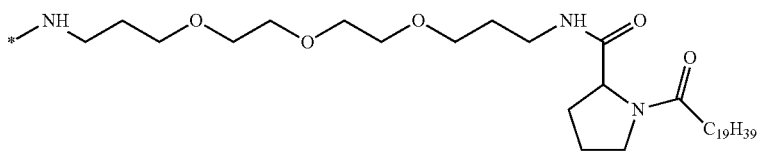
Hy =
R1 = CH₃—C(O)—, H or pyroglutamate
AB8
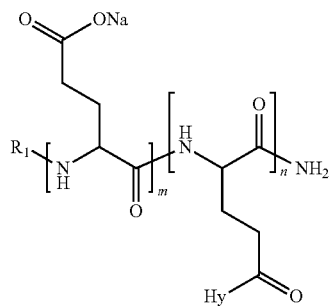
i = 0.03, DP (m + n) = 24
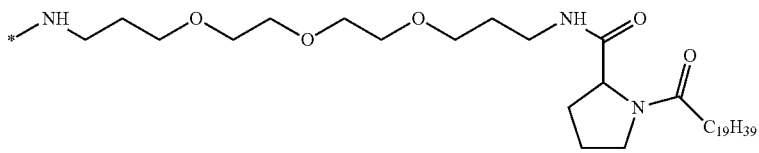
Hy =
R₁ = H or pyroglutamate
AB10
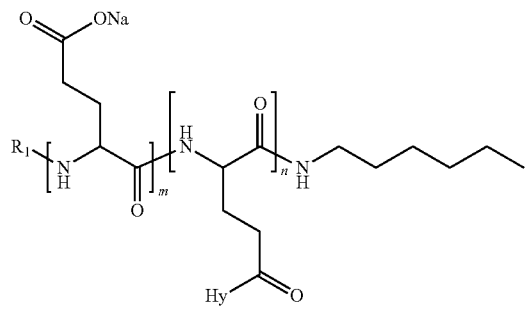
i = 0.08, DP (m + n) = 25
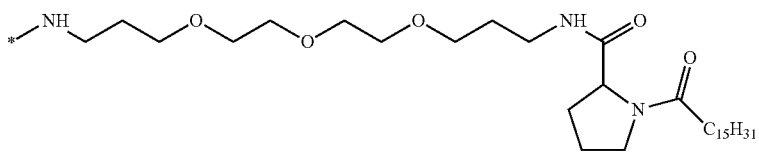
Hy =
R₁ = H or pyroglutamate TABLE 1b-continued list of the co-polyamino acids synthesized according to the invention

| No. | co-polyamino acids bearing carboxylate charges and hydrophobic radicals |
|---|---|
| AB21 | $i = 0.056$, DP $(m + n) = 22$ <br> Hy = (structure shown) <br> $R_1$ = H or pyroglutamate |

Co-Polyamino Acids with Defined Grafting (Formula VII or VIIb)

TABLE 1c list of the co-polyamino acids synthesized according to the invention.

| No. | co-polyamino acids bearing carboxylate charges and hydrophobic radicals |
|---|---|
| AB17 | $i = 0.038$, DP $(m) = 26$ <br> $R_1$ = H or pyroglutamate |
| AB18 | $i = 0.045$, DP $(m) = 22$ <br> $R_1$ = H or pyroglutamate |

Example AB6: Co-Polyamino Acid AB6—Sodium Poly-L-Glutamate Modified by Molecule AA7 and Having a Number Average Molecular Weight (Mn) of 4000 g/Mol Co-Polyamino Acid B1:

poly-L-glutamic acid having a relative number average molecular weight (Mn) of 3500 g/mol originating from the polymerization of γ-benzyl-L-glutamate N-carboxyanhydride initiated by the hexylamine.

In a round-bottom flask dried beforehand in the oven, γ-benzyl-L-glutamate N-carboxyanhydride (89.9 g, 341 mmol) is placed for 30 min under a vacuum, then anhydrous DMF (200 mL) is introduced. The mixture is then stirred under argon until the dissolution is complete, cooled to 4° C., then hexylamine (2.05 mL, 15.5 mmol) is introduced rapidly. The mixture is stirred at between 4° C. and room temperature for 2 days. The reaction mixture is then heated at 65° C. for 2 h, cooled to room temperature, then poured dropwise into diisopropyl ether (3 L) under stirring. The white precipitate is recovered by filtration, washed with diisopropyl ether (2×200 mL), then dried under a vacuum at 30° C. to yield a poly(gamma-benzyl-L-glutamic) acid (PBLG).

A 33% hydrobromic acid (HBr) solution in acetic acid (240 mL, 1.37 mol) is added dropwise to a solution of PBLG (74.8 g) in trifluoroacetic acid (TFA, 340 mL) at 4° C. The mixture is stirred at room temperature for 2 h, then poured dropwise onto a 1:1 (v/v) mixture of diisopropyl ether and water under stirring (4 L). After 2 h of stirring, the heterogeneous mixture is left to rest overnight. The white precipitate is recovered by filtration, washed with a 1:1 (v/v) mixture of diisopropylether and water (340 mL), then with water (340 mL).

The solid obtained is then solubilized in water (1.5 L) by adjusting the pH to 7 by addition of a 10 N aqueous sodium hydroxide solution, then a 1 N aqueous sodium hydroxide solution. After solubilization, the theoretical concentration is adjusted to 20 g/L theoretical by addition of water until obtaining a final volume of 2.1 L.

The solution is filtered through a 0.45-μm filter, then purified by ultrafiltration against a 0.9% NaCl solution, then water until the conductimetry of the permeate is less than 50 μS/cm. The solution of co-polyamino acid is then concentrated until a final volume of 1.8 L is obtained.

The aqueous solution is then acidified by adding 37% hydrochloric acid solution until a pH of 2 is reached. After 4 h of stirring, the precipitate obtained is filtered, washed with water (2×340 mL), then dried under a vacuum at 30° C. to yield a poly-L-glutamic acid having a number average molecular weight (Mn) of 3500 g/mol with respect to a polyoxyethylene (PEG) standard.

Co-Polyamino Acid AB6

The co-polyamino acid AB6-1 having a number average molecular weight (Mn) of 3500 g/mol (10.0 g) is solubilized in DMF (420 mL) at 30° C.-40° C., then maintained at this temperature. In parallel, the hydrochloride salt of molecule AA7 (1.47 g, 2.3 mmol) is suspended in DMF (12 mL), and triethylamine (0.23 g, 2.3 mmol) is added, then the mixture is heated slightly under stirring until the dissolution is complete. NMM (7.6 g, 75 mmol), the solution of AA7, then 2-hydroxypyridine N-oxide (HOPO, 0.84 g, 7.5 mmol) are added successively to the solution of co-polyamino acid in DMF. The reaction medium is then cooled to 0° C., then EDC (1.44 g, 7.5 mmol) is added, and the medium is brought back to room temperature over a period of 2 h. The reaction medium is filtered through a 0.2 mm woven filter and poured dropwise under stirring onto 3.5 L of water containing NaCl at 15% by weight and HCl (pH 2). At the end of the addition, the pH is readjusted to 2 with a 37% HCl solution, and the suspension is allowed to rest overnight. The precipitate is collected by filtration, then rinsed with 100 mL of water. The white solid obtained is solubilized in 500 mL of water by slow addition under stirring of a 1 N aqueous solution NaOH until the pH is 7, then the solution is filtered through a 0.45-μm filter. The clear solution obtained is purified by ultrafiltration against a 0.9% NaCl solution, then water until the conductimetry of the permeate is less than 50 μS/cm. The solution is filtered through a 0.2-μm filter and stored at 2-8° C.

Dry extract: 21.6 mg/g.
DP (estimated based on $^1$H NMR): 20.
Based on $^1$H NMR: i=0.025.
The calculated average molecular weight of the co-polyamino acid AB6 is 3369 g/mol.
HPLC-aqueous SEC (calibrant PEG): Mn=4000 g/mol.

Example AB7: Co-Polyamino Acid AB7—Sodium Poly-L-Glutamate Capped at One of its Ends by an Acetyl Group by Molecule AA7 and Having a Number Average Molecular Weight (Mn) of 3300 g/mol Co-Polyamino Acid AB7-1:

poly-L-glutamic acid having a relative number average molecular weight (Mn) of 3600 mol and a DP of 21 originating from the polymerization of γ-benzyl-L-glutamate N-carboxyanhydride initiated by hexylamine and capped at one of its ends by an acetyl group.

In a round-bottom flask dried beforehand in the oven, γ-benzyl-L-glutamate N-carboxyanhydride (Glu(OBn)-NCA, 100.0 g, 380 mmol) is placed under a vacuum for 30 minutes, then anhydrous DMF (225 mL) is introduced. The mixture is then stirred under argon until the dissolution is complete, cooled to 4° C., then hexylamine (1.78 g, 17 mmol) is introduced rapidly. The mixture is stirred between 4° C. and room temperature for 2 days, then precipitated in diisopropyl ether (3.4 L). The precipitate is recovered by filtration, washed two times with diisopropyl ether (225 mL), then dried to yield a white solid which is dissolved in 450 mL of THF. DIPEA (31 mL, 176 mmol), then acetic anhydride (17 mL, 176 mmol) are added successively to this solution. After one night of stirring at room temperature, the solution is poured slowly into diisopropyl ether (3 L) under stirring. After 1 h of stirring, the precipitate is filtered, washed two times with diisopropyl ether (250 mL), then dried under a vacuum at 30° C. to yield a poly(gamma-benzyl-L-glutamic) acid capped at one of its ends by an acetyl group.

A 33% hydrobromic acid (HBr) solution in acetic acid (235 mL) is added dropwise to a solution of the co-polyamino acid referred to above (72 g) in trifluoroacetic acid (TFA, 335 mL) at 4° C. The mixture is stirred at room temperature for 3 h 30, then poured dropwise onto a 1:1 (v/v) mixture of diisopropyl ether and water under stirring (4 L). After 2 h of stirring, the heterogeneous mixture is allowed to rest overnight. The white precipitate is recovered by filtration, washed with a 1:1 (v/v) mixture of diisopropyl ether and water (340 mL), then with water (340 mL).

The solid obtained is then solubilized in water (1.5 L) by adjusting the pH to 7 by addition of a 10N aqueous sodium hydroxide solution, then a 1N aqueous sodium hydroxide solution. After solubilization, the solution is diluted by addition of water until obtaining a final volume of 2.1 L. The solution is filtered through a 0.45-µm filter, then purified by ultrafiltration against a 0.9% NaCl solution, then water until the conductimetry of the permeate is less than 50 µS/cm. The solution of co-polyamino acid is then concentrated until a final volume of 1.8 L is obtained.

The aqueous solution is then acidified by addition of 37% hydrochloric acid solution until a pH of 2 is reached. After 4 h of stirring, the precipitate obtained is filtered, washed with water (330 mL), then dried under a vacuum at 30° C. to yield a poly-L-glutamic acid having a number average molecular weight (Mn) of 3600 g/mol with respect to a polyoxyethylene standard (PEG), and a mean degree of polymerization of 21.

Co-Polyamino Acid AB7

By a process similar to the one used for the preparation the co-polyamino acid AB6 applied to the hydrochloride salt of molecule AA7 (1.43 g, 2.2 mmol) and to the co-polyamino acid AB7-1 (10.0 g), a poly-L-glutamic acid sodium salt modified by molecule AA7 is obtained.

Dry extract: 24.3 mg/g.
DP (estimated based on $^1$H NMR): 21.
Based on $^1$H NMR: i=0.03.
The calculated average molecular weight of the co-polyamino acid AB7 is 3677 g/mol.
HPLC-aqueous SEC (calibrant PEG): Mn=3300 g/mol.

Example AB8: Co-Polyamino Acid AB8—Sodium Poly-L-Glutamate Modified by Molecule AA7 and Having a Number Average Molecular Weight (Mn) of 3600 g/mol Co-Polyamino Acid AB8-1:

poly-L-glutamic acid having a number average molecular weight (Mn) of 3800 g/mol originating from the polymerization of γ-methyl-L-glutamate N-carboxyanhydride initiated by ammonia.

By a method similar to the one described in the patent application FR-A-2 801 226 applied to γ-methyl-L-glutamic acid N-carboxyanhydride (25.0 g, 133.6 mmol) and to a 0.5 N ammonia solution in dioxane (12.1 mL, 6.05 mmol), a poly-L-glutamic acid is obtained.

Co-Polyamino Acid AB8

By a method similar to the one used for the preparation of the co-polyamino acid AB6 applied to the hydrochloride salt of molecule AA7 (2.1 g, 3.24 mmol) and to the co-polyamino acid AB8-1 (14.3 g), a sodium poly-L-glutamate modified by molecule AA7 is obtained.

Dry extract: 25.2 mg/g.
DP (estimated based on $^1$H NMR): 24.
Based on $^1$H NMR: i=0.03.
The calculated average molecular weight of the co-polyamino acid AB8 is 4099 g/mol.
HPLC-aqueous SEC (calibrant PEG): Mn=3600 g/mol.

Example AB10: Co-Polyamino Acid AB10—Sodium Poly-L-Glutamate Modified by Molecule AA4 and Having a Number Average Molecular Weight (Mn) of 2600 g/mol By a method similar to the one used for the preparation of the co-polyamino acid AB7 applied to the hydrochloride salt of molecule AA4 and to a poly-L-glutamic acid obtained by a method similar to the one used for the preparation of the co-polyamino acid AB6-1, a sodium poly-L-glutamate modified by molecule AA4 is obtained.

Dry extract: 18.3 mg/g.
DP (estimated based on $^1$H NMR): 25.
Based on $^1$H NMR: i=0.08.
The calculated average molecular weight of the co-polyamino acid AB10 is 4870 g/mol.
HPLC-aqueous SEC (calibrant PEG): Mn=2600 g/mol.

Example AB21: Co-Polyamino Acid AB21—Sodium Poly-L-Glutamate Modified by Molecule AA7 and Having a Number Average Molecular Weight (Mn) of 3400 g/mol By a method similar to the one used for the preparation of the co-polyamino acid AB6 applied to the hydrochloride salt of molecule AA7 (2.44 g, 2.4 mmol) and to a poly-L-glutamic acid (10 g) obtained by a method similar to the one used for the preparation of the co-polyamino acid AB6-1, a sodium poly-L-glutamate modified by molecule AA7 is obtained.

Dry extract: 22.7 mg/g.
DP (estimated based on $^1$H NMR): 22.
Based on $^1$H NMR: i=0.056.
The calculated average molecular weight of the co-polyamino acid AB21 is 4090 g/mol.
HPLC-aqueous SEC (calibrant PEG): Mn=3400 g/mol.

Example AB17: Co-Polyamino Acid AB17—Sodium Poly-L-Glutamate Modified at One of its Ends by Molecule AA7 and Having a Number Average Molecular Weight (Mn) of 3500 g/mol The hydrochloride salt of molecule AA7 (2.80 g, 4.32 mmol), chloroform (5 mL), molecular sieve 4 Å (1.3 g) as well as Amberlite IRN 150 ion exchange resin (1.3 g) are introduced successively into an appropriate container. After 1 h of stirring on rollers, the medium is filtered and the resin is rinsed with chloroform. The mixture is evaporated, then co-evaporated with toluene. The residue is solubilized in anhydrous DMF (30 mL) to be used directly in the polymerization reaction.

γ-Benzyl-L-glutamate N-carboxyanhydride (25.0 g, 94.9 mmol) is placed under a vacuum for 30 min in a round-bottom flask dried beforehand in the oven, then anhydrous DMF (140 mL) is introduced. The mixture is stirred under argon until the solubilization is complete, cooled to 4° C., then the solution of molecule AA7 prepared as described above is introduced rapidly. The mixture is stirred between 4° C. and room temperature for 2 days, then heated at 65° C. for 2 h. The reaction mixture is then cooled to room temperature, then poured dropwise in diisopropyl ether (1.7 L) under stirring. The white precipitate is recovered by filtration, washed two times with diisopropyl ether (140 mL), then dried under a vacuum at 30° C. to obtain a white solid. The solid is diluted in TFA (160 mL), and then a 33% hydrobromic acid (HBr) solution in acetic acid (62 mL, 354 mmol) is added dropwise and at 0° C. The solution is stirred for 2 h at room temperature, then poured dropwise onto a 1:1 (v/v) mixture of diisopropyl ether/water and under stirring (1.9 L). After 2 h of stirring, the heterogeneous mixture is allowed to rest overnight. The white precipitate is recovered by filtration, washed successively with a 1:1 (v/v) mixture of diisopropyl ether and water (280 mL), then with water (140 mL). The solid obtained is solubilized in water (530 mL) by adjusting the pH to 7 by adding a 10 N aqueous sodium hydroxide solution, then a 1 N aqueous sodium hydroxide solution. After solubilization, the theoretical concentration is adjusted to 20 g/L theoretical by addition of water until obtaining a final volume of 800 mL. The mixture is filtered through a 0.45-μm filter, then purified by ultrafiltration against a 0.9% NaCl solution, then water until the conductimetry of the permeate is less than 50 μS/cm. The solution of co-polyamino acid is then concentrated to approximately 30 g/L theoretical and the pH is adjusted to 7.0. The aqueous solution is filtered through 0.2 m and stored at 4° C.

Dry extract: 25.2 mg/g.

DP (estimated by $^1$H NMR)=26 therefore i=0.038.

The calculated average molecular weight of the co-polyamino acid AB17 is 4500 g/mol.

HPLC-aqueous SEC (calibrant PEG): Mn=3500 g/mol.

Example AB18: Co-Polyamino Acid AB18—Sodium Poly-L-Glutamate Modified at One of its Ends by Molecule AA7 Having a Number Average Molecular Weight (Mn) of 3700 g/mol A sodium poly-L-glutamate modified at one of its ends by molecule AA7 is obtained by polymerization of γ-methyl-glutamic acid N-carboxyanhydride (25.0 g, 133.6 mmol) using the hydrochloride salt of molecule AA7 (2.80 g. 4.32 mmol) as initiator and carrying out a deprotection of the methyl esters by using a 37% hydrochloric acid solution according to the method described in patent application FR-A-2 801 226.

Dry extract: 44.3 mg/g.

DP (estimated by $^1$H NMR)=22 therefore i=0.045.

The calculated average molecular weight of the co-polyamino acid AB18 is 3896 g/mol.

HPLC-aqueous SEC (calibrant PEG): Mn=3700 g/mol.

Part B: hydrophobic radicals

BB: Synthesis of the hydrophobic molecules in which p=2

The radicals are represented in the following Table 1c' by the corresponding hydrophobic molecule before grafting onto the co-polyamino acid TABLE 1c' list of hydrophobic molecules synthesized according to the invention.

| No. | Structure of the hydrophobic molecule before grafting onto the co-polyamino acid |
|---|---|
| BA1 | 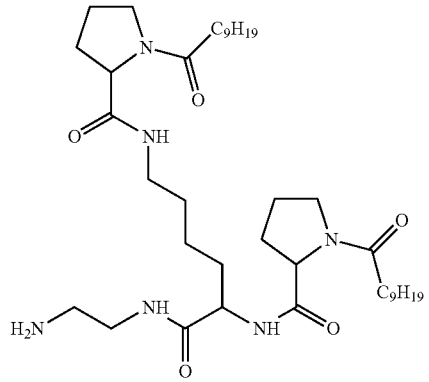 |
| BA2 | 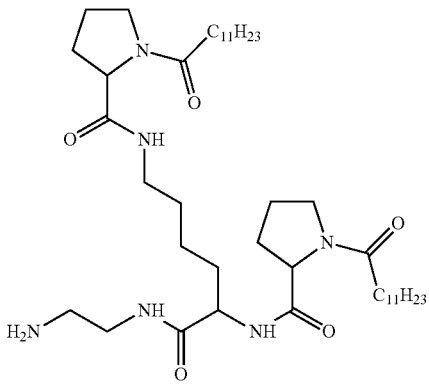 |

TABLE 1c'-continued
list of hydrophobic molecules synthesized according to the invention.
| No. | Structure of the hydrophobic molecule before grafting onto the co-polyamino acid |
|---|---|
| BA3 | 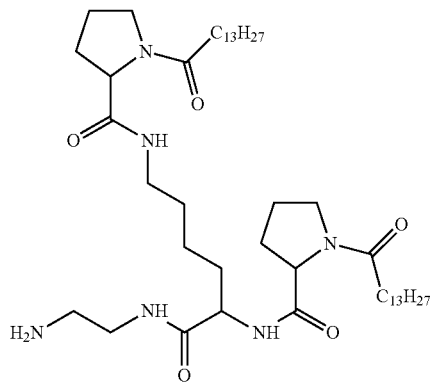 |
| BA4 | 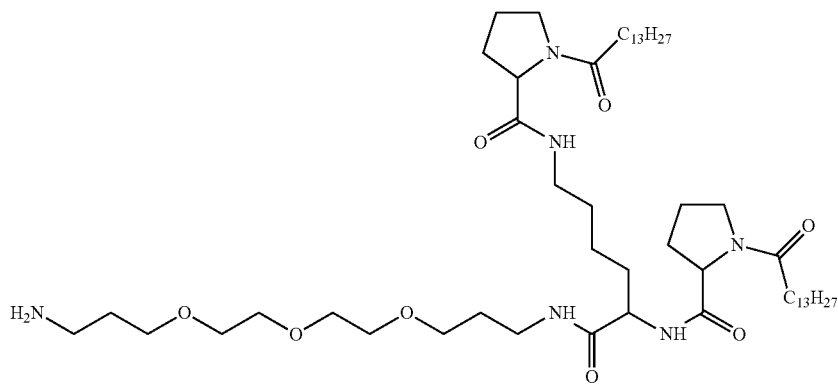 |
| BA5 | 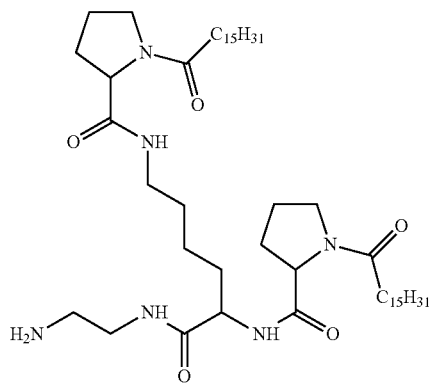 |
| BA6 | 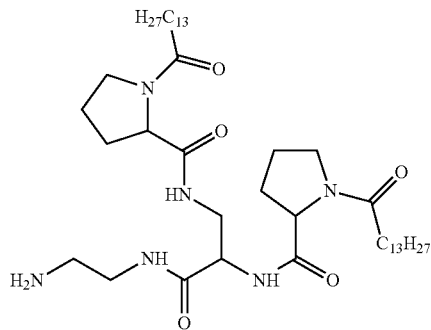 |

TABLE 1c'-continued list of hydrophobic molecules synthesized according to the invention.

| No. | Structure of the hydrophobic molecule before grafting onto the co-polyamino acid |
|---|---|
| BA7 | [chemical structure showing a lysine-based molecule with two prolyl-C13H27 acyl groups and a free H2N-(CH2)- amine terminus] |

Example BA1: Molecule BA1

Molecule B1: Product Obtained by the Reaction Between Decanoic Acid and L-Proline Dicyclohexyl carbodiimide (DCC) (16.29 g, 78.96 mmol) and N-hydroxysuccinimide (NHS) (9.09 g, 78.96 mmol) are added successively to a decanoic acid solution (14.28 g, 82.91 mmol) in THF (520 mL) at 0° C. After 60 h of stirring at room temperature, the mixture is cooled to 0° C. for 20 min, filtered through a sintered filter. L-Proline (10 g, 86.86 mmol), diisopropylethylamine (DIPEA) (68.8 mL) and water (60 mL) are added to the filtrate. After 24 h of stirring at room temperature, the medium is diluted with water (300 mL). The aqueous phase is washed with ethyl acetate (2×250 mL), acidified to pH ~1 with a 1N aqueous HCl solution, then extracted with dichloromethane (3×150 mL). The combined organic phases are dried over $Na_2SO_4$, filtered, concentrated under a vacuum, and the residue is purified by chromatography on silica gel (cyclohexane, ethyl acetate).

Yield: 14.6 g (69%).

$^1$H NMR ($CDCl_3$, ppm): 0.87 (3H); 1.26 (12H); 1.65 (2H); 2.02 (3H); 2.34 (2H); 2.41 (1H); 3.48 (1H); 3.56 (1H); 4.58 (1H)

LC/MS (ESI): 270.2; (calculated ($[M+H]^+$): 270.4).

Molecule B2: Product Obtained by the Reaction Between Molecule B1 and L-Lysine By a method similar to the one used for the preparation of molecule B1 applied to molecule B1 (14.57 g, 54.07 mmol) and to L-lysine (4.15 g, 28.39 mmol), a yellow oil is obtained.

Yield: 16.4 g (93%).

$^1$H NMR ($CDCl_3$, ppm): 0.88 (6H); 1.26 (24H); 1.35-1.65 (8H); 1.85-2.35 (12H); 2.53 (0.2H); 2.90 (0.8H); 3.45-3.75 (5H); 4.50-4.70 (3H); 7.82 (1H).

LC/MS (ESI): 649.6; (calculated ($[M+H]^+$): 649.9).

Molecule B3; Product Obtained by Reaction Between Molecule B2 and Boc-Ethylenediamine DIPEA (8.80 mL) and 2-(1H-benzotriazol-1-yl-1,1,3,3-tetramethyluronium tetrafluoroborate (TBTU, 8.52 g, 26.54 mmol) at room temperature are added to a solution of molecule B2 (16.4 g, 25.27 mmol) in THF (170 mL). After 30 min of stirring, the Boc-ethylenediamine (4.45 g, 27.8 mmol) is added. After stirring at room temperature for 2 h, the solvent is evaporated at reduced pressure and the residue is diluted with ethyl acetate (400 mL). The organic phase is washed with water (250 mL), a saturated aqueous $NaHCO_3$ solution (250 mL), a 1 N aqueous HCl solution (250 mL), a saturated aqueous NaCl solution (250 mL), and dried over $Na_2SO_4$. After filtration and concentration under a vacuum, the residue obtained is purified by chromatography on silica gel (ethyl acetate, methanol) to yield a colorless oil.

Yield: 12.8 g (64%).

$^1$H NMR ($CDCl_3$, ppm): 0.87 (6H); 1.25-1.60 (42H); 1.80-2.05 (4H); 2.15-2.45 (9H); 3.10-3.75 (10H); 4.30 (1H); 4.50 (2H); 5.50 (0.6H); 5.89 (0.2H); 6.15 (0.2H); 7.03 (1H); 7.47 (1H).

LC/MS (ESI): 791.8; (calculated ($[M+H]^+$): 792.1).

Molecule BA1

A 4N HCl solution in dioxane (20.2 mL) is added to a solution of molecule B3 (12.78 g, 16.15 mmol) in dichloromethane (110 mL) at 5° C. After 20 h of stirring at 5° C., the medium is concentrated under a vacuum. The residue obtained is dissolved in methanol and evaporated under a vacuum, this operation being repeated 4 times to yield a white solid of molecule BA1 in hydrochloride salt form.

Yield: 11.4 g (97%).

$^1$H NMR (DMSO-d, ppm): 0.85 (6H); 1.25-1.50 (33H); 1.57 (1H); 1.70-2.40 (12H); 2.82 (2H); 3.00 (2H); 3.25-3.70 (6H); 4.05-4.50 (3H); 7.75-8.45 (6H)

LC/MS (ESI): 691.6; (calculated ($[M+H]^+$): 692.0).

Example BA2: Molecule BA2

Molecule B4; Product Obtained by the Reaction Between Lauric Acid and L-Proline By a method similar to the one used for the preparation of molecule B1 applied to lauric acid (31.83 g, 157.9 mmol) and to L-proline (20 g, 173.7 mmol), a yellow oil is obtained.

Yield: 34.3 g (73%).

$^1$H NMR ($CDCl_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI): 298.2; (calculated ([M+H]$^+$): 298.4).

Molecule B5: Product Obtained by the Reaction Between Molecule B4 and L-Lysine

By a method similar to the one used for the preparation of molecule B1 applied to molecule B4 (33.72 g, 11336 mmol) and to L-lysine (8.70 g, 59.51 mmol), a white solid is obtained.

Yield: 26.2 g (66%).

$^1$H NMR (CDCl$_3$, ppm): 0.88 (6H); 1.26 (32H); 1.35-1.65 (8H); 1.85-2.35 (15H); 2.87 (1H); 3.40-3.75 (5H); 4.50-4.75 (3H); 7.87 (1H).

LC/MS (ESI): 705.6; (calculated ([M+H]$^+$): 706.0).

Molecule B6: Product Obtained by Reaction Between Boc-Ethylenediamine and Molecule B5

By a method similar to the one used for the preparation of molecule B3 applied to molecule B5 (25.74 g, 36.51 mmol) and to Boc-ethylenediamine (6.43 g, 40.16 mmol), a colorless oil is obtained.

Yield: 30.9 g (quantitative).

$^1$H NMR (CDCl$_3$, ppm): 0.88 (6H); 1.35-1.65 (50H); 1.85-2.35 (13H); 3.05-3.75 (10H); 4.25-4.65 (3H); 5.50 (0.4H); 5.88 (0.2H); 6.16 (0.2H); 7.08 (1H); 7.26 (1H); 7.49 (0.2H).

LC/MS (EST): 847.8; (calculated ([M+H]$^+$): 848.2).

Molecule BA2

By a method similar to the one used for the preparation of molecule BA1 applied to molecule B6 (30.9 g, 36.47 mmol), the residue obtained after concentration under a vacuum is dissolved in methanol and evaporated under a vacuum, this operation being repeated 4 times to yield a white solid of molecule BA2 in hydrochloride salt form after drying at reduced pressure.

Yield: 27.65 g (97%).

$^1$H NMR (DMSO-d, ppm): 0.85 (6H); 1.10-2.40 (54H); 2.75-3.15 (4H); 3.25-3.60 (6H); 4.05-4.50 (3H); 7.50-8.50 (6H).

LC/MS (ESI): 747.6; (calculated ([M+H]$^+$): 748.1).

Example BA3: Molecule BA3

Molecule B7: Product Obtained by the Reaction Between Myristic Acid and L-Proline By a method similar to the one used for the preparation of molecule B1 applied to myristic acid (18.93 g, 82.91 mmol) and to L-proline (10 g, 86.86 mmol), a yellowish oil is obtained.

Yield 20 g (78%).

$^1$H NMR (CDCl$_3$, ppm): 0.88 (3H); 1.28 (20H); 1.70 (2H); 1.90-2.10 (3H); 236 (2H); 2.51 (1H); 3.47 (1H); 3.56 (1H); 4.61 (1H)

LC/MS (ESI): 326.2; (calculated ([M+H]J): 326.6).

Molecule B8: Product Obtained by the Reaction Between Molecule B7 and L-Lysine

By a method similar to the one used for the preparation of molecule B1 applied to molecule B7 (20.02 g, 61.5 mmol) and to L-lysine (4.72 g, 32.29 mmol), a white solid is obtained.

Yield: 12.3 g (53%).

$^1$H NMR (DMSO-d$_6$, ppm): 0.85 (6H); 1.26 (40H); 1.35-1.50 (6H); 1.50-2.10 (10H); 2.10-2.25 (4H); 3.01 (2H); 3.31-3.55 (4H); 4.10-4.40 (3H); 7.68 (0.6H); 7.97 (1H); 8.27 (0.4H); 12.50 (1H).

LC/MS (ESI): 761.8; (calculated ([M+H]$^+$): 762.1).

Molecule B9: Product Obtained by the Reaction Between Boc-Ethylenediamine and Molecule B8

By a method similar to the one used for the preparation of molecule B3 applied to molecule B8 (12 g, 15.77 mmol) and to Boc-ethylenediamine (3.03 g, 18.92 mmol), a colorless oil is obtained after purification by chromatography column on silica gel (ethyl acetate, methanol).

Yield: 12.5 g (88%).

$^1$H NMR (DMSO-d$_6$, ppm): 0.85 (6H); 1.20-1.55 (55H); 1.50-2.25 (14H); 2.95-3.10 (6H); 3.31-3.55 (4H); 4.10-4.40 (3H); 6.74 (1H); 7.60-8.25 (3H).

LC/MS (ESI): 904.1; (calculated ([M+H]$^+$): 904.3).

Molecule BA3

After a method similar to the one used for the preparation of molecule BA1 applied to molecule B9 (12.5 g, 13.84 mmol), the residue obtained after concentration under a vacuum is dissolved in methanol and evaporated under a vacuum, this operation being repeated 4 times to yield a white solid of molecule BA3 in hydrochloride salt form after drying at reduced pressure.

Yield: 9.2 g (79%).

$^1$H NMR (DMSO-d, ppm): 0.85 (6H); 1.10-1.65 (48H); 1.70-2.35 (12H); 2.85 (2H); 3.01 (2H); 3.25-3.65 (6H); 4.10-4.50 (3H); 7.70-8.40 (6H).

LC/MS (ESI): 803.9; (calculated ([M+H]$^+$): 804.2).

Example BA4: Molecule BA4

Molecule B10: Product Obtained by the Reaction Between Molecule B8 and Boc-1-amino-4,7,10-trioxa-13-tridecane By a method similar to the one used for the preparation of molecule B3 applied to molecule B8 (29.80 g, 39.15 mmol) and to Boc-1-amino-4,7,10-trioxa-13-tridecane (15.05 g, 49.96 mmol), a thick colorless oil is obtained.

Yield: 25.3 g (61%).

$^1$H NMR (DMSO-d$_6$, ppm): 0.85 (6H); 1.25-2.35 (75H); 2.85-3.20 (6H); 3.25-3.65 (16H); 4.10-4.45 (3H); 6.38 (0.1H); 6.72 (0.9H); 7.50-8.25 (3H).

LC/MS (ESI): 1064.2; (calculated ([M+H]$^+$): 1064.5).

Molecule BA4

After a method similar to the one used for the preparation of molecule BA1 applied to molecule B10 (25.3 g, 23.8 mmol), the residue obtained after concentration under a vacuum is dissolved in methanol and evaporated under a vacuum, this operation being repeated 4 times to yield a white solid of molecule BA4 in hydrochloride salt form after drying at reduced pressure.

Yield: 20.02 g (84%).
$^1$H NMR (DMSO-de, ppm): 0.85 (6H); 1.15-2.35 (66H); 2.80-3.20 (6H); 3.30-3.65 (16H); 4.10-4.45 (3H); 7.55-8.60 (6H).
LC/MS (ESI): 964.9; (calculated ([M+H]$^+$): 964.6).

Molecule B12: Product Obtained by Reaction Between Molecule A1 and L-Lysine

By a method similar to the one used for the preparation of molecule B applied to molecule A1 (19.10 g, 54.02 mmol) and to L-lysine (4.15 g, 28.36 mmol), an oily residue is obtained after concentration of the reaction medium at reduced pressure. This residue is diluted in water (150 mL), washed with ethyl acetate (2×75 mL), then the aqueous phase is acidified to pH 1 by slow addition of 6 N HCl. The product is extracted 3 times with dichloromethane, the organic phase is dried over Na$_2$SO$_4$, then filtered and concentrated at reduced pressure to yield 11.2 g of yellow oily residue. In parallel, the previous organic phase of ethyl acetate is washed with a 2 N aqueous HCl solution (2×75 mL), a saturated aqueous NaCl solution (75 mL), dried over Na$_2$SO$_4$, filtered and concentrated to yield 10.2 g of yellow oily residue. A white residue is obtained by recrystallization of each one of these residues in acetone.
Yield: 11.83 g (54%)
$^1$H NMR (CDCl$_3$, ppm): 0.87 (6H); 1.06-2.44 (70H); 2.78-2.96 (1H); 3.35-3.75 (5H); 4.28-4.43 (0.1H); 4.43-4.52 (0.2H); 4.52-4.61 (1.8H); 4.61-4.75 (0.9H); 7.74-8.02 (2H).
LC/MS (ESI): 818.0; (calculated ([M+H]$^+$): 818.7).

Molecule B13: Product Obtained by Coupling Between Molecule B12 and Boc-Ethylenediamine DIPEA (3.42 g, 26.43 mmol) is added to a solution of molecule B12 (18.00 g, 22.02 mmol) at room temperature in THF (110 mL). The reaction medium is cooled to 0° C., then HOBt (337 mg, 2.20 mmol, EDC (4.64 g, 24.23 mmol) and then Boc-ethylenediamine (4.23 g, 26.43 mmol) are added successively. The reaction mixture is stirred for 1 h at 0° C., then for 24 h at room temperature and concentrated at reduced pressure. The residue is dissolved in ethyl acetate (250 mL) and dichloromethane (40 mL), the organic phase is washed with a 1 N aqueous HCl solution (2×125 mL), a saturated aqueous NaCl solution (2×125 mL), dried over Na$_2$SO$_4$ and concentrated at reduced pressure. A white solid is obtained after recrystallization two times in acetonitrile.
Yield: 17.5 g (83%)
$^1$H NMR (DMSO-d6, ppm): 0.85 (61-1); 1.15-2.29 (79H); 2.92-3.12 (6H); 3.30-3.59 (4H); 4.06-4.13 (0.65H); 4.16-4.29 (2H); 4.38-4.42 (0.35H); 6.71-6.76 (1H); 7.60-7.69 (1.3H); 7.76-7.81 (0.65H); 7.93-7.97 (0.35H); 8.00-8.04 (0.35H); 8.10-8.17 (0.35H).
LC/MS (ESI): 960.4; (calculated ([M+H]$^+$): 960.8).

Molecule BA5

By a method similar to the one used for the preparation of molecule BA1 applied to molecule B13 (24.4 g, 25.43 mmol), the residue obtained after concentration under a vacuum is solubilized in dichloromethane (150 mL), the organic phase is washed 2 times with a 2M aqueous sodium hydroxide solution (90 mL). Acetonitrile (120 mL) is added, and the dichloromethane is eliminated by concentration at reduced pressure. The medium is then allowed to rest for 72 h, and a white solid is obtained after filtration and rinsing with acetonitrile, then drying at reduced pressure. This operation is repeated 4 times.
Yield: 14.28 g (65%)
$^1$H NMR (DMSO-d6, ppm): 0.85 (6H); 1.06-2.32 (70H); 2.53-2.63 (2H); 2.89-3.61 (10H); 4.04-4.43 (3H); 7.55-7.62 (0.65H); 7.65-7.72 (0.65H); 7.80 (0.65H); 7.91 (0.35H); 8.03 (0.35H); 8.14-8.23 (0.35H).
LC/MS (ESI): 860.0; (calculated ([M+H]$^+$): 860.8).

Example BA6: Molecule BA6

Molecule B14: Product Obtained by Coupling Between Molecule B7 and 2,3-Diaminopropionic Acid By a method similar to the one used for the preparation of molecule B1 applied to molecule B7 (80.00 g, 245.78 mmol) and to the 2,3-diaminopropionic acid dihydrochloride (22.84 g, 129.04 mmol), a white solid is obtained after recrystallization in acetonitrile.
Yield: 69 g (78%)
$^1$H NMR (DMSO-d6, ppm): 0.86 (6H); 1.08-1.38 (40H); 1.40-1.55 (4H); 1.68-2.30 (12H); 3.16-3.66 (6H); 4.20-4.39 (3H); 7.67-8.31 (2H); 12.70 (1H).
LC/MS (ES): 719.4; 741.5; (calculated ([M+H]$^+$): 719.6; ([M+Na]$^+$): 741.6).

Molecule B15: Product Obtained by Coupling Between B14 and Boc-Ethylenediamine

By a method similar to the one used for the preparation of molecule B13 applied to molecule B14 (32.00 g, 44.50 mmol) in solution in dichloromethane and to Boc-ethylenediamine (8.56 g, 53.40 mmol), a colorless oil is obtained after purification by chromatography on silica gel (ethyl acetate, methanol).
Yield: 24.5 g (64%)
$^1$H NMR (DMSO-d6, ppm): 0.85 (6H); 1.16-2.42 (65H); 2.89-3.14 (4H); 3.17-3.66 (6H); 4.11-4.43 (3H); 6.77 (1H); 7.38-8.23 (3H).
LC/MS (ESI): 861.7; (calculated ([M+H]$^+$): 861.7).

Molecule BA6

By a method similar to the one used for the preparation of molecule BA5 applied to molecule B15 (24.50 g, 28.45 mmol), a white solid is obtained after recrystallization in acetonitrile.
Yield: 19.7 g (91%)
$^1$H NMR (DMSO-d6, ppm): 0.85 (6H); 1.10-2.40 (58H); 2.51-2.62 (2H); 2.90-3.16 (2H); 3.16-3.67 (6H); 4.04-4.47 (3H); 7.33-8.27 (3H).
LC/MS (ESI): 761.5; (calculated ([M+H]$^+$): 761.6).

Example BA7: Molecule BA7

Molecule B16: Product Obtained by the Reaction Between N-(Tert-Butoxycarbonyl-1,6-Diaminohexane and Molecule B8

By a method similar to the one used for the preparation of molecule B13 applied to molecule B8 (10 g, 13.14 mmol) and to N-(tert-butoxycarbonyl-1,6-diaminohexane (3.41 g, 15.77 mmol) in dichloromethane, a white solid is obtained after recrystallization in acetonitrile.

Yield: 10.7 g (85%)

$^1$H NMR (CDCl$_3$, ppm): 0.88 (6H); 1.17-2.40 (79H); 3.00-3.71 (10H); 4.26-4.58 (3H); 4.67 (1H); 6.74 (1H); 7.34-7.49 (2H).

LC/MS (ESI): 969.9; (calculated ([M+H]$^+$): 959.8).

Molecule BA7

After a method similar to the one used for the preparation of molecule BA1 applied to molecule B16 (10.5 g, 10.94 mmol), a 2N aqueous NaOH solution is added dropwise to the reaction cooled to 0° C. The aqueous phase is extracted with dichloromethane, then the organic phase is washed 3 times with a 5% aqueous NaCl solution. After drying over Na$_2$SO$_4$, the organic phase is filtered, concentrated under a vacuum, and the residue is recrystallized in acetonitrile.

Yield: 5.4 g (58%).

$^1$H NMR (CDCl$_3$, ppm): 0.88 (6H); 1.19-2.40 (72H); 2.67 (2H); 3.03-3.70 (8H); 4.26-4.57 (3H); 6.71 (1H); 7.39-7.49 (2H).

LC/MS (ESI): 859.8; (calculated ([M+H]$^+$): 859.7).

BB: Synthesis of the Co-Polyamino Acids

Co-Polyamino Acids with Statistical Grafting (Formulas VII and VIIa)

TABLE 1d list of the co-polyamino acids synthesized according to the invention

| No. | co-polyamino acids bearing carboxylate charges and hydrophobic radicals |
|---|---|
| BB1 | [structure shown] i = 0.05, DP (m + n) = 23; Hy = [structure]; R$_1$ = H or pyroglutamate |
| BB2 | [structure shown] i = 0.047, DP (m + n) = 21 |

TABLE 1d-continued
list of the co-polyamino acids synthesized according to the invention
| No. | co-polyamino acids bearing carboxylate charges and hydrophobic radicals |
|---|---|
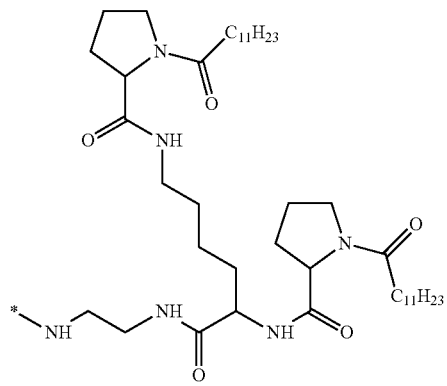
Hy =
$R_1$ = H or pyroglutamate
BB3
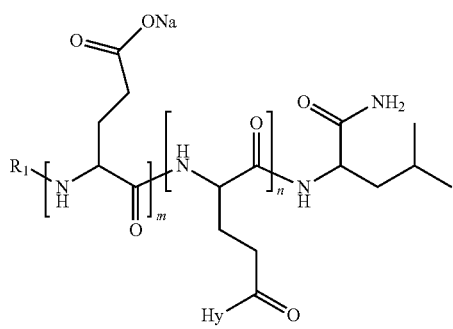
i = 0.049, DP (m + n) = 34
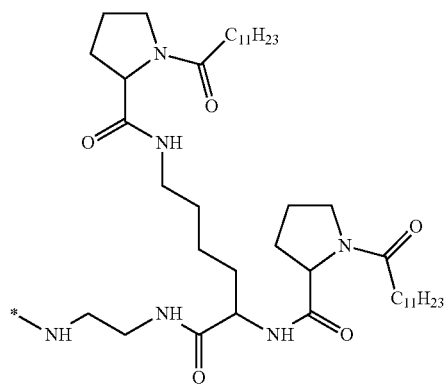
Hy =
R1 = H or pyroglutamate TABLE 1d-continued
list of the co-polyamino acids synthesized according to the invention
| No. | co-polyamino acids bearing carboxylate charges and hydrophobic radicals |
BB4
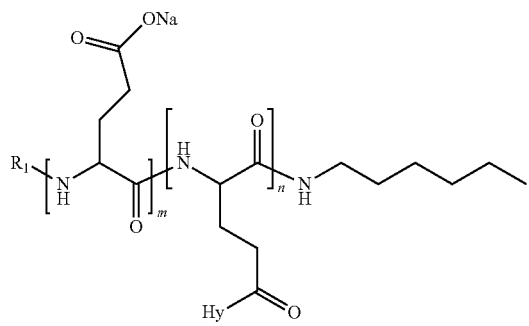
i = 0.04, DP (m + n) = 65
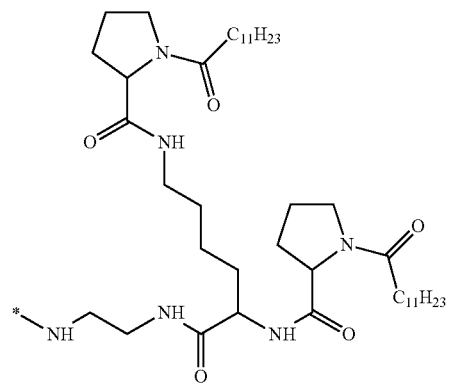
Hy =
R1 = H or pyroglutamate
BB5
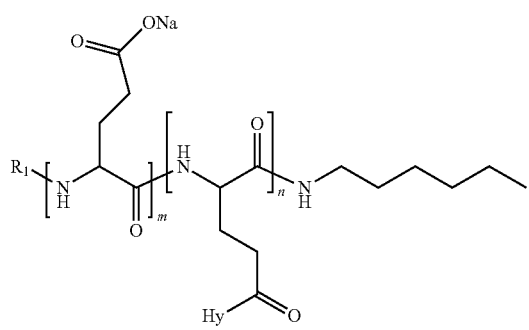
i = 0.042, DP (m + n) = 23

TABLE 1d-continued
list of the co-polyamino acids synthesized according to the invention
| No. | co-polyamino acids bearing carboxylate charges and hydrophobic radicals |
|---|---|
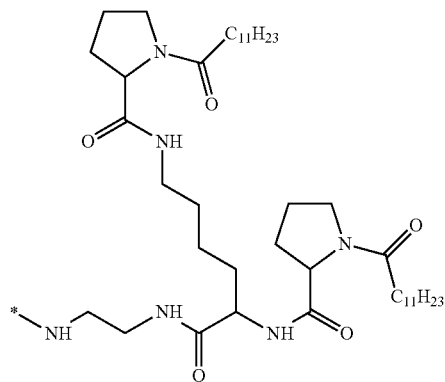
Hy =
$R_1 = CH_3$—C(O)—, H or pyroglutamate
BB6
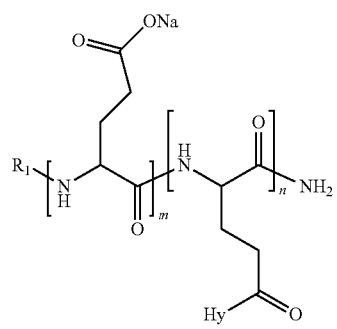
i = 0.04, DP (m + n) = 24
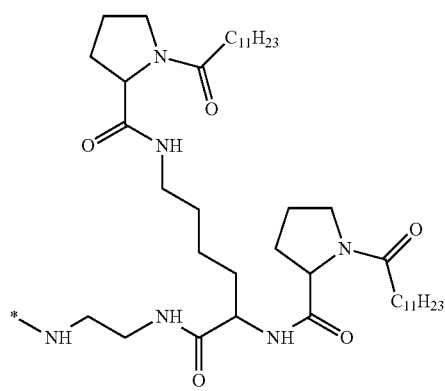
Hy =
$R_1 = CH_3$—C(O)—, H or pyroglutamate TABLE 1d-continued
list of the co-polyamino acids synthesized according to the invention
| No. | co-polyamino acids bearing carboxylate charges and hydrophobic radicals |
|---|---|
BB7
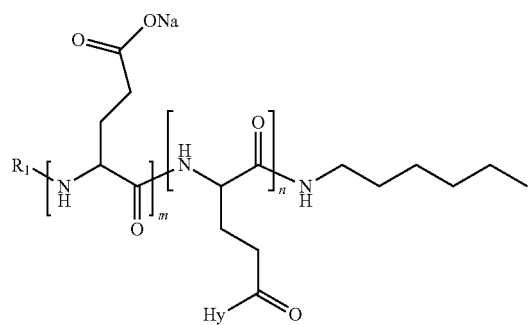
i = 0.042, DP (m + n) = 22
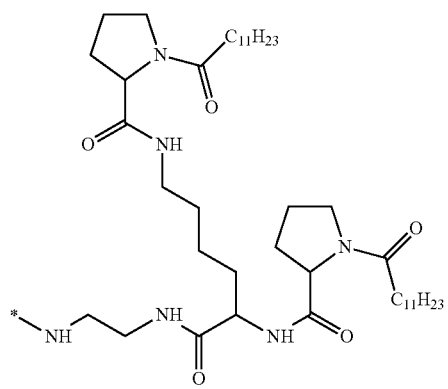
Hy =
$R_1$ = H or pyroglutamate
BB8
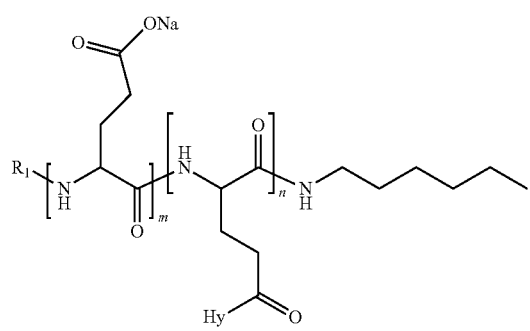
i = 0.026, DP (m + n) = 21

TABLE 1d-continued
list of the co-polyamino acids synthesized according to the invention
| No. | co-polyamino acids bearing carboxylate charges and hydrophobic radicals |
|---|---|
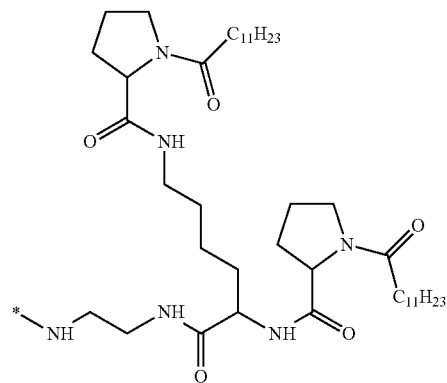
Hy =
$R_1$ = H or pyroglutamate
BB9
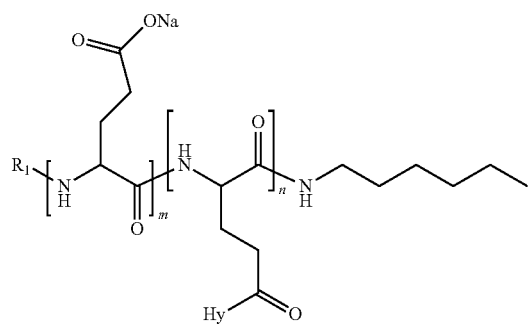
i = 0.05, DP (m + n) = 26
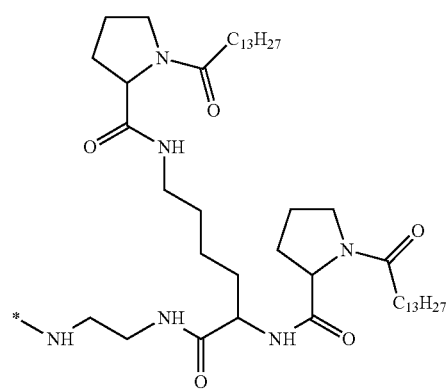
Hy =
$R_1$ = H or pyroglutamate TABLE 1d-continued
list of the co-polyamino acids synthesized according to the invention
| No. | co-polyamino acids bearing carboxylate charges and hydrophobic radicals |
|---|---|
BB10
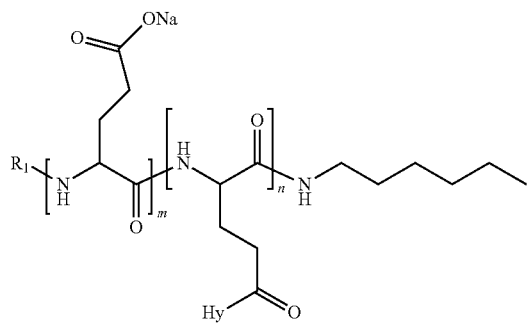
i = 0.029, DP (m + n) = 22
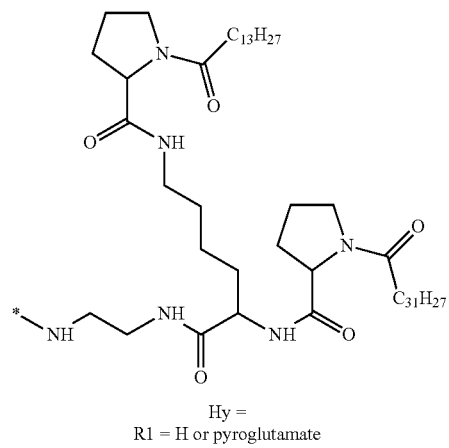
Hy =
R1 = H or pyroglutamate
BB11
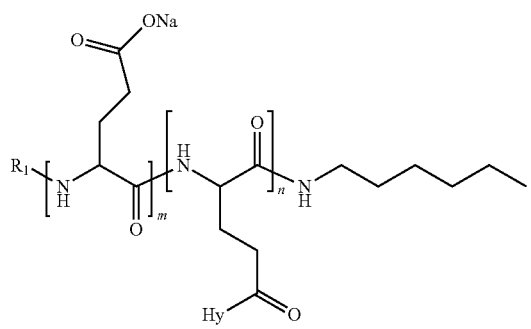
i = 0.032, DP (m + n) = 22

TABLE 1d-continued
list of the co-polyamino acids synthesized according to the invention
| No. | co-polyamino acids bearing carboxylate charges and hydrophobic radicals |
|---|---|
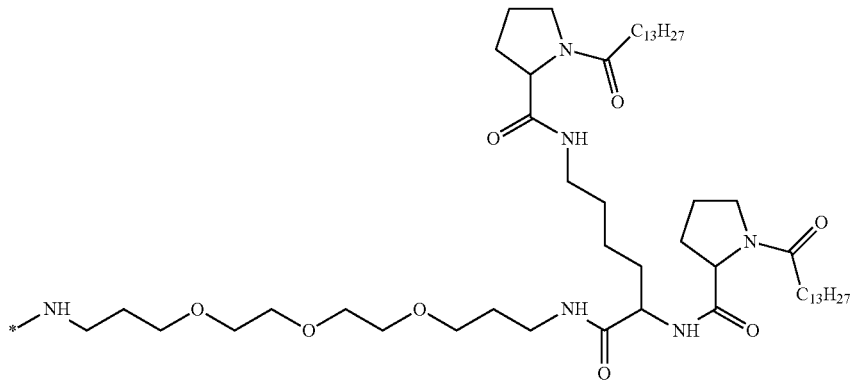
Hy =
$R_1 = CH_3—C(O)—$, H or pyroglutamate
BB12
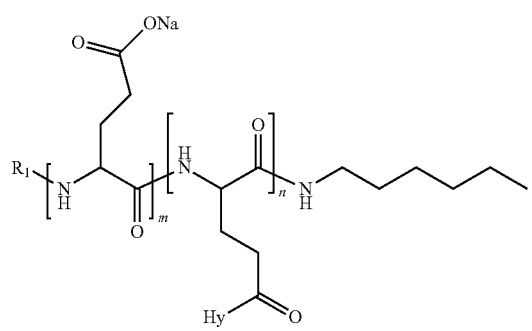
i = 0.03, DP (m + n) = 23
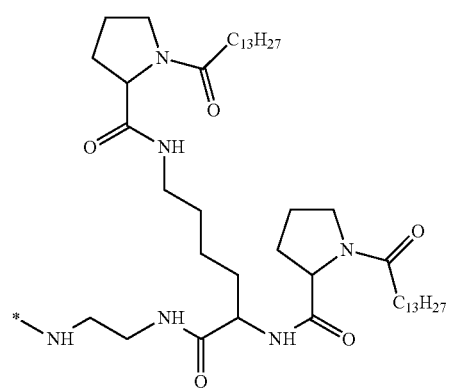
Hy =
$R_1 = CH_3—C(O)—$, H or pyroglutamate

TABLE 1d-continued list of the co-polyamino acids synthesized according to the invention

| No. | co-polyamino acids bearing carboxylate charges and hydrophobic radicals |
|---|---|
| BB13 | 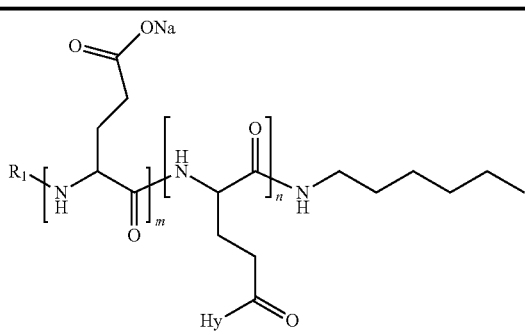<br>$i = 0.08$, DP = 25<br>Hy =<br>$R_1$ = H or pyroglutamate |

Co-Polyamino Acids with Defined Grafting (Formulas VII and VIIb)

TABLE 1e list of the co-polyamino acids synthesized according to the invention

| No. | co-polyamino acids bearing carboxylate charges and hydrophobic radicals |
|---|---|
| BB14 | 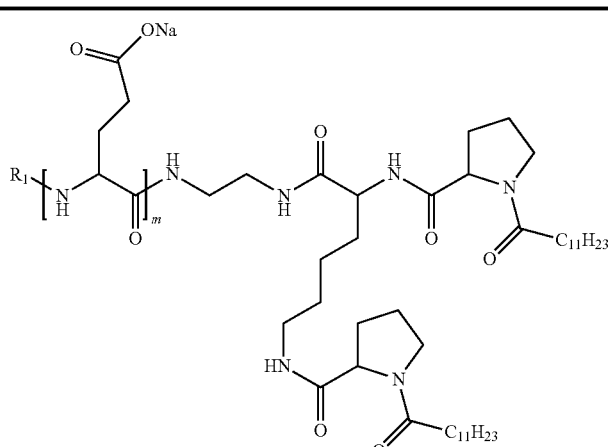<br>$i = 0.034$, DP (m) = 29<br>$R_1$ = H or pyroglutamate |

TABLE 1e-continued
list of the co-polyamino acids synthesized according to the invention
| No. | co-polyamino acids bearing carboxylate charges and hydrophobic radicals |
|---|---|
| BB15 | 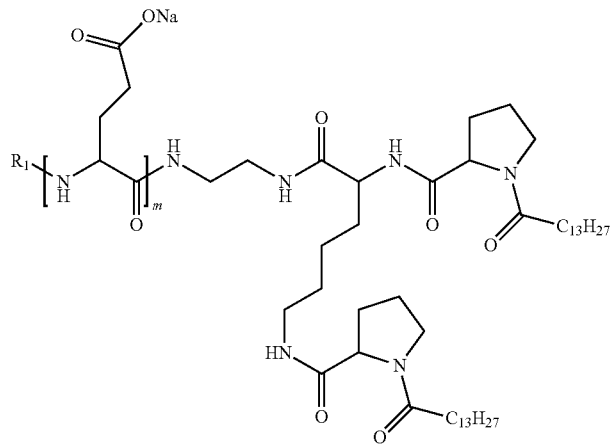<br>i = 0.042, DP (m) = 24<br>R$_1$ = H or pyroglutamate |
| BB16 | 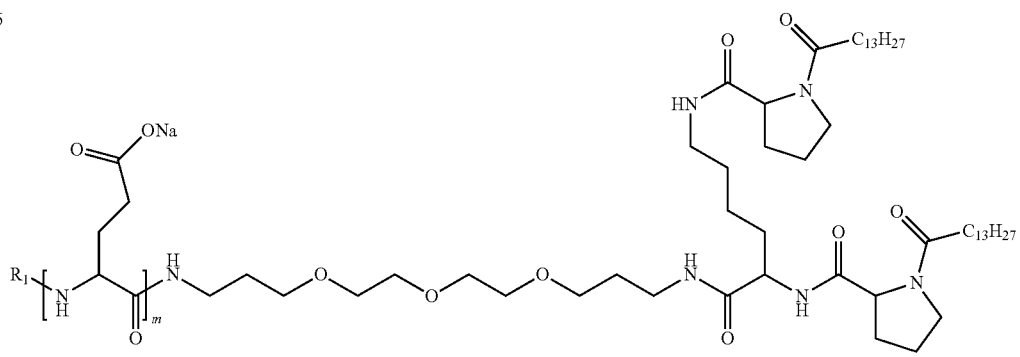<br>i = 0.043, DP (m) = 23<br>R$_1$ = H or pyroglutamate |
| BB17 | 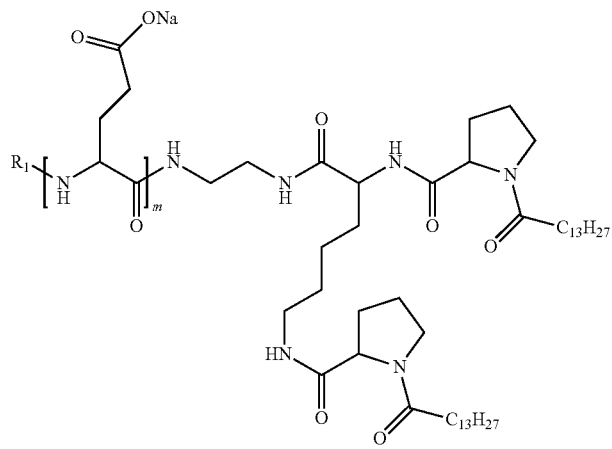<br>i = 0.015, DP (m) = 65<br>R$_1$ = H or pyroglutamate |

TABLE 1e-continued
list of the co-polyamino acids synthesized according to the invention
| No. | co-polyamino acids bearing carboxylate charges and hydrophobic radicals |
|---|---|
| BB18 | 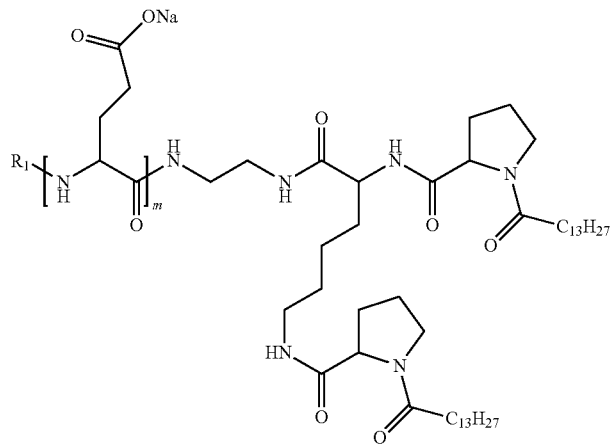<br>i = 0.025, DP (m) = 40<br>$R_1$ = H or pyroglutamate |
| BB19 | 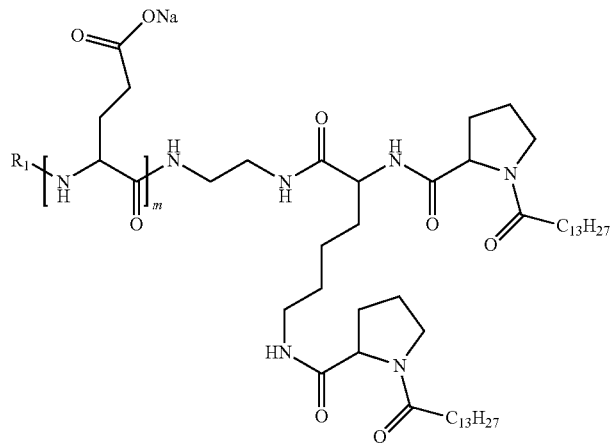<br>i = 0.04, DP (m) = 25<br>$R_1$ = H or pyroglutamate |
| BB20 | 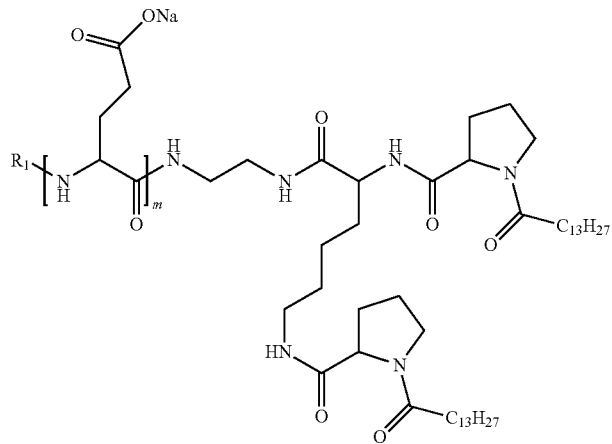<br>i = 0.059, DP (m) = 17<br>$R_1$ = H or pyroglutamate |

TABLE 1e-continued
list of the co-polyamino acids synthesized according to the invention
| No. | co-polyamino acids bearing carboxylate charges and hydrophobic radicals |
|---|---|
| BB21 | 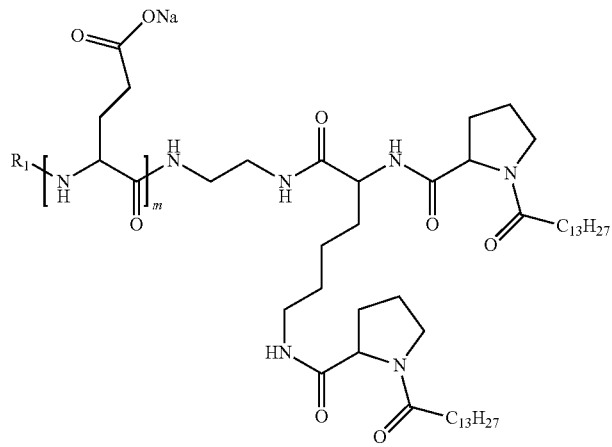 i = 0.11, DP (m) = 9<br>$R_1$ = H or pyroglutamate |
| BB22 | 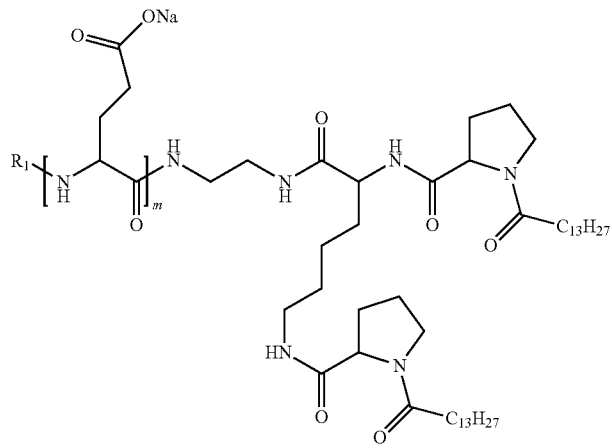 i = 0.048, DP (m) = 21<br>$R_1$ = H or pyroglutamate |
| BB23 | 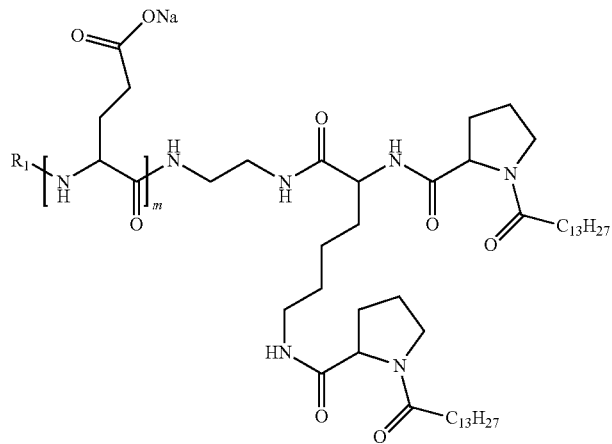 i = 0.048, DP (m) = 21<br>$R_1$ = H or pyroglutamate |

TABLE 1e-continued
list of the co-polyamino acids synthesized according to the invention
| No. | co-polyamino acids bearing carboxylate charges and hydrophobic radicals |
|---|---|
| BB24 | 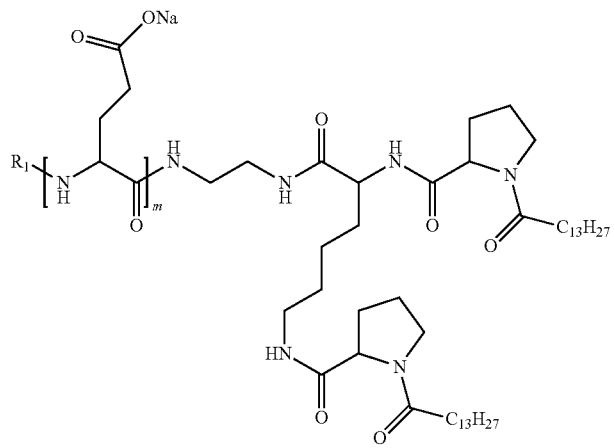
i = 0.040, DP (m) = 25
$R_1$ = H or pyroglutamate |
| BB25 | 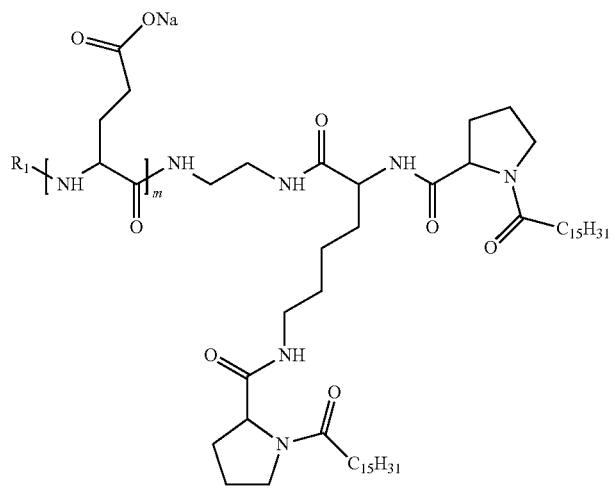
i = 0.043, DP (m) = 23
$R_1$ = H or pyroglutamate |

TABLE 1e-continued
list of the co-polyamino acids synthesized according to the invention
| No. | co-polyamino acids bearing carboxylate charges and hydrophobic radicals |
|---|---|
| BB26 | 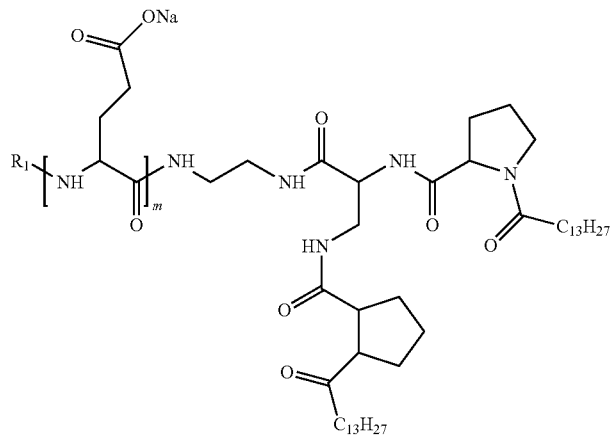 i = 0.048, DP (m) = 21<br>R₁ = H or pyroglutamate |
| BB27 | 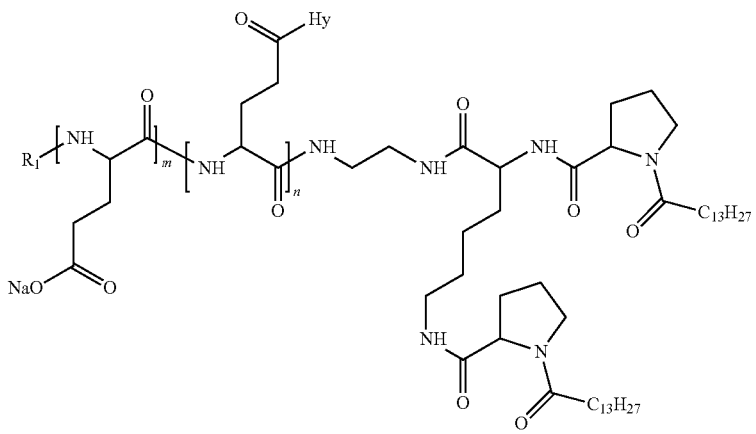 i = 0.089, DP (m + n) = 22<br><br>Hy = 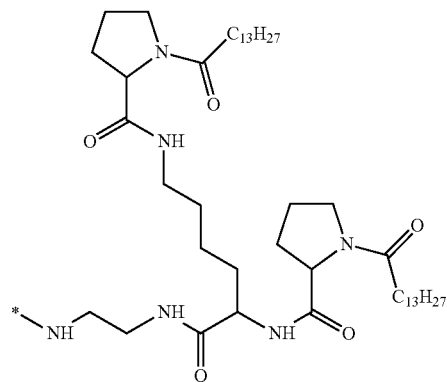<br>R₁ = H or pyroglutamate |

TABLE 1e-continued
list of the co-polyamino acids synthesized according to the invention
| No. | co-polyamino acids bearing carboxylate charges and hydrophobic radicals |
|---|---|
| BB42 | 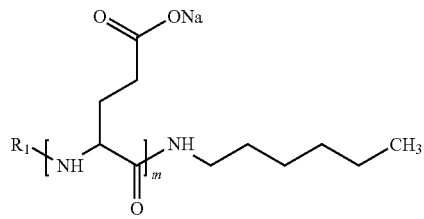 i = 0.045, DP (m) = 22<br><br>$R_1 =$ 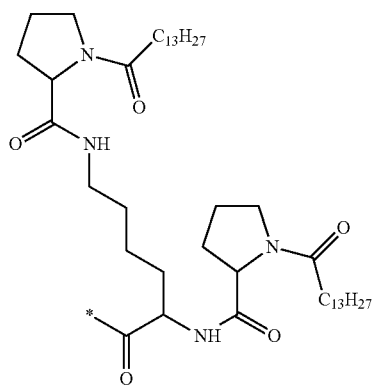 |
| BB43 | 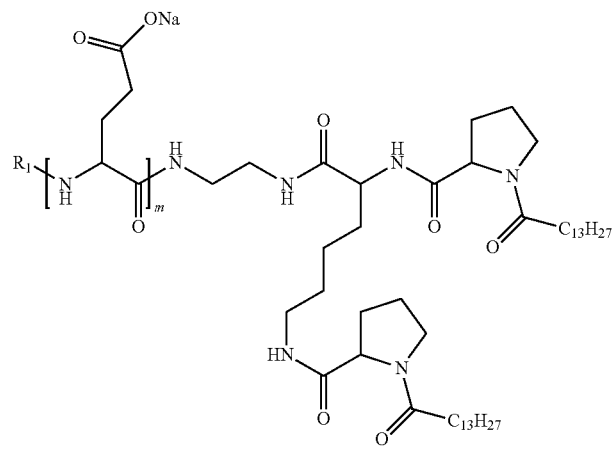 i = 0.09, DP (m) = 22 |

TABLE 1e-continued list of the co-polyamino acids synthesized according to the invention

| No. | co-polyamino acids bearing carboxylate charges and hydrophobic radicals |
|---|---|
| BB44 | 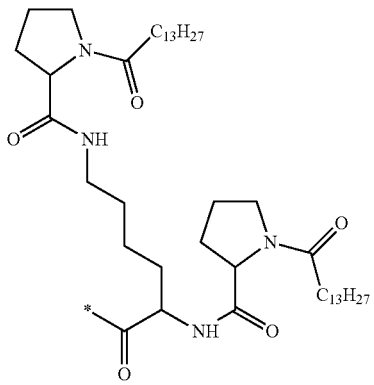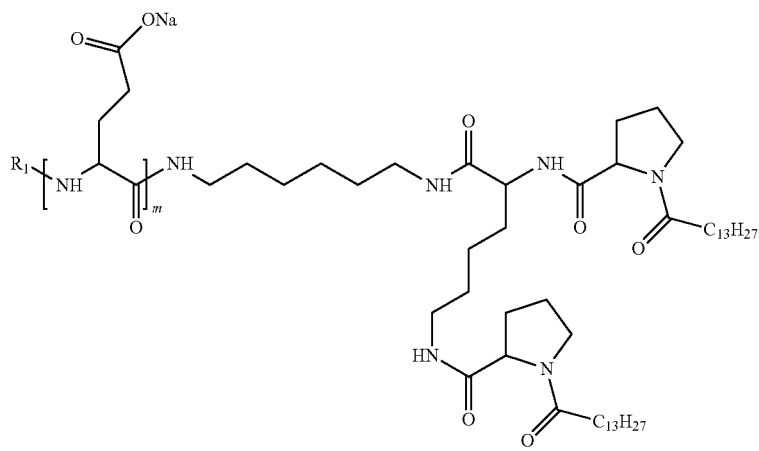<br>$i = 0.04$, DP (m) = 25<br>$R_1$ = H or pyroglutamate |

Example BB1: Co-Polyamino Acid BB1—Sodium Poly-L-Glutamate Modified by Molecule BA2 and Having a Number Average Molecular Weight (Mn) of 2400 g/mol Co-polyamino acid BB1-1: poly-L-glutamic acid having a relative number average molecular weight (Mn) of 3860 g/mol originating from the polymerization of γ-benzyl-L-glutamate N-carboxyanhydride initiated by hexylamine.

In a round-bottom flask dried beforehand in the oven, γ-benzyl-L-glutamate N-carboxyanhydride (90.0 g, 342 mmol) is placed under a vacuum for 30 min, then anhydrous DMF (465 mL) is introduced. The mixture is then stirred under argon until the dissolution is complete, cooled to 4° C., then hexylamine (1.8 mL, 14 mmol) is introduced rapidly. The mixture is stirred between 4° C. and room temperature for 2 days. The reaction medium is then heated at 65° C. for 4 h, cooled to room temperature, then poured dropwise into cold diisopropyl ether (6 L) under stirring. The white precipitate is recovered by filtration, washed with diisopropyl ether (500 mL, then 250 mL), then dried under a vacuum at 30° C. to yield a poly(γ-benzyl-L-glutamic acid) (PBLG).

A 33% hydrobromic acid (HBr) solution in acetic acid (135 mL, 0.77 mol) is added dropwise to a solution of PBLG (42.1 g) in trifluoroacetic acid (TFA, 325 mL) at 4° C. The mixture is stirred at room temperature for 2 h, then poured dropwise onto a 1:1 (v/v) mixture of diisopropyl ether and water under stirring (1.6 L). After 1 h 30 of stirring, the heterogeneous mixture is allowed to rest overnight. The white precipitate is recovered by filtration, washed with a 1:1 (v/v) mixture of diisopropyl ether and water (200 mL).

The solid obtained is then solubilized in water (1 L) by adjusting the pH to 7 by adding a 10 N aqueous sodium hydroxide solution, then a 1 N aqueous sodium hydroxide solution. After solubilization, the theoretical concentration is adjusted to 25 g/L theoretical by addition of water until obtaining a final volume of 1.5 L.

The solution is filtered through a 0.45-μm filter, then purified by ultrafiltration against a 0.9% NaCl solution, then water until the conductimetry of the permeate is less than 50 S/cm.

The aqueous solution is then acidified by addition of 37% hydrochloric acid solution until a pH of 2 is reached. After 4 h of stirring, the precipitate obtained is filtered, then dried under a vacuum at 30° C. to yield a poly-L-glutamic acid having a number average molecular weight (Mn) of 3860 g/mol with respect to a standard of polyoxyethylene (PEG).

Co-Polyamino Acid BB1

The co-polyamino acid BB1-1 (10.0 g) is solubilized in DMF (700 mL) at 30-40° C. then cooled to 0° C. The hydrochloride salt of molecule BA2 (2.95 g, 3.8 mmol) is suspended in DMF (45 mL), and triethylamine (0.39 g, 3.8 mmol) is then added to this suspension, then the mixture is heated slightly under stirring until the dissolution is complete. N-Methylmorpholine (NMM, 7.6 g, 75 mmol) in DMF (14 mL) and ethyl chloroformate (ECF, 8.1 g, 75 mmol) are added to the solution of co-polyamino acid at 0° C. After 10 min at 0° C., the solution of BA2 is added, and the medium is maintained at 30° C. for 1 h. The reaction medium is poured dropwise onto 6 L of water containing 15% by weight of sodium chloride, and HCl (pH 2), then left to rest overnight. The precipitate is collected by filtration, washed with the sodium chloride solution at pH 2 (1 L) and dried under a vacuum for approximately 1 h. The white solid obtained is taken up in water (600 mL), and the pH is adjusted to 7 by slow addition of a 1 N aqueous NaOH solution. The volume is adjusted to 700 mL by addition of water. After filtration through a 0.45-µm filter, the clear solution obtained is purified by ultrafiltration against a 0.9% NaCl solution, then water until the conductimetry of the permeate is less than 50 µS/cm. After discharging, the solution is filtered through a 0.2-µm filter and stored at 2-8° C.

Dry extract: 19.7 mg/g.
DP (estimated based on $^1$H NMR): 23.
Based on $^1$H NMR: i=0.05.
The calculated average molecular weight of the co-polyamino acid BB1 is 4350 g/mol.
HPLC-aqueous SEC (calibrant PEG): Mn=2400 g/mol.

Example BB2: Co-Polyamino Acid BB2—Sodium Poly-L-Glutamate Modified by Molecule BA2 and Having a Number Average Molecular Weight (Mn) of 4900 g/mol A poly-L-glutamic acid having a number average molecular weight (Mn) of 4100 g/mol (5.0 g) obtained by a method similar to the one used for the preparation of the co-polyamino acid BB1-1 is solubilized in DMF (205 mL) at 30-40° C., then maintained at this temperature. In parallel, the hydrochloride salt of molecule BA2 (1.44 g, 1.84 mmol) is suspended in DMF (10 mL), and triethylamine (0.19 g, 1.84 mmol) is added, then the mixture is heated slightly under stirring until the dissolution is complete. NMM (3.7 g, 36.7 mmol), the solution of molecule BA2, then 2-hydroxypyridine N-oxide (HOPO, 0.31 g, 2.76 mmol) are added successively to the solution of co-polyamino acid in DMF. The reaction medium is then cooled to 0° C., then EDC (0.53 g, 2.76 mmol) is added and the temperature of the medium is allowed to rise to room temperature over a time period of 3 h. The reaction medium is poured dropwise onto 1.55 L of water containing 15% by weight of NaCl and HCl (pH 2) under stirring. At the end of the addition, the pH is readjusted to 2 with a 1 N HCl solution, and the suspension is allowed to rest overnight. The precipitate is collected by filtration, then rinsed with 100 mL of water. The white solid obtained is solubilized in 200 mL of water by slow addition of a 1 N aqueous NaOH solution until the pH is 7 under stirring, then the solution is filtered through a 0.45-µm filter. The clear solution obtained is purified by ultrafiltration against a 0.9% NaCl solution, then water until the conductimetry of the permeate is less than 50 µS/cm. The solution obtained is filtered through a 0.2-µm filter and stored at 2-8° C.

Dry extract: 16.3 mg/g.
DP (estimated based on $^1$H NMR): 21.
Based on $^1$H NMR: li=0.047.
The calculated average molecular weight of the co-polyamino acid BB2 is 3932 g/mol.
HPLC-aqueous SEC (calibrant PEG): Mn=4900 g/mol.

Example BB3: Co-Polyamino Acid BB3—Sodium Poly-L-Glutamate Modified by Molecule BA2 and Having a Number Average Molecular Weight (Mn) of 6400 g/mol Co-Polyamino Acid BB3-1:

poly-L-glutamic acid having a number average molecular weight (Mn) of 17500 g/mol originating from the polymerization of γ-methyl-L-glutamate N-carboxyanhydride initiated by L-leucinamide.

A poly-L-glutamic acid having a number average weight (Mn) of 17500 g/mol with respect to a methyl polymethacrylate (PMMA) standard is obtained by polymerization of γ-methyl-glutamic acid N-carboxyanhydride using L-leucinamide as initiator and carrying out a deprotection of the methyl esters by using a 37% hydrochloric acid solution according to the method described in patent application FR-A-2 801 226.

By a method similar to the one used for the preparation of the co-polyamino acid BB2 applied to the hydrochloride salt of molecule BA2 (3.23 g, 4.1 mmol) and to the co-polyamino acid BB3-1 (11 g), a sodium poly-L-glutamate modified by molecule BA2 is obtained.

Dry extract: 27.5 mg/g.
DP (estimated based on $^1$H NMR): 34.
Based on $^1$H NMR: li=0.049
The calculated average molecular weight of the co-polyamino acid BB3 is 6405 g/mol.
HPLC-aqueous SEC (calibrant PEG): Mn=6400 g/mol.

Example BB4: Co-Polyamino Acid BB4—Sodium Poly-L-Glutamate Modified by Molecule BA2 and Having a Number Average Molecular Weight (Mn) of 10500 g/mol By a method similar to the one used for the preparation of the co-polyamino acid BB2 applied to the hydrochloride salt of molecule BA2 (5 g, 6.35 mmol) and to a poly-L-glutamic acid having a number average molecular weight Mn=10800 g/mol (21.7 g) obtained by a method similar to the one used for the preparation of the co-polyamino acid BB1-1, a sodium poly-L-glutamate modified by molecular BA2 is obtained.

Dry extract: 28.2 mg/g.
DP (estimated based on $^1$H NMR): 65.
Based on $^1$H NMR: i=0.04.
The calculated average molecular weight of the co-polyamino acid BB4 is 11721 g/mol.
HPLC-aqueous SEC (calibrant PEG): Mn=10500 g/mol.

Example BB5: Co-Polyamino Acid BB5—Sodium Poly-L-Glutamate Capped at One of its Ends by an Acetyl Group and Modified by Molecule BA2 and Having a Number Average Molecular Weight (Mn) of 3600 g/mol Co-Polyamino Acid BB5-1:

poly-L-glutamic acid having an Mn of 3700 g/mol originating from the polymerization of γ-benzyl-L-glutamate N-carboxyanhydride initiated by hexylamine and capped at one of its ends by an acetyl group.

γ-Benzyl-L-glutamate N-carboxyanhydride (100.0 g, 380 mmol) is placed under a vacuum for 30 minutes in a round-bottom flask dried beforehand in the oven, then anhydrous DMF (250 mL) is introduced. The mixture is then stirred under argon until the dissolution is complete, cooled to 4° C., then hexylamine (2.3 mL, 17 mmol) is introduced rapidly. The mixture is stirred between 4° C. and room temperature for 2 days, then precipitated in diisopropyl ether (3.4 L). The precipitate is recovered by filtration, washed two times with diisopropyl ether (225 mL), then dried to yield a white solid which is dissolved in 450 mL of THF. N,N-Diisopropylethylamine (DIPEA, 31 mL, 176 mmol) then acetic anhydride (17 mL, 176 mmol) are added successively to this solution. After stirring at room temperature overnight the solution is poured slowly into diisopropyl ether (3 L) for a time period of 30 min and under stirring. After 1 h of stirring, the precipitate is filtered, washed two times with diisopropyl ether (200 mL), then dried under a vacuum at 30° C. to yield a poly(γ-benzyl-L-glutamic acid) capped at one of its ends by an acetyl group.

A 33% hydrobromic acid (HBr) solution in acetic acid (235 mL, 1.34 mol) is added dropwise to a solution of the capped co-polyamino acid (72 g) in trifluoroacetic acid (TFA, 335 mL) at 4° C. The mixture is stirred at room temperature for 3 h 30, then poured dropwise onto a 1:1 (v/v) mixture of diisopropyl ether and water under stirring (4 L). After 2 h of stirring, the heterogeneous mixture is allowed to rest overnight. The white precipitate is recovered by filtration, washed with a 1:1 (v/v) mixture of diisopropyl ether and water (340 mL), then with water (340 mL). The solid obtained is then solubilized in water (1.5 L) by adjusting the pH to 7 by addition of a 10 N aqueous sodium hydroxide solution, then a 1 N aqueous sodium hydroxide solution. After solubilization, the theoretical concentration is adjusted to 20 g/L theoretical by addition of water until obtaining a final volume of 2.1 L. The solution is filtered through a 0.45-μm filter, then purified by ultrafiltration against a 0.9% NaCl solution, then water until the conductimetry of the permeate is less than 50 μS/cm. The solution of co-polyamino acid is then concentrated until a final volume of 1.8 L is obtained. The aqueous solution is then acidified by addition of 37% hydrochloric acid solution until a pH of 2 is reached. After 4 h of stirring, the precipitate obtained is filtered, washed with water (330 mL), then dried under a vacuum at 30° C. to yield a poly-L-glutamic acid having a number average molecular weight (Mn) of 3700 g/mol with respect to a standard of polyoxyethylene (PEG).

Co-Polyamino Acid BB5

By a method similar to the one used for the preparation of the co-polyamino acid BB2 applied to the hydrochloride salt of molecule BA2 (6.92 g, 8.8 mmol) and to co-polyamino acid BB5-1 (30.0 g), a sodium poly-L-glutamate capped at one of its ends by an acetyl group and modified by molecule BA2 is obtained.

Dry extract: 29.4 mg/g.
DP (estimated based on $^1$H NMR): 23.
Based on $^1$H NMR: i=0.042.
The calculated average molecular weight of the co-polyamino acid BB5 is 4302 g/mol.
HPLC-aqueous SEC (calibrant PEG): Mn=3600 g/mol.

Example BB6: Co-Polyamino Acid BB6—Sodium Poly-L-Glutamate Capped at One of its Ends by an Acetyl Group and Modified by Molecule BA2 and Having a Number Average Molecular Weight (Mn) of 4100 g/mol By a method similar to the one used for the preparation of the co-polyamino acid BB2 applied to the hydrochloride salt of molecule BA2 (5.8 g, 7.4 mmol) and to poly-L-glutamic acid having a number average molecular weight Mn=3800 g/mol (25 g) obtained by a method similar to the one used for the preparation of the co-polyamino acid BB5-1 using ammonia instead of hexylamine, a sodium poly-L-glutamate capped at one of its ends by an acetyl group and modified by molecule BA2 is obtained.

Dry extract: 27.6 mg/g.
DP (estimated based on $^1$H NMR): 24.
Based on $^1$H NMR: i=0.04.
The calculated average molecular weight of the co-polyamino acid BB6 is 4387 g/mol.
HPLC-aqueous SEC (calibrant PEG): Mn=4100 g/mol.

Example BB7: Co-Polyamino Acid BB7—Sodium Poly-L-Glutamate Modified by Molecule BA2 and Having a Number Average Molecular Weight (Mn) of 4200 g/mol By a method similar to the one used for the preparation of the co-polyamino acid BB2 applied to the hydrochloride salt of molecule BA2 (7.07 g, 9.0 mmol) and to a poly-L-glutamic acid having a number average molecular weight Mn=3600 g/mol (30.0 g) obtained by a method similar to the one used for the preparation of the co-polyamino acid BB1-1, a sodium poly-L-glutamate modified by molecule BA2 is obtained.

Dry extract: 28.3 mg/g.
DP (estimated based on $^1$H NMR): 22.
Based on $^1$H NMR: i=0.042.
The calculated average molecular weight of the co-polyamino acid BB7 is 4039 g/mol.
HPLC-aqueous SEC (calibrant PEG): Mn=4200 g/mol.

Example BB8: Co-Polyamino Acid BB8—Sodium Poly-L-Glutamate Modified by Molecule BA2 and Having a Number Average Molecular Weight (Mn) of 5200 g/mol By a method similar to the one used for the preparation of the co-polyamino acid BB2 applied to the hydrochloride salt of molecule BA2 (0.85 g, 1.1 mmol) and to a poly-L-glutamic acid having a number average molecular weight Mn=4100 g/mol (5.0 g) obtained by a method similar to the one used for the preparation of the co-polyamino acid BB1-1, a sodium poly-L-glutamate modified by molecule BA2 is obtained.

Dry extract: 28.6 mg/g.
DP (estimated based on $^1$H NMR): 21,
Based on $^1$H NMR: i=0.026.
The calculated average molecular weight of the co-polyamino acid BB8 is 3620 g/mol.

HPLC-aqueous SEC (calibrant PEG): Mn=5200 g/mol.

Example BB9: Co-Polyamino Acid BB9—Sodium Poly-L-Glutamate Modified by Molecule BA3 and Having a Number Average Molecular Weight (Mn) of 4700 g/mol By a method similar to the one used for the preparation of the co-polyamino acid BB2 applied to the hydrochloride salt of molecule BA3 (3.05 g, 3.6 mmol) and to a poly-L-glutamic acid having a number average molecular weight Mn=4100 g/mol (10.0 g) obtained by a method similar to the one used for the preparation of the co-polyamino acid BB1-1, a sodium poly-L-glutamate modified by molecule BA3 is obtained.

Dry extract: 28.6 mg/g.

DP (estimated based on $^1$H NMR): 26.

Based on $^1$H NMR: i=0.05.

The calculated average molecular weight of the co-polyamino acid BB9 is 4982 g/mol.

HPLC-aqueous SEC (calibrant PEG): Mn=4700 g/mol.

Example BB10: Co-Polyamino Acid BB10—Sodium Poly-L-Glutamate Modified by Molecule BA3 and Having a Number Average Molecular Weight (Mn) of 4200 g/mol By a method similar to the one used for the preparation of the co-polyamino acid BB2 applied to the hydrochloride salt of molecule BA3 (1.90 g, 2.3 mmol) and to a poly-L-glutamic acid having a number average molecular weight Mn=3500 g/mol (10.0 g) obtained by a method similar to the one used for the preparation of the co-polyamino acid BB1-1, a sodium poly-L-glutamate modified by molecule BA3 is obtained.

Dry extract: 25.9 mg/g.

DP (estimated based on $^1$H NMR): 22.

Based on $^1$H NMR: i=0.029.

The calculated average molecular weight of the co-polyamino acid BB10 is 3872 g/mol.

HPLC-aqueous SEC (calibrant PEG): Mn=4200 g/mol.

Example BB11: Co-Polyamino Acid BB11—Sodium Poly-L-Glutamate Capped at One of its Ends by an Acetyl Group and Modified by Molecule BA4 and Having a Number Average Molecular Weight (Mn) of 3900 g/mol By a method similar to the one used for the preparation of the co-polyamino acid BB2 applied to the hydrochloride salt of molecule BA4 (2.21 g, 2.2 mmol) and to a poly-L-glutamic acid having a number average weight Mn=3700 g/mol (10 g) obtained by a method similar to the one used for the preparation of the co-polyamino acid BB5-1, a sodium poly-L-glutamate capped at one of its ends by an acetyl group and modified by molecular BA4 is obtained.

Dry extract: 28.1 mg/g.

DP (estimated based on $^1$H NMR): 22.

Based on $^1$H NMR: i=0.032.

The calculated average molecular weight of the co-polyamino acid BB11 is 4118 g/mol.

HPLC-aqueous SEC (calibrant PEG): Mn=3900 g/mol.

Example BB12: Co-Polyamino Acid BB12—Sodium Poly-L-Glutamate Capped at One of its Ends by an Acetyl Group and Modified by Molecule BA3 and Having a Number Average Molecular Weight (Mn) of 3900 g/mol By a method similar to the one used for the preparation of the co-polyamino acid BB2 applied to the hydrochloride salt of molecule BA3 (1.9 g, 2.3 mmol) and to a poly-L-glutamic acid having a number average weight Mn=3600 g/mol (10 g) obtained by a method similar to the one used for the preparation of the co-polyamino acid BB5-1, a sodium poly-L-glutamate capped at one of its ends by an acetyl group and modified by molecular BA3 is obtained.

Dry extract: 26.7 mg/g.

DP (estimated based on $^1$H NMR): 23.

Based on $^1$H NMR: i=0.03.

The calculated average molecular weight of the co-polyamino acid BB12 is 4145 g/mol.

HPLC-aqueous SEC (calibrant PEG): Mn=3900 g/mol.

Example BB13: Co-Polyamino Acid BB13—Sodium Poly-L-Glutamate Modified by Molecule BA1 and Having a Number Average Molecular Weight (Mn) of 2800 g/mol By a method similar to the one used for the preparation of the co-polyamino acid BB1 applied to the hydrochloride salt of molecule BA1 (3.65 g, 5 mmol) and to a poly-L-glutamic acid having a number average molecular weight Mn=3600 g/mol (10 g) obtained by a method similar to the one used for the preparation of the co-polyamino acid BB1-1, a sodium poly-L-glutamate modified by molecule BA1 is obtained.

Dry extract: 25.6 mg/g.

DP (estimated based on $^1$H NMR): 25.

Based on $^1$H NMR: i=0.08.

The calculated average molecular weight of the co-polyamino acid BB13 is 5253 g/mol.

HPLC-aqueous SEC (calibrant PEG): Mn=2800 g/mol.

Example BB14: Co-Polyamino Acid BB14—Sodium Poly-L-Glutamate Modified at One of its Ends by Molecule BA2 and Having a Number Average Molecular Weight (Mn) of 4020 g/mol The hydrochloride salt of molecule BA2 (2.12 g, 2.70 mmol), chloroform (40 mL), molecular sieve 4 Å (1.5 g) as well as Amberlite IRN 150 ion exchange resin (1.5 g) are introduced successively into an appropriate container. After 1 h of stirring on rollers, the medium is filtered and the residue is rinsed with chloroform. The mixture is evaporated, then co-evaporated with toluene. The residue is solubilized in anhydrous DMF (20 mL) to be used directly in the polymerization reaction.

γ-Benzyl-L-glutamate N-carboxyanhydride (18 g, 68.42 mmol) is placed under a vacuum for 30 min in a round-bottom flask dried beforehand in the oven, then anhydrous DMF (100 mL) is introduced. The mixture is stirred under argon until the solubilization is complete, cooled to 4° C., then the solution of molecule BA2 prepared as described above is introduced rapidly. The mixture is stirred between 4° C. and room temperature for 2 days, then heated at 65° C. for 2 h. The reaction mixture is then cooled to room temperature, then poured dropwise into diisopropyl ether (1.2 L) under stirring. The white precipitate is recovered by filtration, washed two times with diisopropyl ether (100 mL), then dried under a vacuum at 30° C. to obtain a white solid. The solid is diluted in TFA (105 mL), and a 33% hydrobromic acid (HBr) solution in acetic acid (38 mL, 220 mmol) is then added dropwise and at 0° C. The solution is stirred for 2 h at room temperature, then poured dropwise onto a 1:1 (v/v) mixture of diisopropyl ether/water and under stirring (600 mL). After 2 h of stirring, the heterogeneous mixture is allowed to rest overnight. The white precipitate is recovered by filtration, washed successively with a 1:1 (v/v) mixture of diisopropyl ether and water (200 mL), then with water (100 mL). The solid obtained is solubilized in water (450 mL) by adjusting the pH to 7 by addition of a 10 N aqueous sodium hydroxide solution, then a 1 N aqueous sodium hydroxide solution. The mixture is filtered through a 0.45-μm filter, then purified by ultrafiltration against a 0.9% NaCl solution, then water until the conductimetry of the permeate is less than 50 μS/cm. The solution of co-polyamino acid is then concentrated to approximately 30 g/L theoretical and the pH is adjusted to 7.0. The aqueous solution is filtered through a 0.2-μm filter and stored at 4° C.

Dry extract: 22.3 mg/g.
DP (estimated by $^1$H NMR)=29, thus i=0.034.
The calculated average molecular weight of the co-polyamino acid BB14 is 5089 g/mol.
HPLC-aqueous SEC (calibrant PEG): Mn=4020 g/mol.

Example BB15: Co-Polyamino Acid
BB15—Sodium Poly-L-Glutamate Modified at One of its Ends by Molecule BA3 and Having a Number Average Molecular Weight (Mn) of 3610 g/mol By a method similar to the one used for the preparation of the co-polyamino acid BB14 applied to the hydrochloride salt of the molecule BA3 (3.62 g, 432 mmol) and to 25.0 g (94.97 mmol) of γ-benzyl-L-glutamate N-carboxyanhydride, a sodium poly-L-glutamate modified at one of its ends by the molecule BA3 is obtained.

Dry extract: 26.5 mg/g
DP (estimated by $^1$H NMR)=24, thus i=0.042.
The calculated average molecular weight of the co-polyamino acid BB15 is 4390 g/mol.
HPLC-aqueous SEC (calibrant PEG): Mn=3610 g/mol.

Example BB16: Co-Polyamino Acid
BB16—Sodium Poly-L-Glutamate Modified at One of its Ends by Molecule BA4 and Having a Number Average Molecular Weight (Mn) of 3300 g/mol By a method similar to the one used for the preparation of the co-polyamino acid BB14 applied to the hydrochloride salt of the molecule BA4 (5.70 g, 5.70 mmol) and to 29.99 g (113.9 mmol) of γ-benzyl-L-glutamate N-carboxyanhydride, a sodium poly-L-glutamate modified at one of its ends by the molecule BA4 is obtained.

Dry extract: 32.3 mg/g
DP (estimated by $^1$H NMR)=23, thus i=0.043.
The calculated average molecular weight of the co-polyamino acid BB16 is 4399 g/mol.

HPLC-aqueous SEC (calibrant PEG): Mn=3300 g/mol.

Example BB17: Co-Polyamino Acid
BB17—Sodium Poly-L-Glutamate Modified at One of its Ends by Molecule BA3 and Having a Number Average Molecular Weight (Mn) of 10700 g/mol By a method similar to the one used for the preparation of the co-polyamino acid BB14 applied to the hydrochloride salt of the molecule BA3 (2.51 g, 3 mmol) and at 52.7 g (200 mmol) of γ-benzyl-L-glutamate N-carboxyanhydride, a sodium poly-L-glutamate modified at one of its ends by the molecule BA3 is obtained.

Dry extract: 24.5 mg/g
DP (estimated by $^1$H NMR)=65, thus i=0.015.
The calculated average molecular weight of the co-polyamino acid BB17 is 10585 g/mol.
HPLC-aqueous SEC (calibrant PEG): Mn=10700 g/mol.

Example BB18: Co-Polyamino Acid
BB18—Sodium Poly-L-Glutamate Modified at One of its Ends by Molecule BA3 and Having a Number Average Molecular Weight (Mn) of 6600 g/mol By a method similar to the one used for the preparation of the co-polyamino acid BB14 applied to the hydrochloride salt of the molecule BA3 (2.51 g, 3 mmol) and at 31.6 g (120 mmol) of γ-benzyl-L-glutamate N-carboxyanhydride, a sodium poly-L-glutamate modified at one of its ends by the molecule BA3 is obtained.

Dry extract: 27.3 mg/g
DP (estimated by $^1$H NMR)=40, thus i=0.025.
The calculated average molecular weight of the co-polyamino acid BB18 is 6889 g/mol.
HPLC-aqueous SEC (calibrant PEG): Mn=6600 g/mol.

Example BB19: Co-Polyamino Acid
BB19—Sodium Poly-L-Glutamate Modified at One of its Ends by the Molecule BA3 and Having a Number Average Molecular Weight (Mn) of 3400 g/mol By a method similar to the one used for the preparation of the co-polyamino acid BB14 applied to the hydrochloride salt of the molecule BA3 (36.26 g, 43.2 mmol) and of γ-benzyl-L-glutamate N-carboxyanhydride (250.0 g, 949.7 mmol), a sodium poly-L-glutamate modified at one of its ends by the molecule BA3 is obtained.

Dry extract: 22.4 mg/g
DP (estimated by $^1$H NMR)=25, thus i=0.04.
The calculated average molecular weight of the co-polyamino acid BB19 is 4540 g/mol.
HPLC-aqueous SEC (calibrant PEG): Mn=3400 g/mol.

Example BB20: Co-Polyamino Acid
BB20—Sodium Poly-L-Glutamate Modified at One of its Ends by the Molecule BA3 and Having a Number Average Molecular Weight (Mn) of 2500 g/mol By a method similar to the one used for the preparation of the co-polyamino acid BB14 applied to the molecule BA3 in free amine form (1.017 g, 12.7 mmol) and of γ-benzyl-L- glutamate N-carboxyanhydride (5.0 g, 19.0 mmol), a sodium poly-L-glutamate modified at one of its ends by the molecule BA3 is obtained.

Dry extract: 11.2 mg/g
DP (estimated by $^1$H NMR)=17, thus i=0.059.
The calculated average molecular weight of the co-polyamino acid BB20 is 3332 g/mol.
HPLC-aqueous SEC (calibrant PEG): Mn=2500 g/mol.

Example BB21: Co-Polyamino Acid BB21—Sodium Poly-L-Glutamate Modified at One of its Ends by the Molecule BA3 and Having a Number Average Molecular Weight (Mn) of 1100 g/mol By a method similar to the one used for the preparation of the co-polyamino acid BB14 applied to the molecule BA3 in free amine form (3.814 g, 4.75 mmol) and of γ-benzyl-L-glutamate N-carboxyanhydride (10.0 g, 38.0 mmol), a sodium poly-L-glutamate modified at one of its ends by the molecule BA3 is obtained.

Dry extract: 16.1 mg/g
DP (estimated by $^1$H NMR)=9, thus i=0.11.
The calculated average molecular weight of the co-polyamino acid BB21 is 2123 g/mol.
HPLC-aqueous SEC (calibrant PEG): Mn=1100 g/mol.

Example BB22: Co-Polyamino Acid BB22—Sodium Poly-D-Glutamate Modified at One of its Ends by the Molecule BA3 and Having a Number Average Molecular Weight (Mn) of 2900 g/mol By a method similar to the one used for the preparation of the co-polyamino acid BB14 applied to the molecule BA3 in free amine form (2.77 g, 3.45 mmol) and of γ-benzyl-D-glutamate N-carboxyanhydride (20.0 g, 76.0 mmol), a sodium poly-D-glutamate modified at one of its ends by the molecule BA3 is obtained.

Dry extract: 15.2 mg/g
DP (estimated by $^1$H NMR)=21, thus i=0.048.
The calculated average molecular weight of the co-polyamino acid BB22 is 3936 g/mol.
HPLC-aqueous SEC (calibrant PEG): Mn=2900 g/mol.

Example BB23: Co-Polyamino Acid BB23—a Random Copolymer of Unit Sodium D- or L-Glutamate, Modified at One of its Ends by the Molecule BA3 and Having a Number Average Molecular Weight (Mn) of 2800 g/mol γ-Benzyl-L-glutamate N-carboxyanhydride (20.0 g, 76.00 mmol) and γ-benzyl-D-glutamate N-carboxyanhydride (20.0 g, 76.00 mmol) are placed under a vacuum for 30 min in a round-bottom flask dried beforehand in the oven, then anhydrous DMF (75 mL) is introduced. The mixture is stirred under argon until the solubilization is complete, cooled to 4° C., then a solution of molecule BA3 in free amine form (5.55 g, 6.91 mmol) in chloroform (14.5 mL) is introduced rapidly. The mixture is stirred between 4° C. and room temperature for 18 h, then heated at 65° C. for 2 h. The reaction mixture is then cooled to room temperature, then poured dropwise into diisopropyl ether (1.2 L) under stirring. The white precipitate is recovered by filtration, washed three times with diisopropyl ether (80 mL), then dried under a vacuum at 30° C. until obtaining a white solid. The solid is diluted in TFA (152 mL), and a 33% hydrobromic acid (HBr) solution in acetic acid (106 mL, 220 mmol) is then added dropwise and at 0° C. The solution is stirred for 3 h at room temperature then poured dropwise onto a 1:1 (v/v) mixture of diisopropyl ether/water and under stirring (1.84 L). The aqueous phase is separated in a dropping funnel, and the pH is adjusted to 7.2 by addition of a 10 N aqueous NaOH solution. After addition of water (250 mL), the mixture is filtered through a 0.45-μm filter then purified by ultrafiltration against a 0.9% NaCl solution, then water until the conductimetry of the permeate is less than 50 μS/cm. The solution of co-polyamino acid is then concentrated to approximately 25 g/L, filtered through a 0.2-μm filter and stored at 4° C.

Dry extract: 28.2 mg/g.
DP (estimated by $^1$H NMR)=21, thus i=0.048.
The calculated average molecular weight of the co-polyamino acid BB23 is 3936 g/mol.
HPLC-aqueous SEC (calibrant PEG): Mn=2800 g/mol.

Example BB24: Co-Polyamino Acid BB24—a Block Copolymer of Sodium Poly-D-Glutamate and Sodium Poly-L-Glutamate, Modified at One of its Ends by the Molecule BA3 and Having a Number Average Molecular Weight (Mn) of 2800 g/mol γ-Benzyl-D-glutamate N-carboxyanhydride (13.5 g, 51.3 mmol) is placed under a vacuum for 30 min in a round-bottom flask dried beforehand in the oven, then anhydrous DMF (52 mL) is introduced. The mixture is stirred under argon until the solubilization is complete, cooled to 0° C., then a solution of molecule BA3 in free amine form (3.43 g, 4.27 mmol) in chloroform (8.6 mL) is introduced rapidly. The mixture is stirred at 0° C. for 24 h, then a solution of γ-tert-butyl-L-glutamate N-carboxyanhydride (13.5 g, 58.9 mmol) in DMF (15 mL) is added. The mixture is then stirred between 0° C. and room temperature for 21 h, then heated at 65° C. for 2 h. The reaction mixture is then cooled to room temperature, then poured dropwise into diisopropyl ether (0.8 L) under stirring. The white precipitate is recovered by filtration, washed three times with diisopropyl ether (53 mL), then dried under a vacuum at 30° C. until obtaining a white solid. The solid is diluted in TFA (96 mL), and a 33% hydrobromic acid (HBr) solution in acetic acid (68 mL, 388 mmol) is then added dropwise and at 0° C. The solution is stirred for 2 h at room temperature, then poured dropwise onto a 1:1 (v/v) mixture of diisopropyl ether/water and under stirring (1.2 L). After 2 h of stirring, the heterogeneous mixture is allowed to rest overnight. The white precipitate is recovered by filtration, washed successively with a 1:1 (v/v) mixture of diisopropyl ether and water (100 mL), then with water (100 mL). The solid obtained is solubilized in water (900 ml) by adjusting the pH to 7 by addition of a 10 N aqueous sodium hydroxide solution, then a 1N aqueous sodium hydroxide solution. The mixture is filtered through a 0.45-μm filter, then purified by ultrafiltration against a 0.9% NaCl solution, then water until the conductimetry of the permeate is less than 50 μS/cm. The solution of co-polyamino acid is then concentrated to approximately 20 g/L theoretical and the pH is adjusted to 7.0. The aqueous solution is filtered through a 0.2-μm filter and stored at 4° C.

Dry extract: 23.9 mg/g
DP (estimated by $^1$H NMR)=25, thus i=0.04
The calculated average molecular weight of the co-polyamino acid BB24 is 4541 g/mol.

HPLC-aqueous SEC (calibrant PEG): Mn=2800 g/mol.

Example BB25: Co-Polyamino Acid
BB25—Sodium Poly-L-Glutamate Modified at One of its Ends by the Molecule BA5 and Having a Number Average Molecular Weight (Mn) of 2800 g/mol By a method similar to the one used for the preparation of the co-polyamino acid BB14 applied to the molecule BA5 in free amine form (1.70 g, 1.98 mmol) and of γ-benzyl-L-glutamate N-carboxyanhydride (11.46 g. 43.5 mmol), a sodium-L-glutamate modified at one of its ends by the molecule BA5 is obtained.

Dry extract: 19.8 mg/g
DP (estimated by $^1$H NMR)=23, thus i=0.043
The calculated average molecular weight of the co-polyamino acid BB25 is 4295 g/mol.
HPLC-aqueous SEC (calibrant PEG): Mn=2800 g/mol.

Example BB26: Co-Polyamino Acid
BB26—Sodium Poly-L-Glutamate Modified at One of its Ends by the Molecule BA6 and Having a Number Average Molecular Weight (Mn) of 2900 g/mol By a method similar to the one used for the preparation of the co-polyamino acid BB14 applied to the molecule BA6 in free amine form (3.05 g, 4.01 mmol) and of γ-benzyl-L-glutamate N-carboxyanhydride (22.78 g, 86.5 mmol), a sodium poly-L-glutamate modified at one of its ends by the molecule BA6 is obtained.

Dry extract: 16.9 mg/g
DP (estimated by $^1$H NMR)=21, thus i=0.048
The calculated average molecular weight of the co-polyamino acid BB26 is 3894 g/mol.
HPLC-aqueous SEC (calibrant PEG): Mn=2900 g/mol.

Example BB27: Co-Polyamino Acid
BB27—Sodium Poly-L-Glutamate Modified at One of its Ends by the Molecule BA3 and Modified by the Molecule BA3 and Having a Number Average Molecular Weight (Mn) of 2300 g/mol Co-polyamino acid BB27-1: poly-L-glutamic acid having a number average molecular weight (Mn) of 3600 g/mol modified at one of its ends by the molecule BA3 and capped at the other end by pidolic acid.

γ-Benzyl-L-glutamate N-carboxyanhydride (122.58 g, 466 mmol) is placed under vacuum for 30 min in a round-bottom flask dried beforehand in the oven, then anhydrous DMF (220 mL) is introduced. The mixture is stirred under argon until the solubilization is complete, cooled to −10° C., then a solution of molecule BA3 in free amine form (17.08 g, 21.3 mmol) in chloroform (40 mL) is introduced rapidly. The mixture is stirred between 0° C. and room temperature for 2 days, then heated at 65° C. for 4 h. The reaction mixture is then cooled to 25° C., then pidolic acid (13.66 g, 105.8 mmol), HOBt (2.35 g, 15.3 mmol) and EDC (20.28 g, 105.8 mmol) are added. After 24 h of stirring at 25° C., the solution is concentrated under a vacuum in order to eliminate the chloroform and 50% of the DMF. The reaction medium is then heated at 55° C., and 1150 mL of methanol are introduced within 1 h. The reaction mixture is then cooled to 0° C. After 18 h, the white precipitate is recovered by filtration, washed three times with 270 mL of diisopropyl ether, then dried under a vacuum at 30° C. until obtaining a white solid. The solid is diluted in TFA (390 mL), and a 33% hydrobromic acid (HBr) solution in acetic acid (271 mL, 1547 mmol) is then added dropwise and at 0° C. The solution is stirred for 2 h at room temperature, then it is poured dropwise onto a 1:1 (v/v) mixture of diisopropyl ether/water and under stirring (970 mL). After 2 h of stirring, the heterogeneous mixture is left to rest overnight. The white precipitate is recovered by filtration, washed successively with diisopropyl ether (380 mL), then two times with water (380 mL). The solid obtained is solubilized in water (3.6 L) by adjusting the pH to 7 by addition of a 10 N aqueous sodium hydroxide solution, then a 1 N aqueous sodium hydroxide solution. The mixture is filtered through a 0.45-μm filter, then purified by ultrafiltration against a 0.9% NaCl solution, a 0.1 N NaOH solution, a 0.9% NaCl solution, a phosphate buffer solution (150 mM), a 0.9% NaCl solution, then water until the conductimetry of the permeate is less than 50 S/cm. The solution of co-polyamino acid is then concentrated to approximately 30 g/L theoretical, filtered through a 0.2-μm filter, then acidified to pH 2 under stirring by addition of a 37% HCl solution. The precipitate is then recovered by filtration, washed two times with water, then dried under a vacuum at 30° C. until obtaining a white solid.

Co-Polyamino Acid BB27

By a method similar to the one used for the preparation of the co-polyamino acid BB2 applied to the molecule BA3 in free amine form (1.206 g, 1.50 mmol) and to the co-polyamino acid BB27-1 (5.5 g, 33.4 mmol), a sodium poly-L-glutamate modified at one of its ends by the molecule BA3 and modified by the molecule BA3 is obtained.

Dry extract: 19.0 mg/g
DP (estimated based on $^1$H NMR): 22
Based on $^1$H NMR: i=0.089
The calculated average molecular weight of the co-polyamino acid BB27 is 4826 g/mol.
HPLC-aqueous SEC (calibrant PEG): Mn=2300 g/mol.

Example BB42: Co-Polyamino Acid
BB42—Sodium Poly-L-Glutamate Modified at One of its Ends by the Molecule B8 and Having a Number Average Molecular Weight (Mn) of 3200 g/mol DCC (0.659 g, 3.19 mmol) and NHS (0.365 g, 3.17 mmol) are added to a solution of molecule B8 (2.366 g, 3.11 mmol) in DMF (19.5 mL). After 16 h of stirring at room temperature, the solution is filtered to be used directly in the following reaction.

γ-Benzyl-L-glutamate N-carboxyanhydride (18.0 g, 68.4 mmol) is placed under a vacuum for 30 min in a round-bottom flask dried beforehand in the oven, then anhydrous DMF (40 mL) is introduced. The mixture is then stirred under argon until the dissolution is complete, cooled to 0° C., then hexylamine (0.411 mL, 3.11 mmol) is introduced rapidly. After 30 h of stirring at 0° C., the solution of molecule B8 prepared above is added. The solution is stirred between 0° C. and room temperature for 72 h, then poured dropwise into diisopropyl ether (0.9 L) under stirring. The precipitate is recovered by filtration, washed with diisopropyl ether (5 times 100 mL), then dried under a vacuum at 30° C. to yield a white solid. The solid is diluted in TFA (69 mL), then the solution is cooled to 4° C. A 33% HBr solution in acetic acid (48 mL, 0.274 mol) is then added dropwise. The mixture is stirred at room temperature for 2 h, then poured dropwise onto a 1:1 (v/v) mixture of diisopropyl ether and water under stirring (0.8 L). After 2 h of stirring, the heterogeneous mixture is left to rest overnight. The white precipitate is recovered by filtration, washed with a 1:1 (v/v) mixture of diisopropyl ether and water (70 mL), then with water (70 mL). The solid obtained is then solubilized in water (0.42 L) by adjusting the pH to 7 by addition of a 10 N aqueous sodium hydroxide solution, then a 1 N aqueous sodium hydroxide solution. After solubilization, the theoretical concentration is adjusted to 20 g/L theoretical by addition of water until obtaining a final volume of 0.63 L. The solution is filtered through a 0.45-μm filter, then purified by ultrafiltration against a 0.9% NaCl solution, then water until the conductimetry of the permeate is less than 50 μS/cm. The solution obtained is filtered through a 0.2-μm filter and stored at 2-8° C.

Dry extract: 22.2 mg/g
DP (estimated based on $^1$H NMR): 22
Based on $^1$H NMR: i=0.045
The calculated average molecular weight of the co-polyamino acid BB42 is 4160 g/mol.
HPLC-aqueous SEC (calibrant PEG): Mn=3200 g/mol.

Example BB43: Co-Polyamino Acid BB43—Sodium Poly-L-Glutamate Modified at One of its Ends by the Molecule BA3 and at the Other End by the Molecule B8 and Having a Number Average Molecular Weight (Mn) of 2000 g/mol DCC (0.257 g, 1.24 mmol) and NHS (0.143 g, 1.24 mmol) are added to a solution of molecule B8 (0.946 g, 1.24 mmol) in DMF (8 mL). After 16 h of stirring at room temperature, the solution is filtered to be used directly in the following reaction.

γ-Benzyl-L-glutamate N-carboxyanhydride (6.0 g, 22.8 mmol) is placed under a vacuum for 30 min in a round-bottom flask dried beforehand in the oven, then anhydrous DMF (14 mL) is introduced. The mixture is then stirred under argon until the dissolution is complete, cooled to 0° C., then a solution of molecule BA3 in free amine form (0.832 g, 1.04 mmol) in chloroform (2.0 mL) is introduced rapidly. After 18 h of stirring at 0° C., the solution of molecule B8 prepared beforehand is added. The solution is stirred between 0° C. and room temperature for 22 h, then poured dropwise into diisopropyl ether (0.34 L) under stirring. The precipitate is recovered by filtration, washed with diisopropyl ether (7 times 15 mL), then dried under a vacuum at 30° C. to yield a white solid. The solid is diluted in TFA (23 mL), then the solution is cooled to 4° C. A 33% HBr solution in acetic acid (15 mL, 85.7 mmol) is then added dropwise. The mixture is stirred at room temperature for 2 h, then poured dropwise onto a 1:1 (v/v) mixture of diisopropyl ether and water under stirring (0.28 L). After 2 h of stirring, the heterogeneous mixture is allowed to rest overnight. The white precipitate is recovered by filtration, washed two times with a 1:1 (v/v) mixture of diisopropyl ether and water (24 mL), then two times with water (24 mL). The solid obtained is then solubilized in water (0.16 L) by adjusting the pH to 12 by addition of a 10 N aqueous sodium hydroxide solution, then a 1 N aqueous sodium hydroxide solution. After 30 minutes, the pH is adjusted to 7 by slow addition of a 1 N aqueous HCl solution. The solution is filtered through a 0.45-μm filter, then purified by ultrafiltration against a 0.9% NaCl solution, then water until the conductimetry of the permeate is less than 50 μS/cm. The solution obtained is filtered through a 0.2-μm filter and stored at 2-8° C.

Dry extract: 18.9 mg/g
DP (estimated based on $^1$H NMR): 22
Based on $^1$H NMR: $i_1$=0.09
The calculated average molecular weight of the co-polyamino acid BB43 is 4871 g/mol.
HPLC-aqueous SEC (calibrant PEG): Mn=2000 g/mol.

Example BB44: Co-Polyamino Acid BB44—Sodium Poly-L-Glutamate Modified at One of its Ends by the Molecule BA7 and Having a Number Average Molecular Weight (Mn) of 3300 g/mol By a method similar to the one used for the preparation of the co-polyamino acid BB14 applied to molecule BA7 in free amine form (4.45 g, 5.18 mmol) and to 30.0 g (113.96 mmol) of γ-benzyl-L-glutamate N-carboxyanhydride, a sodium poly-L-glutamate modified at one of its ends by molecule BA7 is obtained.

Dry extract: 29.0 mg/g
DP (estimated by $^1$H NMR)=25 thus i=0.04
The calculated average molecular weight of the co-polyamino acid BB44 is 4597 g/mol.
HPLC-aqueous SEC (calibrant PEG): Mn=3300 g/mol.

Part CE: Counter-Example Co-Polyamino Acids
CEA: Synthesis of the Counter-Example Hydrophobic Molecules TABLE 1f Counter-example hydrophobic molecules

CEA1

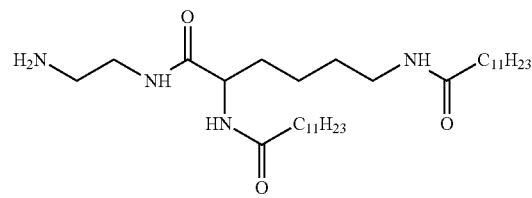

TABLE 1f-continued

Counter-example hydrophobic molecules

CEA2

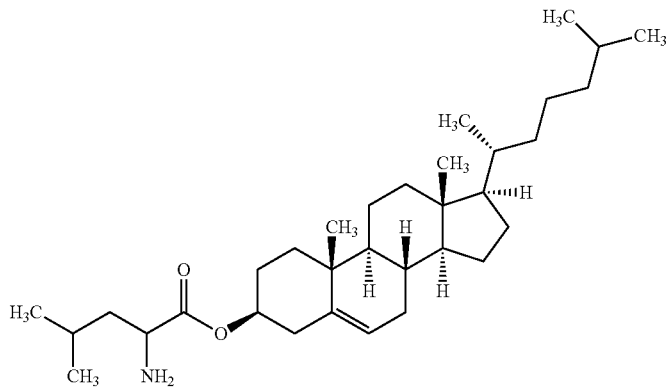

CEA3

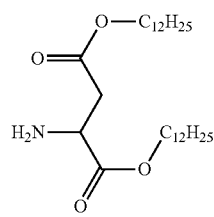

Example CEA1: Molecule CEA1

Molecule CE1; Product Obtained by the Reaction Between Lauric Acid and L-Lysine

By a method similar to the one used for the preparation of molecule B1 applied to lauric acid (19.58 g, 97.72 mmol) and to L-lysine (7.5 g, 51.3 mmol), a beige solid is obtained.

Yield: 18.8 g (75%)

$^1$H NMR (DMSO-d6, ppm): 0.85 (6H); 1.12-1.78 (42H); 1.96-2.16 (4H); 2.92-3.07 (2H); 4.06-4.20 (1H); 7.70 (1H); 7.95 (1H); 12.40 (1H)

LC/MS (ESI): 511.5; (calculated ([M+H]$^+$): 511.8).

Molecule CE2 Product Obtained by the Reaction Between Molecule CE1 and Boc-Ethylenediamine By a method similar to the one used for the preparation of molecule B3 applied to molecule CE1 (18.70 g, 36.61 mmol), the residue obtained after concentration at reduced pressure of the reaction medium is triturated in an acetonitrile/THF mixture (1/1 vol.), filtered and washed with acetonitrile. After drying, a pale yellow solid is obtained.

Yield: 13.7 g (57%)

$^1$H NMR (CDCl$_3$, ppm): 0.87 (6H); 1.09-1.89 (51H); 2.08-2.31 (4H); 3.13-3.48 (6H); 4.35 (1H); 5.20 (1H); 5.85 (1H); 6.46 (11H); 6.94 (1H). LC/MS (ESI): 653.5; (calculated ([M+H]$^+$): 654.0).

Molecule CEA1

After a method similar to the one used for the preparation of molecule BA1 applied to molecule CE2 (22.2 g, 34 mmol), the residue obtained after concentration under a vacuum is recrystallized in hot methanol. After cooling to room temperature, the solid is filtered, washed with cold methanol, then acetone, and dried under a vacuum to yield a pale yellow solid.

Yield: 16.3 g (81%).

$^1$H NMR (MeOD, ppm): 0.90 (6H); 1.20-1.85 (42H); 2.15-2.30 (4H); 3.06 (2H); 3.19 (2H); 3.40 (1H); 3.55 (1H); 4.13 (1H)

LC/MS (ESI): 553.5; (calculated ([M+H]$^+$): 553.9).

Molecule CEA2 and Molecule CEA3

Molecules CEA2 and CEA3 were synthesized according to the protocol described in the patent U.S. Pat. No. 4,826,818 (Kenji M. et al.).

Part CEB: Synthesis of the Counter-Example Co-Polyamino Acids
TABLE 1g
counter-example co-polyamino acids
CEB1
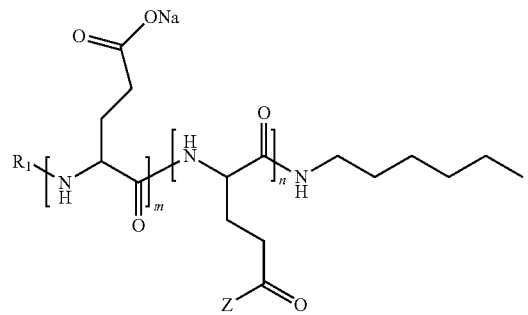
$i = 0.024$, DP $(m + n) = 42$
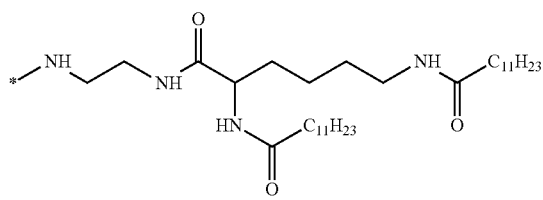
Z =
$R_1$ = H or pyroglutamate
CEB2
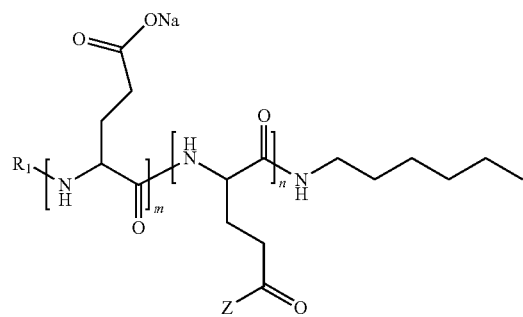
$i = 0.05$, DP $(m + n) = 22$
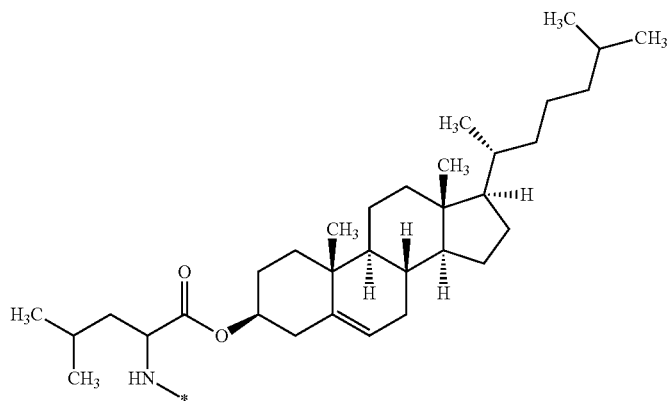
Z =
$R_1$ = $CH_3$—CO—, H or pyroglutamate TABLE 1g-continued
| counter-example co-polyamino acids |
|---|
CEB3
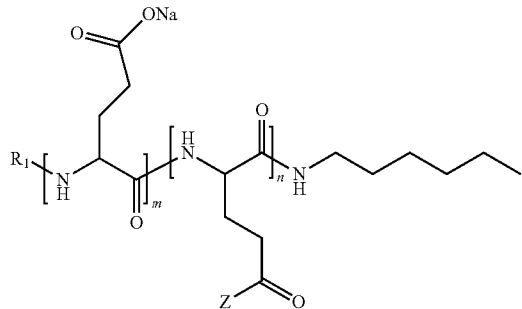
i = 0.05, DP (m + n) = 43
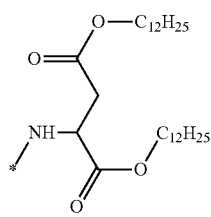
Z =
R₁ = CH₃—CO—, H or pyroglutamate
CEB4
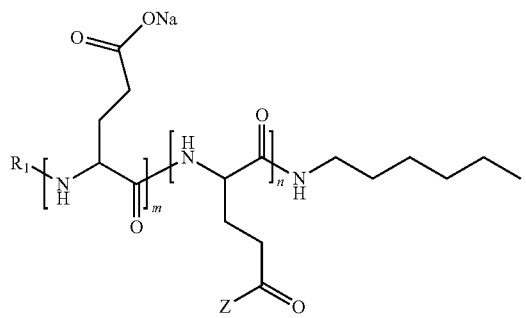
i = 0.05, DP (m + n) = 20
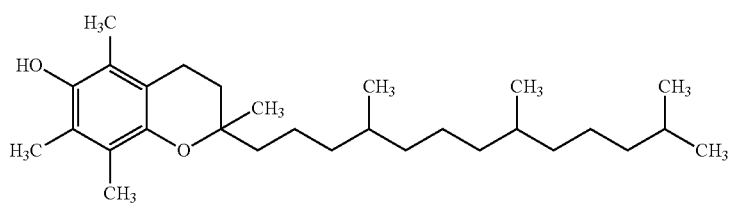
Z =
R₁ = H or pyroglutamate TABLE 1g-continued counter-example co-polyamino acids

CEBX4

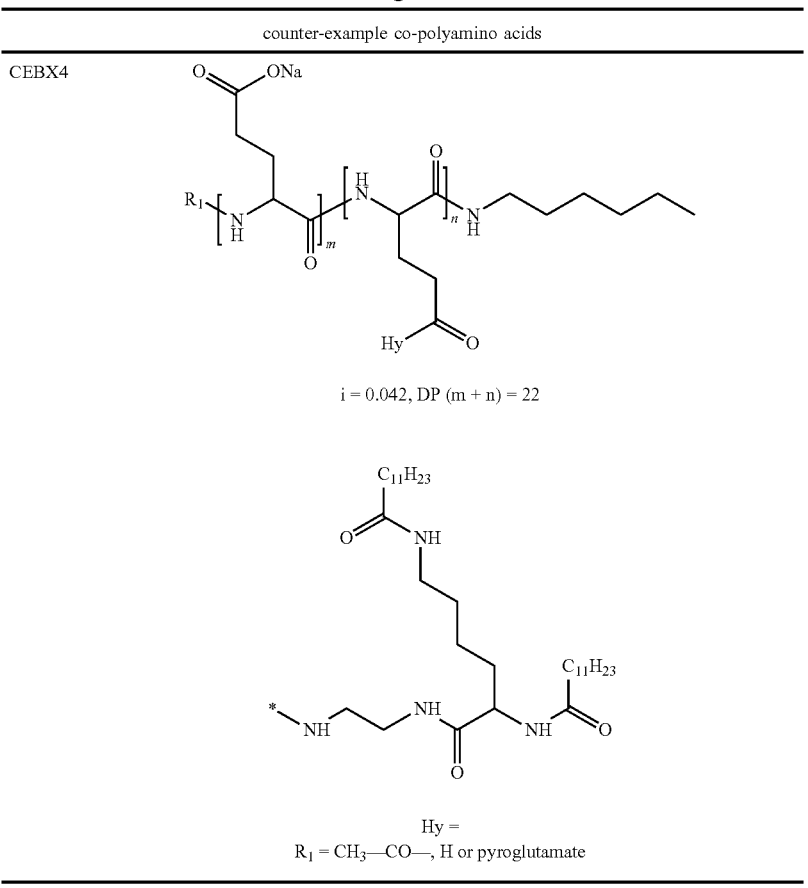

i = 0.042, DP (m + n) = 22

Hy =
$R_1 = CH_3—CO—$, H or pyroglutamate

Example CEB1: Co-Polyamino Acid CEB1—Sodium Poly-L-Glutamate Modified by Molecule CEA and Having a Number Average Molecular Weight of 3800 g/mol A poly-L-glutamic acid having a number average molecular weight (Mn) of 8500 g/mol (2.0 g) obtained by a method similar to the one used for the preparation of the co-polyamino acid BB1-1 is solubilized in DMF (27 mL) at 30-40° C., then the solution is cooled to 0° C. To this solution, a solution of EDC (0.59 g, 3.06 mmol) in DMF (6 mL), a solution of HOBt (0.41 g, 3.06 mmol) in DMF (1 mL), and DIPEA (1.76 mL, 18.3 mmol) are added. A solution of molecule CEA1 (0.21 g, 1.84 mmol) in DMF (0.9 mL) is then added, and the mixture is stirred at 25° C. for 3 h. The reaction medium is diluted with 11 mL of water added dropwise, then purified by dialysis against a 0.9% aqueous NaCl solution, then water. The solution obtained is filtered through a 0.2-µm filter and stored at 2-8° C.

Dry extract: 16.3 mg/g.

DP (estimated based on $^1$H NMR): 42.

Based on $^1$H NMR: i=0.024.

The calculated average molecular weight of the co-polyamino acid CEB1 is 6924 g/mol.

HPLC-aqueous SEC (calibrant PEG): Mn=3800 g/mol.

Example CEB2: Co-Polyamino Acid CEB2—Sodium Poly-L-Glutamate Capped at One of its Ends by an Acetyl Group and Modified by Cholesteryl Leucinate and Having a Number Average Molecular Weight of 2575 g/mol The para-toluenesulfonic acid salt of cholesteryl leucinate is prepared according to the method described in the patent U.S. Pat. No. 4,826,818 (Kenji, M. et al.).

By a method similar to the one used for the preparation of the co-polyamino acid BB13 applied to the para-toluenesulfonic acid salt of cholesteryl leucinate (1.23 g, 1.8 mmol) and to a poly-L-glutamic acid having a number average weight Mn=3600 g/mol (5 g) obtained by a method similar to the one used for the preparation of the co-polyamino acid BB5-1, a sodium poly-L-glutamate capped at one of its ends by an acetyl group and modified by cholesteryl leucinate is obtained.

Dry extract: 15.4 mg/g.

DP (estimated by $^1$H NMR): 22.

Based on $^1$H NMR: i=0.05.

The calculated average molecular weight of the co-polyamino acid CEB2 is 3973 g/mol.

HPLC-aqueous SEC (calibrant PEG): Mn=2575 g/mol.

Example CEB3: Co-Polyamino Acid CEB3—Sodium Poly-L-Glutamate Capped at One of its Ends by an Acetyl Group and Modified by Dilauryl Aspartate and Having a Number Average Molecular Weight of 5820 g/mol The para-toluenesulfonic acid salt of dilauryl aspartate is prepared according to the method described in the patent U.S. Pat. No. 4,826,818 (Kenji, M. et al.).

By a method similar to the one used for the preparation of the co-polyamino acid BB13 applied to the para-toluenesulfonic acid salt of dilauryl aspartate (0.89 g, 1.9 mmol) and to a poly-L-glutamic acid having a number average weight Mn=8500 g/mol (5 g) obtained by a method similar to the one used for the preparation of the co-polyamino acid BB5-1, a sodium poly-L-glutamate capped at one of its ends by an acetyl group and modified by dilauryl aspartate is obtained.

Dry extract: 19.3 mg/g.
DP (estimated by $^1$H NMR): 43.
Based on $^1$H NMR: i=0.05.
The calculated average molecular weight of the co-polyamino acid CEB3 is 7565 g/mol.
HPLC-aqueous SEC (calibrant PEG): Mn=5820 g/mol.

Example CEB4: Co-Polyamino Acid CEB4—Sodium Poly-L-Glutamate Modified by (±)-Alpha-Tocopherol and Having a Number Average Molecular Weight of 5085 g/mol By a method similar to the one described in patent FR 2,840,614 (Ping, C. U. et al.) applied to (±)-alpha-tocopherol (0.5 g, 1.16 mmol) and to a poly-L-glutamic acid (3 g) obtained by a method similar to the one described in the patent FR2985429A1, a sodium poly-L-glutamate modified by (±)-alpha-tocopherol is obtained.

Dry extract: 10.9 mg/g.
DP (estimated by $^1$H NMR): 20.
Based on $^1$H NMR: i=0.05.
The calculated average molecular weight of the co-polyamino acid CEB4 is 3473 g/mol.
HPLC-aqueous SEC (calibrant PEG): Mn=5085 g/mol.

Example CEBX4: Co-Polyamino Acid CEBX4—Sodium Poly-L-Glutamate Capped at One of its Ends by an Acetyl Group and Modified by Molecule CEA1 and Having a Number Average Molecular Weight (Mn) of 3300 g/mol By a method similar to the one used for the preparation of the co-polyamino acid BB2 applied to the hydrochloride salt of molecule CEA1 (0.918 g, 1.56 mmol) and to a poly-L-glutamic acid having a number average weight Mn=3700 g/mol (5.0 g) obtained by a method similar to the one used for the preparation of the co-polyamino acid BB5-1, a sodium poly-L-glutamate capped at one of its ends by an acetyl group and modified by molecule CEA1 is obtained.

Dry extract: 17.4 mg/g
DP (estimated based on $^1$H NMR): 22
Based on $^1$H NMR: i=0.042.
The calculated average molecular weight of the co-polyamino acid CEBX4 is 3941 g/mol.
HPLC-aqueous SEC (calibrant PEG): Mn=3300 g/mol.

Part C—Insulin Glargine, Prandial Insulin or GLP-1 RA Compositions

Example C1: Solution of Rapid Insulin Analog (Humalog®) at 100 U/mL

This solution is a commercial solution of insulin lispro marketed by the company ELI LILLY under the name of Humalog®. This product is a rapid insulin analog. The excipients in Humalog® are meta-cresol (3.15 mg/mL), glycerol (16 mg/mL), disodium phosphate (1.88 mg/mL), zinc oxide (to obtain 0.0197 mg of zinc ion/mL), sodium hydroxide and hydrochloric acid for the adjustment of the pH (pH 7-7.8), and water.

Example C2: Solution of Rapid Insulin Analog (NovoLog®) at 100 U/mL

This solution is a commercial solution of insulin aspart marketed by the company NOVO NORDISK under the name of NovoLog® in the United States of America and Novolog® in Europe. This product is a rapid insulin analog. The excipients of Novolog® are glycerol (16 mg), phenol (1.50 mg/mL), meta-cresol (1.72 mg/mL), zinc (19.6 μg/mL), disodium phosphate dihydrate (1.25 mg/mL), sodium chloride (0.5 mg/mL), sodium hydroxide and hydrochloric acid for the adjustment of the pH (pH 7.2-7.6), and water.

Example C3: Solution of Rapid Insulin Analog (Apidra®) at 100 U/mL

This solution is a commercial solution of insulin glulisine marketed by the company SANOFI under the name of Apidra®. This product is a rapid insulin analog. The excipients of Apidra® are meta-cresol (3.15 mg/mL), tromethamine (6 mg/mL), sodium chloride (5 mg/mL), polysorbate 20 (0.01 mg/mL), sodium hydroxide and hydrochloric acid for the adjustment of the pH (pH 7.3), and water.

Example C4: Solution of Slow-Acting Insulin Analog (Lantus®) at 100 U/mL

This solution is a commercial solution of insulin glargine marketed by the company SANOFI under the name of Lantus®. This product is a slow-acting insulin analog. The excipients in Lantus® are zinc chloride (30 μg/mL), meta-cresol (2.7 mg/mL), glycerol (85%) (20 mg/mL), sodium hydroxide and hydrochloric acid for the adjustment of the pH (pH 4), and water.

Example C5: Solution of Human Insulin (ActRapid®) at 100 IU/mL

This solution is a commercial solution of human insulin from NOVO NORDISK sold under the name of ActRapid®. This product is a human insulin. The excipients of ActRapid® are zinc chloride, glycerol, meta-cresol, sodium hydroxide and hydrochloric acid for the adjustment of the pH (pH 6.9-7.8), and water.

Example C6: Solution of Human Insulin (Umuline Rapide®) at 100 IU/mL

This solution is a commercial solution of human insulin from ELI LILLY sold under the name of Umuline Rapide®. This product is a human insulin. The excipients of Umuline Rapide® are glycerol, meta-cresol, sodium hydroxide and hydrochloric acid for the adjustment of the pH (pH 7.0-7.8), and water.

Example D1: Solution of GLP-1 RA Dulaglutide (Trulicity®) at 3 mg/mL

This solution is a solution of dulaglutide marketed by the company ELI LILLY under the name of Trulicity®. The excipients in Trulicity® are anhydrous citric acid (0.14 mg/mL), mannitol (46.4 mg/mL), polysorbate 80 (0.20 mg/mL), trisodium citrate dihydrate (2.74 mg/mL), and water.

Example D2: Solution of GLP-1 RA Exenatide (Byetta®) at 0.25 mg/mL

This solution is a solution of exenatide marketed by the company ELI LILLY under the name of Byetta®. The excipients in Byetta® are meta-cresol (20 mM), mannitol, glacial acetic acid, sodium acetate trihydrate, and water.

Example D3: Solution of GLP-1 RA Liraglutide (Victoza®) at 6 mg/mL

This solution is a solution of liraglutide marketed by the company NOVO NORDISK under the name of Victoza®. The excipients in Victoza® are disodium phosphate dihydrate, propylene glycol (1.42 mg/mL), phenol (5.5 mg/mL), and water.

Example D4: Solution of GLP-1 RA Lixisenatide (Lyxumia®) at 0.1 mg/mL

This solution is a solution of lixisenatide marketed by the company SANOFI under the name of Lyxumia®. The excipients in Lyxumia® are glycerol, sodium acetate, methionine, meta-cresol (25 mM), hydrochloric acid and sodium hydroxide for the adjustment of the pH, and water.

Example D5: Solution of GLP-1 RA Albiglutide (Tanzeum®) at 60 mg/mL

Albiglutide is presented in a solid form to be reconstituted, marketed by the company GSK under the name of Tanzeum®. In an injection device, the powder and the volume of water required for the solubilization, which initially are in separate compartments, are mixed by actuating the pen by rotation of the distal end of the device until a characteristic "click" noise is obtained. The solution is ready for the injection after a procedure consisting of mixing steps and resting times described in the user instructions for the product. The excipients in Tanzeum® are mannitol (153 mM), polysorbate 80 (0.01% w/w), sodium phosphate (10 mM), trehalose dihydrate (117 mM).

I. Determination of the Minimum Ratios for Solubilizing Insulin Glargine

Example G3: Protocol for the Determination of the Minimum Concentration for Solubilizing Insulin Glargine at 50 U/mL at pH 7

Concentrated solutions of m-cresol and of glycerol are added to a stock solution of co-polyamino acid at pH 7 in a manner so as to obtain a solution of co-polyamino acid of concentration $C_{co\text{-}polyamino\ acid\ stock/excipients}$ (mg/mL). The quantity of excipients added is adjusted in a manner so as to obtain a concentration of m-cresol of 35 mM and of glycerol of 184 mM in the composition of co-polyamino acid/insulin glargine 50 U/mL at pH 7.1.

In a 3-mL vial, 0.5 mL of a commercial solution of insulin glargine marketed under the name of Lantus® at a concentration of 100 U/mL is added to a volume of 0.5 mL of a solution of co-polyamino acid at concentration $C_{co\text{-}polyamino\ acid\ stock/excipients}$ (mg/mL) in a manner so as to obtain a composition $C_{co\text{-}polyamino\ acid}$ (mg/mL)/insulin glargine 50 U/mL at pH 7.1. Turbidity appears. The pH is adjusted to pH 7.1 by addition of concentrated NaOH, and the solution is placed under static conditions in an oven at 40° C. for 1 night. This operation is carried out for different concentrations of $C_{co\text{-}polyamino\ acid\ stock/excipients}$ (mg/mL) in a manner so as to vary the concentration of co-polyamino acid $C_{co\text{-}polyamino\ acid}$ (mg/mL) in steps of at most 0.25 mg/mL. After the night at 40° C., the samples are inspected visually and subjected to a static light scattering measurement at an angle of 173° using a zetasizer (Malvern). The minimum concentration of co-polyamino acid enabling the solubilization of insulin glargine is defined as the lowest concentration at which the mixture of co-polyamino acid/insulin glargine at pH 7 is visually clear and presents a scattered intensity of less than 3000 kcps/s.

TABLE 2

Minimum ratios for solubilizing insulin glargine.

| co-polyamino acid | Concentration of co-polyamino acid (mg/mL) at the threshold of solubilization of glargine 50 U/mL at pH 7 | [Hy]/[glargine] ratio (mol/mol) at the threshold of solubilization |
|---|---|---|
| BB7 | <1.5 | <1.5 |
| BB5 | <2 | <1.5 |
| BB3 | <2 | <1.5 |
| BB14 | <2 | <1.5 |
| BB10 | <1.5 | <1 |
| BB15 | <1.5 | <1 |
| BB11 | <1.5 | <1 |
| BB16 | <1.5 | <1 |
| AB6 | <2 | <1 |
| AB21 | <1.5 | <1.5 |
| AB17 | <1.5 | <1 |
| AB18 | <1.5 | <1 |
| BB17 | <2 | <1 |
| BB18 | <1.5 | <1 |
| BB20 | <1 | <1 |
| BB21 | <1.5 | <1.5 |
| BB22 | <1 | <1 |
| BB23 | <1 | <1 |
| BB24 | <1 | <1 |
| BB25 | <1 | <1 |
| BB26 | <1 | <1 |
| BB27 | <1.5 | <2 |
| BB42 | <1 | <1 |
| BB43 | <2 | <1 |

II. Solubilization/Precipitation a) Compositions Comprising Insulin Glargine

Preparation Method CA1: Preparation of a Diluted Composition of Co-Polyamino Acid/Insulin Glargine 50 U/mL at pH 7.1, According to a Method Using Insulin Glargine in Liquid Form (in Solution) and a Co-Polyamino Acid in Liquid Form (in Solution).

Concentrated solutions of m-cresol and of glycerol are added to a stock solution of co-polyamino acid at pH 7.1 in a manner so as to obtain a solution of co-polyamino acid of concentration $C_{co\text{-}polyamino\ acid\ stock/excipients}$ (mg/mL). The quantity of excipients added is adjusted in a manner so as to obtain a concentration of m-cresol of 35 mM and of glycerol of 184 mM in the composition of co-polyamino acid/insulin glargine 50 U/mL at pH 7.1.

In a sterile jar, a volume $V_{insulin\ glargine}$ of a commercial solution of insulin glargine marketed under the name of Lantus® at a concentration of 100 U/mL is added to a volume $V_{co\text{-}polyamino\ acid\ stock/excipients}$ of a solution of co-polyamino acid at concentration $C_{co\text{-}polyamino\ acid\ stock/excipients}$ (mg/mL) in a manner so as to obtain a diluted composition of co-polyamino acid $C_{diluted\ co\text{-}polyamino\ acid}$ (mg/mL)/insulin glargine 50 U/mL at pH 7.1.

Turbidity appears. The pH is adjusted to pH 7.1 by addition of concentrated NaOH, and the solution is placed under static conditions in an oven at 40° C. for 2 h until the solubilization is complete. This visually clear solution is placed at +4° C.

Preparation Method CA2: Preparation of a Concentrated Composition of Co-Polyamino Acid/Insulin Glargine at pH 7.1 with the Aid of a Co-Polyamino Acid, According to a Method for Concentrating a Diluted Composition.

A composition of co-polyamino acid/insulin glargine 50 U/mL at pH 7.1 described in Example CA1 is concentrated by ultrafiltration through a 3 kDa membrane made of regenerated cellulose (Amicon® Ultra-15 marketed by the company Millipore). After this ultrafiltration step, the retentate is clear, and the concentration of insulin glargine in the composition is determined by reverse phase chromatography (RP-HPLC). The concentration of insulin glargine in the composition is then adjusted to the desired value by dilution in a solution of excipients m-cresol/glycerol in a manner so as to obtain a final concentration of m-cresol of 35 mM and an osmolarity of 300 mOsm/kg. The pH is measured and adjusted to pH 7.1 by addition of concentrated NaOH and HCl. This solution at pH 7.1, visually clear, has a concentration of insulin glargine $C_{insulin\ glargine}$ (U/mL) and a concentration of co-polyamino acid $C_{co-polyamino\ acid}$ (mg/mL)=$C_{diluted\ co-polyamino\ acid}$ (mg/mL)×$C_{insulin\ glargine}$ (U/mL)/50 (U/mL).

According to this preparation method CA2, compositions of co-polyamino acid/insulin glargine were prepared, for example, with concentrations of insulin glargine of 200 U/mL and 400 U/mL.

Example CA3: Preparation of Compositions of Co-Polyamino Acid/Insulin Glargine 200 U/mL at pH 7.1

Compositions of co-polyamino acid/insulin glargine 200 U/mL are prepared according to the method described in Example CA2 in a manner so as to obtain a concentration of insulin glargine $C_{insulin\ glargine}$=200 U/mL and a concentration of co-polyamino acid $C_{co-polyamino\ acid}$ (mg/mL). These compositions are presented in the following Table 3.

Example CA4: Precipitation of Insulin Glargine in Compositions of Co-Polyamino Acid/Insulin Glargine at 200 U/mL 1 mL of solution of co-polyamino acid/insulin glargine prepared in Example CA3 is added to 2 mL of a PBS solution containing 20 mg/mL of BSA (bovine serum albumin). The PBS/BSA mixture simulates the composition of the subcutaneous environment. A precipitate appears.

A centrifugation at 4000 rpm is carried out in order to separate the precipitate from the supernatant. Next, the insulin glargine is assayed in the supernatant by RP-HPLC. The result is that insulin glargine is present in majority proportion in a precipitated form.

The results are presented in Table 3:

TABLE 3

Compositions of co-polyamino acid/insulin glargine (200 U/mL) prepared with the co-polyamino acids of the invention; solubilization/precipitation of insulin glargine.

| Composition | Insulin glargine (U/mL) | Co-polyamino acid | Concentration of co-polyamino acid (mg/mL) | Solubilization of insulin glargine | Precipitation of insulin glargine |
|---|---|---|---|---|---|
| CA3 | 200 | — | — | NO | na |
| CA3b | 200 | AB18 | 6 | YES | YES |
| CA3c | 200 | BB5 | 9 | YES | YES |
| CA3d | 200 | BB11 | 6 | YES | YES |
| CA3e | 200 | BB14 | 10 | YES | YES |
| CA3f | 200 | BB15 | 6 | YES | YES |
| CA3g | 200 | BB16 | 6 | YES | YES |
| CA3l | 200 | BB15 | 5 | YES | YES |
| CA3n | 200 | BB18 | 6 | YES | YES |
| CA3o | 200 | BB17 | 9 | YES | YES |
| CA3p | 200 | BB25 | 4.5 | YES | YES |
| CA3q | 200 | BB26 | 5 | YES | YES |
| CA3r | 200 | BB43 | 8 | YES | YES |
| CA3s | 200 | BB27 | 7 | YES | YES |
| CA3t | 200 | BB20 | 5 | YES | YES |
| CA3u | 200 | BB21 | 5 | YES | YES | b) Compositions Comprising Insulin Glargine and Insulin Lispro

Preparation Method CB1: Preparation of a Diluted Composition of Co-Polyamino Acid/Insulin Glargine 43 (U/mL)/Insulin Lispro 13.5 (U/mL)

A volume $V_{insulin\ lispro}$ of a commercial solution of insulin lispro Humalog® at 100 U/mL and water is added to a volume $V_{co-polyamino\ acid/diluted\ insulin\ glargine}$ of the diluted composition of co-polyamino acid/insulin glargine 50 U/mL at pH 7.1 described in Example CA1, in a manner so as to obtain a composition of co-polyamino acid/insulin glargine 43 (U/mL)/insulin lispro 13.5 (U/mL).

Preparation Method CB2: Preparation of a Composition of Co-Polyamino Acid/Insulin Glargine/Concentrated Insulin Lispro at pH 7.1

A composition of co-polyamino acid/insulin glargine 43 (U/mL)/insulin lispro 13.5 (U/mL) described in Example CB1 is concentrated by ultrafiltration through a 3 kDa membrane made of regenerated cellulose (Amicon® Ultra-15 marketed by the company MILLIPORE). After the completion of this ultrafiltration step, the retentate is clear, and the concentration of insulin glargine in the composition is determined by reverse phase chromatography (RP-HPLC). The concentrations of insulin glargine and insulin lispro in the composition are then adjusted to the desired value by dilution in a solution of excipients m-cresol/glycerol in a manner so as to obtain a final concentration of m-cresol of 35 mM and an osmolarity of 300 mOsm/kg. The pH is measured and adjusted if necessary to pH 7.1 by addition of concentrated NaOH and HCl. This solution at pH 7.1, visually clear, has a concentration of insulin glargine $C_{insulin\ glargine}$ (U/mL), a concentration of insulin lispro $C_{insulin\ lispro}$=$C_{insulin\ glargine}$×0.33, and a concentration of co-polyamino acid $C_{co-polyamino\ acid}$ (mg/mL)=$C_{diluted\ co-polyamino\ acid}$ (mg/mL)×$C_{insulin\ glargine}$ (U/mL)/50 (U/mL).

Example CB3: Preparation of Compositions of Co-Polyamino Acid/Insulin Glargine 200 U/mL/Insulin Lispro 66 U/mL at pH 7.1

Compositions of co-polyamino acid/insulin glargine 200 U/mL/insulin lispro 66 U/mL are prepared according to the method described in Example CB2 in a manner so as to obtain a concentration of insulin glargine $C_{insulin\ glargine}$=200 U/mL, a concentration of insulin lispro $C_{insulin\ lispro}$=66 U/mL, and a concentration of co-polyamino acid $C_{co-polyamino\ acid}$ (mg/mL). These compositions are presented in Table 4a.

Example CB4: Precipitation of Insulin Glargine in the Compositions of Co-Polyamino Acid/Insulin Glargine/Insulin Lispro at 200/66 U/mL 1 mL of solution of co-polyamino acid/insulin glargine/insulin lispro prepared in Example CB3 is added to 2 mL of a PBS solution containing 20 mg/mL of BSA (bovine serum albumin). The PBS/BSA mixture simulates the composition of the subcutaneous environment. A precipitate appears.

A centrifugation at 4000 rpm is carried out in order to separate the precipitate from the supernatant. Next, the insulin glargine is assayed in the supernatant by RP-HPLC. The result is that insulin glargine is found in majority proportion in a precipitated form. The results are presented in Tables 4a and 4b:

TABLE 4a

Compositions of co-polyamino acid/insulin glargine (200 U/mL)/insulin lispro (66 U/mL) prepared with the co-polyamino acids of the invention; solubilization and precipitation of insulin glargine.

| Composition | Insulin glargine (U/mL) | Insulin lispro (U/mL) | Co-polyamino acid | Concentration of co-polyamino acid (mg/mL) | Solubilization of insulin glargine | Precipitation of insulin glargine |
|---|---|---|---|---|---|---|
| CB3 | 200 | 66 | — | — | NO | na |
| CB3a | 200 | 66 | AB6 | 7 | YES | YES |
| CB3c | 200 | 66 | AB21 | 6 | YES | YES |
| CB3f | 200 | 66 | BB3 | 7 | YES | YES |
| CB3g | 200 | 66 | BB5 | 9 | YES | YES |
| CB3i | 200 | 66 | AB18 | 6 | YES | YES |
| CB3j | 200 | 66 | BB7 | 7 | YES | YES |
| CB3m | 200 | 66 | BB10 | 6 | YES | YES |
| CB3n | 200 | 66 | BB11 | 6 | YES | YES |
| CB3o | 200 | 66 | BB15 | 6 | YES | YES |
| CB3p | 200 | 66 | BB16 | 6 | YES | YES |
| CB3r | 200 | 66 | AB17 | 6 | YES | YES |
| CB3s | 200 | 66 | BB15 | 5 | YES | YES |
| CB3u | 200 | 66 | BB42 | 5 | YES | YES |
| CB3v | 200 | 66 | BB18 | 6 | YES | YES |
| CB3w | 200 | 66 | BB17 | 9 | YES | YES |
| CB3x | 200 | 66 | BB25 | 4.5 | YES | YES |
| CB3y | 200 | 66 | BB26 | 5 | YES | YES |
| CB3z | 200 | 66 | BB43 | 8 | YES | YES |
| CB3ab | 200 | 66 | BB27 | 7 | YES | YES |
| CB3ac | 200 | 66 | BB20 | 5 | YES | YES |
| CB3ad | 200 | 66 | BB21 | 5 | YES | YES |

Example CB5: Preparation of a Composition of Co-Polyamino Acid/Insulin Glargine 225 U/mL/Insulin Lispro 75 IU/mL at pH 7

Compositions of co-polyamino acid/insulin glargine 225 U/mL/insulin lispro 75 IU/mL are prepared according to the method described in Example CB2 in a manner so as to obtain a concentration of glargine $C_{insulin\ glargine}$=225 U/mL, a concentration of insulin lispro $C_{insulin\ lispro}$=75 IU/mL, and a concentration of co-polyamino acid $C_{co-polyamino\ acid}$ (mg/mL). These compositions are presented in Table 4b.

TABLE 4b

Compositions of co-polyamino acid/insulin glargine (225 U/mL)/insulin lispro (75 IU/mL) prepared with the co-polyamino acid BB14.

| Composition | Insulin glargine (U/mL) | Insulin lispro (IU/mL) | Co-polyamino acid | Concentration of co-polyamino acid (mg/mL) |
|---|---|---|---|---|
| CB5 | 225 | 75 | — | — |
| CB5f | 225 | 75 | BB14 | 10 |

Example CB6: Preparation of a Composition of Co-Polyamino Acid/Insulin Glargine 200 U/mL/Insulin Lispro 200 IU/mL at pH 7.1

Preparation Method CB7: Preparation of a Diluted Composition of Co-Polyamino Acid/Insulin Glargine 33 U/mL/Insulin Lispro 33 U/mL A volume $V_{insulin\ lispro}$ of a commercial solution of insulin lispro Humalog® at 100 U/mL and water is added to a volume $V_{co-polyamino\ acid/diluted\ insulin\ glargine}$ of the diluted composition of polyamino acid/insulin glargine 50 U/mL at pH 7.1 described in Example CA1, in a manner so as to obtain a composition of co-polyamino acid/insulin glargine 33 (U/mL)/insulin lispro 33 (U/mL).

Preparation Method CB8: Preparation of a Concentrated Composition of Co-Polyamino Acid/Insulin Glargine/Insulin Lispro Concentrated at pH 7.1

A composition of co-polyamino acid/insulin glargine 33 (U/mL)/insulin lispro 33 (U/mL) described in Example CB7 is concentrated by ultrafiltration through a 3 kDa membrane made of regenerated cellulose (Amicon® Ultra-15 marketed by the company MILLIPORE). After the completion of this ultrafiltration step, the retentate is clear, and the concentration of insulin glargine in the composition is determined by reverse phase chromatography (RP-HPLC). The concentrations of insulin glargine and insulin lispro in the composition are then adjusted to the desired value by dilution in a solution of excipients m-cresol/glycerol in a manner so as to obtain a final concentration of m-cresol of 35 mM and an osmolarity of 300 mOsm/kg. The pH is measured and adjusted if necessary to pH 7.1 by addition of concentrated NaOH and HCl. This solution at pH 7.1, visually clear, has a concentration of insulin glargine $C_{insulin\ glargine}$ (U/mL), a concentration of insulin lispro $C_{insulin\ lispro} = C_{insulin\ glargine}$, and a concentration of co-polyamino acid $C_{co-polyamino\ acid}$ (mg/mL)=$C_{diluted\ co-polyamino\ acid}$ (mg/mL)×$C_{insulin\ glargine}$ (U/mL)/50 (U/mL).

c) Compositions Comprising Insulin Glargine and Umuline Rapide Human Insulin

Example CB9: Preparation of a Composition of Co-Polyamino Acid/Insulin Glargine 200 U/mL/Human Insulin 66 IU/mL at pH 7.1

Preparation Method CB10: Preparation of a Diluted Composition of Co-Polyamino Acid/Insulin Glargine 43 (U/mL)/Human Insulin 13.5 (U/mL)

A volume $V_{human\ insulin}$ of a commercial solution of human insulin of Example C6 at 100 U/mL and water is added to a volume $V_{co-polyamino\ acid/diluted\ insulin\ glargine}$ of the diluted composition of co-polyamino acid/insulin glargine 50 (U/mL) at pH 7.1 described in Example CA1 in a manner so as to obtain a composition of co-polyamino acid/insulin glargine 43 (U/mL)/human insulin 13.5 (U/mL).
Preparation Method CB11: Preparation of a Concentrated Composition of Co-Polyamino Acid/Insulin Glargine/Human Insulin at pH 7.1

A composition of co-polyamino acid/insulin glargine 43 (U/mL)/human insulin 13.5 (U/mL) described in Example CB10 is concentrated by ultrafiltration through a 3 kDa membrane made of regenerated cellulose (Amicon® Ultra-15 marketed by the company MILLIPORE). After the completion of this ultrafiltration step, the retentate is clear, and the concentration of insulin glargine in the composition is determined by reverse phase chromatography (RP-HPLC). The concentrations of insulin glargine and human insulin in the composition are then adjusted to the desired value by dilution in a solution of excipients m-cresol/glycerol in a manner so as to obtain a final concentration of m-cresol of 35 mM and an osmolarity of 300 mOsm/kg. The pH is measured and adjusted if necessary to pH 7.1 by addition of concentrated NaOH and HCl. This solution at pH 7.1, visually clear, has a concentration of insulin glargine $C_{insulin\ glargine}$ (U/mL), a concentration of human insulin $C_{human\ insulin} = C_{human\ glargine} \times 0.33$, and a concentration of co-polyamino acid $C_{co-polyamino\ acid}$ (mg/mL)=$C_{diluted\ co-polyamino\ acid}$ (mg/mL)×$C_{insulin\ glargine}$ (U/mL)/50 (U/mL).

Example CB12: Preparation of Compositions of Co-Polyamino Acid/Insulin Glargine 200 U/mL/Human Insulin 66 U/mL at pH 7.1

Compositions of co-polyamino acid/insulin glargine 200 U/mL/human insulin 66 U/mL are prepared according to the method described in Example CB11 in a manner so as to obtain a concentration of insulin glargine $C_{insulin\ glargine}$=200 U/mL, a concentration of human insulin $C_{human\ insulin}$=66 U/mL, and a concentration of co-polyamino acid $C_{co-polyamino\ acid}$ (mg/mL). The composition is presented in Table 4c below.

TABLE 4c

Composition of co-polyamino acid/insulin glargine (200 U/mL) human insulin (66 IU/mL) at pH 7.1.

| | Insulin glargine (U/mL) | Human insulin (U/mL) | Co-polyamino acid | Concentration of co-polyamino acid (mg/mL) |
|---|---|---|---|---|
| CB12a | 200 | 66 | BB15 | 6 | d) Compositions Comprising Insulin Glargine and Dulaglutide

Example DB1: Preparation of a Composition of Insulin Glargine (50 U/mL)/Dulaglutide (0.25 mg/mL) at pH 7.1

0.833 mL of water are added to 0.167 mL of the solution of dulaglutide of Example D1, and the pH is adjusted to 4.1 mL of the solution of insulin glargine of Example C4 is then added to this solution in order to obtain 2 mL of a composition of which the pH is 4 in the mixture. The composition containing 50 U/mL of insulin glargine and 0.25 mg/mL of dulaglutide is clear, indicating the good solubility of insulin glargine and of dulaglutide under these formulation conditions (pH 4). The pH is then adjusted to 7.1 with a 0.1 N sodium hydroxide solution. The composition then becomes turbid, indicating the poor solubility of the composition of insulin glargine/dulaglutide at pH 7.1.

Example DB2: Preparation of a Composition of Insulin Glargine (50 U/mL)/Dulaglutide (0.25 mg/mL) at pH 7.1

0.833 mL of water are added to 0.167 mL of the solution of dulaglutide of Example D1. Then 1 mL of the solution of insulin glargine of Example C4 is added to this solution in order to obtain 2 mL of a composition of which the pH is 5.2 in the mixture. The composition containing 50 U/mL of insulin glargine and 0.25 mg/mL of dulaglutide is turbid, indicating the poor solubility of the composition of insulin glargine/dulaglutide at pH 5.2. The pH is then adjusted to 7.1 with a 0.1 N sodium hydroxide solution. The composition is still turbid, indicating the poor solubility of the composition of insulin glargine/dulaglutide at pH 7.1.

Example DB3: Preparation of Compositions of Co-Polyamino Acid/Insulin Glargine/Dulaglutide at pH 7.1

2 mL of the solution of dulaglutide of Example D1 and 1 mL of water are added to 3 mL of the solution of co-polyamino acid/insulin glargine prepared according to the protocol of Example CA2, in which the concentration of insulin glargine is 400 U/mL, in order to obtain 6 mL of a composition at pH 7. The pH is adjusted to 7.1 with a 0.1 N sodium hydroxide solution. The composition containing 7 mg/mL of co-polyamino acid AB6, 200 U/mL of insulin glargine, and 1 mg/mL of dulaglutide is clear, indicating the good solubility of insulin glargine and dulaglutide in the presence of the co-polyamino acid at pH 7.1. This clear solution is placed at +4° C. According to the protocol of Example DB3, the compositions with different co-polyamino acids are prepared and presented in Table 5 below.

Example DB4: Precipitation of Compositions of Co-Polyamino Acid/Insulin Glargine/Dulaglutide at pH 7.1

0.045 mL of composition of co-polyamino acid/insulin glargine/dulaglutide prepared according to the protocol of Example DB3 are added to 0.105 mL of a PBS solution containing 20 mg/mL of BSA. The PBS/BSA mixture simulates the composition of the subcutaneous environment. A precipitate appears.

A centrifugation at 4000 rpm is carried out in order to separate the precipitate from the supernatant. Then, the insulin glargine is assayed in the supernatant by RP-HPLC. The insulin glargine is found in a majority proportion in a precipitated form. The results are presented in the following Table 5.

TABLE 5

Compositions of co-polyamino acid/insulin glargine (200 U/mL)/dulaglutide (1 mg/mL); solubilization and precipitation of insulin glargine.

| Composition | Co-polyamino acid | Insulin glargine (U/mL) | Dulaglutide (mg/mL) | Co-polyamino acid (mg/mL) | Solubilization of insulin glargine | Precipitation of insulin glargine |
|---|---|---|---|---|---|---|
| DB1 | — | 50 | 0.25 | — | NO | na |
| DB2 | — | 50 | 0.25 | — | NO | na |
| DB3a | AB6 | 200 | 1 | 7 | YES | YES |
| DB3b | AB17 | 200 | 1 | 6 | YES | YES |
| DB3c | BB7 | 200 | 1 | 7 | YES | YES |
| DB3d | BB5 | 200 | 1 | 9 | YES | YES |
| DB3e | BB10 | 200 | 1 | 6 | YES | YES |
| DB3f | BB14 | 200 | 1 | 9 | YES | YES |
| DB3g | BB15 | 200 | 1 | 6 | YES | YES |

Example DB5: Preparation of Compositions of Co-Polyamino Acid/Insulin Glargine/Dulaglutide at pH 7.2

According to the protocol of Example DB3, the compositions with different co-polyamino acids are prepared at pH 7.2 and presented in Table 6 below.

TABLE 6

Compositions of co-polyamino acid/insulin glargine (200 U/mL)/dulaglutide (1 mg/mL) at pH 7.2.

| Composition | Co-polyamino acid | Insulin glargine (U/mL) | Dulaglutide (mg/mL) | Co-polyamino acid (mg/mL) |
|---|---|---|---|---|
| DB3h | BB10 | 200 | 1 | 6 |
| DB3i | BB15 | 200 | 1 | 6 |

Example DB6: Preparation of Compositions of Co-Polyamino Acid/Insulin Glargine at pH 7.2

According to the protocol of Example DB5 and starting with a solution equivalent to D1 containing the same excipients except anhydrous citric acid and without dulaglutide, the following composition is prepared at pH 7.2 and presented in the following Table 7.

TABLE 7

Compositions of co-polyamino acid/insulin glargine (200 U/mL) at pH 7.2.

| Composition | Co-polyamino acid | Insulin glargine (U/mL) | Dulaglutide (mg/mL) | Co-polyamino acid (mg/mL) |
|---|---|---|---|---|
| DB3k | BB15 | 200 | 0 | 5 | e) Preparation of a Composition of Co-Polyamino Acid/Insulin Glargine/Insulin Lispro/Exenatide Compositions of co-polyamino acid/insulin glargine/insulin lispro are prepared according to the method described in Examples CB2 and CB8. A volume of a solution of exenatide at 10 mg/mL prepared by dissolution of exenatide (Bachem) in water for injections is added to these solutions. The concentrations of insulin glargine, insulin lispro and exenatide in the composition are then adjusted to the desired value by dilution in a solution of excipients m-cresol/glycerol or m-cresol/glycerol/methionine in a manner so as to obtain a final concentration of m-cresol of 35 mM and an osmolarity of 300 mOsm/kg. The pH is measured and adjusted if necessary to pH 7.2 by addition of concentrated NaOH and HCl. These compositions are presented in Table 8.

TABLE 8

Compositions of co-polyamino acid/insulin glargine (200 U/mL)/lispro (67 IU/mL or 200 IU/mL/with or without exenatide.

| Composition | Insulin glargine (U/mL) | Insulin lispro (U/mL) | Co-polyamino acid | Concentration of co-polyamino acid (mg/mL) | Exenatide (µg/mL) | Methionine (mM) |
|---|---|---|---|---|---|---|
| CB2a | 200 | 67 | BB15 | 5 | 0 | 0 |
| CB2b | 200 | 67 | BB15 | 5 | 50 | 10 |
| CB2c | 200 | 67 | BB15 | 5 | 50 | 0 |
| CB8a | 200 | 200 | BB15 | 5 | 154 | 0 |

Part D'—Counter Examples
Preparation Protocols

Compositions of counter-example co-polyamino acid/insulin glargine 200 U/mL are prepared according to the method described in Example CA2 in a manner so as to obtain an insulin glargine concentration $C_{insulin\ glargine}=200$ U/mL and a concentration of counter-example co-polyamino acid $C_{counter-example\ co-polyamino\ acid}$ (mg/mL). These compositions are presented in the following Table 9.

TABLE 9

Compositions of counter-example co-polyamino acid/insulin glargine (200 U/mL).

| Composition | Insulin glargine (U/mL) | Co-polyamino acid | Concentration of co-polyamino acid (mg/mL) |
|---|---|---|---|
| CA3h | 200 | CEB1 | 13 |
| CA3i | 200 | CEB2 | 6 |
| CA3j | 200 | CEB3 | 7 |
| CA3k | 200 | CEB4 | 10 |
| CA3w | 200 | CEBX4 | 5 |

Compositions of co-polyamino acid/insulin glargine 200 U/mL/insulin lispro 66 U/mL are prepared according to the method described in Example CB2 in a manner so as to obtain an insulin glargine concentration Cinsulin glargine=200 U/mL, a concentration of insulin lispro Cinsulin lispro=66 U/mL and a concentration of counter-example co-polyamino acid Ccounter-example co-polyamino acid (mg/mL). These compositions are presented in the following Table 10.

TABLE 10

Counter-example compositions of co-polyamino acid/insulin glargine (200 U/mL)/insulin lispro (66 U/mL).

| Composition | Insulin glargine (U/mL) | Insulin lispro (U/mL) | Co-polyamino acid | Concentration of co-polyamino acid (mg/mL) |
|---|---|---|---|---|
| CB3s | 200 | 66 | CEB2 | 6 |
| CB3t | 200 | 66 | CEB3 | 7 |
| CB3af | 200 | 66 | CEBX4 | 5 |

According to Example CB12 (preparation of co-polyamino acid/insulin glargine 200 U/mL/human insulin 66 U/mL compositions at pH 7.1), co-polyamino acid/insulin glargine 200 U/mL/human insulin 66 U/mL compositions are prepared according to the method described in Example CB11 in a manner so as to obtain a concentration of insulin glargine Cinsulin glargine=200 U/mL, a concentration of human insulin Chuman insulin=66 U/mL and a concentration of co-polyamino acid Cco-polyamino acid (mg/mL). The composition is presented in the following Table 11.

TABLE 11

Counter-example co-polyamino acid/insulin glargine (200 U/mL)/human insulin (66 IU/mL) compositions at pH 7.1.

| | Insulin glargine (U/mL) | Human insulin (U/mL) | Co-polyamino acid | Concentration of co-polyamino acid (mg/mL) |
|---|---|---|---|---|
| CB12b | 200 | 66 | CEB2 | 6 |

According to the protocol of Example DB5, the compositions at pH 7.2 with different counter-example co-polyamino acids are prepared and presented in Table 12 below.

TABLE 12

Counter-example co-polyamino acid/insulin glargine (200 U/mL)/dulaglutide (0.8 or 1 mg/mL) compositions

| Composition | Co-polyamino acid | Insulin glargine (U/mL) | Dulaglutide (mg/mL) | Co-polyamino acid (mg/mL) |
|---|---|---|---|---|
| DB3x | CEB3 | 200 | 1 | 7 |
| DB3z | CEB2 | 200 | 1 | 6 |

III. Determination of the Quantity of Albumin Required to Obtain the Precipitation Example G1: Preparation of a Diluted Co-Polyamino Acid/Insulin Glargine 65 U/mL Composition at pH 7.1

Concentrated solutions of m-cresol and of glycerol are added to a stock solution of co-polyamino acid at pH 7 in a manner so as to obtain a solution of co-polyamino acid of concentration Cco-polyamino acid stock/excipients (mg/mL). The quantity of excipients added is adjusted in a manner so as to obtain a concentration of m-cresol of 35 mM and of glycerol of 184 mM in the co-polyamino acid/insulin glargine 65 U/mL composition at pH 7.1.

In a sterile jar, a volume $V_{insulin\ glargine}$ of a commercial solution of insulin glargine marketed under the name of Lantus® at a concentration of 100 U/mL is added to a volume $V_{co-polyamino\ acid\ stock/excipients}$ of a solution of co-polyamino acid of concentration $C_{co-polyamino\ acid\ stock/excipients}$ (mg/mL) in a manner so as to obtain a diluted co-polyamino acid composition $C_{diluted\ co-polyamino\ acid}$ (mg/mL)/insulin glargine 65 U/mL at pH 7.1. Turbidity appears. The pH is adjusted to pH 7.1 by addition of concentrated NaOH, and the solution is placed under static conditions in an oven at 40° C. for 2 h until the solubilization is complete. This visually clear solution is placed at +4° C.

Example G2: Precipitation of a Co-Polyamino Acid/Insulin Glargine 65 U/mL Composition at pH 7.1, by Varying the Concentration of Albumin 0.3 mL of a solution of BSA (bovine serum albumin) in a PBS buffer at pH 7.4 (phosphate buffer saline) and 1 mL of diluted co-polyamino acid/insulin glargine 65 U/mL composition, pH 7.1 are introduced, respectively in a disposable UV cuvette in a manner so as to obtain a mixture containing 50 U/mL insulin glargine, an albumin concentration CBSA (mg/mL) in a PBS buffer. Several solutions of BSA in a PBS buffer of variable concentrations are prepared so as to vary the concentration of albumin in the final mixture from 1 to 12.7 mg/mL (1; 2.9; 3.9; 6.8; 9.7; 12.7 mg/mL) and a concentration of physiological salt via the PBS buffer.

After addition of the solution of BSA in the PBS buffer, the mixture is rapidly homogenized by a few back and forth strokes of a pipette. One hour after the mixing, an absorbance measurement at 500 nm is carried out by means of a JASCO V-530 UV-Vis spectrophotometer.

The absorbance measurement at 500 nm makes it possible to evaluate the turbidity of the mixture originating from the precipitation of the insulin glargine. The turbidity increases as a function of the albumin concentration to reach a plateau reflecting the complete precipitation of the insulin glargine.

The critical albumin concentration allowing a quantitative precipitation is defined as the albumin concentration for which the absorbance value at 500 nm reaches 80% of the absorbance measured at the plateau.

One notes that in the compositions of the invention, the critical BSA quantity is lower.

The results are reported in the following Table 13:

TABLE 13

Critical albumin concentration (mg/mL) for 80% of precipitation at 1 h (insulin glargine at 50 U/mL).

| Co-polyamino acid | Critical albumin concentration (mg/ml) for 80% precipitation at 1 h (insulin glargine at 50 U/mL) | Concentration of co-polyamino acid in solution insulin glargine at 50 U/mL |
|---|---|---|
| CEB2 | ≥3.9 | 1.5 |
| CEB3 | ≥3.9 | 1.8 |
| CEB4 | ≥3.9 | 1.5 |
| BB7 | <3.9 | 1.8 |
| BB5 | <3.9 | 2.2 |
| BB14 | <3.9 | 2.5 |
| BB10 | <3.9 | 1.5 |
| BB15 | <3.9 | 2.0 |
| BB11 | <3.9 | 1.5 |
| BB16 | <3.9 | 1.5 |
| AB6 | <3.9 | 1.8 |
| AB21 | <3.9 | 1.5 |
| AB17 | <3.9 | 1.5 |
| AB18 | <3.9 | 1.5 |
| BB42 | <3.9 | 1.2 |
| BB18 | <3.9 | 1.5 |
| BB17 | <3.9 | 1.75 |
| BB25 | <3.9 | 1.1 |
| BB43 | <3.9 | 2 |
| BB20 | <3.9 | 1.25 |
| BB21 | <3.9 | 1.25 |

IV. Study of the Stability of the Compositions According to the Invention

Part E: Demonstration of the Physical Stability of the Compositions According to the Invention by the Study of Co-Polyamino Acid/Insulin Glargine 200 U/mL Compositions and of Co-Polyamino Acid/Insulin Glargine 200 U/mL/Lispro 66 U/mL Compositions.

Example E1: Stability Accelerated at 25° C. Under Dynamic Conditions 3 3-mL vials filled with 1 mL of composition co-polyamino acid/insulin glargine are placed vertically in an orbital stirrer. The stirrer is placed in an oven at 25° C., and the vials are subjected to stirring at 250 rpm. The vials are inspected visually daily/weekly in order to detect the appearance of visible particles or turbidity. This inspection is carried out according to the recommendations of the European Pharmacopoeia (EP 2.9.20): the vials are subjected to illumination of at least 2000 lux and are observed on a white background and on a black background. The number of days of stability corresponds to the duration after which at least 2 vials present visible particles or are turbid.

These results are in agreement with the US Pharmacopoeia (USP <790>).

The results of accelerated stability (obtained with different compositions) are presented in Table 14 below.

TABLE 14 results of the stabilities of the compositions of co-polyamino acid/insulin glargine (200 U/mL)/insulin lispro (66 U/mL) at 25° C. under dynamic conditions (with stirring at 250 rpm) and counter-examples.

| Composition | Co-polyamino acid | Stability at 25° C. under dynamic conditions (in days) |
|---|---|---|
| CB3 | — | * |
| CB3a | AB6 | 13 |
| CB3c | AB21 | 14 |
| CB3r | AB17 | 8 |
| CB3i | AB18 | 8 |
| CB3f | BB3 | 35 |
| CB3g | BB5 | >41 |
| CB3j | BB7 | 29 |
| CB3m | BB10 | 15 |
| CB3n | BB11 | 17 |
| CB3o | BB15 | 14 |
| CB3p | BB16 | 8 |
| CB3s | CEB2 | 5 |
| CB3t | CEB3 | 4 |
| CB3u | BB42 | 8 |
| CB3v | BB18 | 69 |
| CB3w | BB17 | 29 |
| CB3x | BB25 | 10 |
| CB3y | BB26 | >46 ongoing |
| CB3z | BB43 | 5-7 |
| CB3ac | BB20 | 32 |
| CB3ad | BB21 | 30 |
| CB3ae | CEBX3 | 2 |
| CB3af | CEBX4 | 2 |

(* Appearance of a precipitate when the pH of the solution is adjusted to pH 7).

The accelerated stability results obtained with the compositions of the table of Example CB12 are presented in Table 15 below.

TABLE 15 results of the stabilities of a composition of co-polyamino acid/insulin glargine (200 U/mL)/human insulin (66 U/mL) at 25° C. under dynamic conditions (with stirring at 250 rpm) and counter-example.

| Composition | Co-polyamino acid | Stability at 25° C. under dynamic conditions (in days) |
|---|---|---|
| CB12a | BB15 | >28 |
| CB12b | CEB2 | 7 |

The accelerated stability results obtained with the compositions of the table of Example DB5 are presented in Table 16 below.

TABLE 16

Results of the stabilities of the compositions of co-polyamino acid/insulin glargine (200 U/mL)/dulaglutide (1 mg/mL) at 25° C. under dynamic conditions (with stirring at 250 rpm).

| Composition | Glargine (U/mL) | Dulaglutide (mg/mL) | Co-polyamino acid | Concentration of co-polyamino acid (mg/mL) | Dynamic stability at 25° C. 250 rpm In days |
|---|---|---|---|---|---|
| DB3h | 200 | 1 | BB10 | 6 | 25 |
| DB3i | 200 | 1 | BB15 | 6 | >32 |
| DB3x | 200 | 1 | CEB3 | 7 | 7 |
| DB3z | 200 | 1 | CEB2 | 6 | 10 |
| C4 | 100 | — | — | — | >32 |
| D1 | — | 3 | — | — | >32 |

Demonstration of the Physical Stability of the Compositions According to the Invention by the Study of Compositions of Co-Polyamino Acid/Insulin Glargine/Insulin Lispro/Exenatide

Example E1': Accelerated Stability at 25° C. Under Dynamic Conditions 3 3-mL vials filled with 1 mL of the compositions of Table 8 are placed vertically in an orbital stirrer. The stirrer is placed in an oven at 25° C., and the vials are subjected to stirring at 250 rpm. The vials are inspected visually weekly in order to detect the appearance of visible particles or turbidity. This inspection is carried out according to the recommendations of the European Pharmacopoeia (EP 2.9.20): the vials are subjected to illumination of at least 2000 lux and are observed on a white background and on a black background. The number of weeks of stability corresponds to the duration after which at least 2 vials present visible particles or are turbid.

These results are in agreement with the US pharmacopoeia (USP <790>).

The accelerated stability results obtained with the compositions of Table 8 are presented in Table 17 below.

TABLE 17

Results of the stabilities of the compositions of co-polyamino acid/insulin glargine (200 U/mL)/insulin lispro (67 IU/mL) with or without exenatide at 25° C. under dynamic conditions (with stirring at 250 rpm).

| Composition | Co-polyamino acid | Stability at 25° C. under dynamic conditions (in weeks) |
|---|---|---|
| CB2a | BB15 | >9 |
| CB2b | BB15 | >9 |
| CB2c | BB15 | >9 |

Example E2: Accelerated Stability at 30° C. Under Static Conditions 5 3-mL vials filled with 1 mL of composition are placed vertically in an oven maintained at 30° C. The vials are inspected visually daily in order to detect the appearance of visible particles or turbidity. This inspection is carried out according to the recommendations of the European Pharmacopoeia (EP 2.9.20): the vials are subjected to illumination of at least 2000 lux and are observed on a white background and on a black background. The number of weeks of stability corresponds to the duration after which at least 2 vials present visible particles or are turbid.

These results are in agreement with the US pharmacopoeia (USP <790>).

The accelerated stability results (obtained with different compositions) are presented in Tables 18a and 18b below.

TABLE 18a

Results of the stabilities of the compositions of co-polyamino acid/insulin glargine (225 U/mL)/insulin lispro (75 IU/mL) at 30° C. under static conditions.

| Composition | Co-polyamino acid | Stability at 30° C. under static conditions (in week) |
|---|---|---|
| CB5 | — | * |
| CB5f | BB14 | >9 |

(* Appearance of a precipitate when the pH of the solution is adjusted to pH 7).

TABLE 18b

Results of the stabilities of the compositions of co-polyamino acid/insulin glargine (200 U/mL)/insulin lispro (66 IU/mL) at 30° C. under static conditions.

| Composition | Co-polyamino acid | Stability at 30° C. under static conditions (in week) |
|---|---|---|
| CB3 | — | * |
| CB3j | BB7 | >12 |
| CB3o | BB15 | >9 |

(* Appearance of a precipitate when the pH of the solution is adjusted to pH 7).

V. Examples of Compositions According to the Invention

Example H4: Preparation of Compositions of Co-Polyamino Acid, of Insulin Glargine at 200 U/mL and of Insulin Lispro at 66 U/mL at pH 7.1

Examples of the compositions of insulin glargine at 200 U/mL, of insulin lispro at 66 U/mL and of co-polyamino acids are described in Example CB3 and presented in Table 4a.

Example H5: Preparation of Compositions of Co-Polyamino Acid, of Insulin Glargine at 150 U/mL, of Insulin Lispro at 50 U/mL at pH 7.1

In a manner similar to Example H4, compositions of insulin glargine at 150 U/mL, of insulin lispro at 50 U/mL and of co-polyamino acid are prepared. They are presented in Table 19:

TABLE 19

Compositions of co-polyamino acid/insulin glargine (150 U/mL)/insulin lispro (50 U/mL).

| Composition | Insulin glargine (U/mL) | Insulin lispro (U/mL) | Co-polyamino acid | Concentration of co-polyamino acid (mg/mL) |
|---|---|---|---|---|
| H5a | 150 | 50 | AB6 | 5.25 |
| H5c | 150 | 50 | AB21 | 4.5 |
| H5f | 150 | 50 | BB3 | 5.25 |
| H5g | 150 | 50 | BB5 | 6.75 |
| H5i | 150 | 50 | AB18 | 4.5 |
| H5j | 150 | 50 | BB7 | 5.25 |
| H5m | 150 | 50 | BB10 | 4.5 |
| H5n | 150 | 50 | BB11 | 4.5 |
| H5o | 150 | 50 | BB15 | 4.5 |
| H5p | 150 | 50 | BB16 | 4.5 |
| H5r | 150 | 50 | AB17 | 4.5 |

Example H6: Preparation of Compositions of Co-Polyamino Acid and of Insulin Glargine at 300 U/mL, of Insulin Lispro at 100 U/mL and at pH 7.1

In a manner similar to Example H4, compositions of insulin glargine at 300 U/mL, of insulin lispro at 100 U/mL and of co-polyamino acid are prepared. They are presented in Table 20.

TABLE 20

Co-polyamino acid/insulin glargine (300 U/mL)/insulin lispro (100 U/mL) compositions.

| Composition | Insulin glargine (U/mL) | Insulin lispro (U/mL) | Co-polyamino acid | Concentration of co-polyamino acid (mg/mL) |
|---|---|---|---|---|
| H6a | 300 | 100 | AB6 | 30.5 |
| H6c | 300 | 100 | AB21 | 9 |
| H65f | 300 | 100 | BB3 | 10.5 |
| H6g | 300 | 100 | BB5 | 13.5 |
| H6i | 300 | 100 | AB18 | 9 |
| H6j | 300 | 100 | BB7 | 10.5 |
| H6m | 300 | 100 | BB10 | 9 |
| H6n | 300 | 100 | BB11 | 9 |
| H6o | 300 | 100 | BB15 | 9 |
| H6p | 300 | 100 | BB16 | 9 |
| H6r | 300 | 100 | AB17 | 9 |
| H6s | 300 | 100 | CEB2 | 9 |
| H6t | 300 | 100 | CEB3 | 10.5 |

Example H7: Preparation of Compositions of Co-Polyamino Acid and of Dulaglutide at 1 mg/mL at pH 7.1

In a manner similar to Example DB3, compositions of insulin glargine at 200 U/mL, of dulaglutide at 1 mg/mL and of co-polyamino acid are prepared. They are presented in Table 21.

TABLE 21

Compositions of co-polyamino acid and of dulaglutide at 1 mg/mL at pH 7.1

| Composition | Co-polyamino acid | Insulin glargine (U/mL) | Dulaglutide (mg/mL) | Co-polyamino acid (mg/mL) |
|---|---|---|---|---|
| DB1 | — | 50 | 0.25 | — |
| DB2 | — | 50 | 0.25 | — |
| DB3a | AB6 | 200 | 1 | 7 |
| DB3b | AB17 | 200 | 1 | 6 |
| DB3c | BB7 | 200 | 1 | 7 |
| DB3d | BB5 | 200 | 1 | 9 |
| DB3e | BB10 | 200 | 1 | 6 |
| DB3f | BB14 | 200 | 1 | 9 |
| DB3g | BB15 | 200 | 1 | 6 |

Example H8: Preparation of Compositions of Co-Polyamino Acid, of Insulin Glargine at 150 U/mL, and of Dulaglutide at 0.75 mg/mL at pH 7.1

In a manner similar to Example H7, compositions of insulin glargine at 150 U/mL, of dulaglutide at 0.75 mg/mL and of co-polyamino acid are prepared. They are presented in Table 22

TABLE 22

Co-polyamino acid/insulin glargine (150 U/mL)/dulaglutide (0.75 mg/mL) compositions.

| Composition | Co-polyamino acid | Insulin glargine (U/mL) | Dulaglutide (mg/mL) | Co-polyamino acid (mg/mL) |
|---|---|---|---|---|
| H8a | AB6 | 150 | 0.75 | 5.25 |
| H8b | AB17 | 150 | 0.75 | 4.5 |
| H8c | BB7 | 150 | 0.75 | 5.25 |
| H8d | BB5 | 150 | 0.75 | 6.75 |
| H8e | BB10 | 150 | 0.75 | 4.5 |
| H8f | BB14 | 150 | 0.75 | 6.75 |
| H8g | BB15 | 150 | 0.75 | 4.5 |

Example H9: Preparation of Compositions of Co-Polyamino Acid, of Insulin Glargine at 300 U/mL, and of Dulaglutide at 1.5 mg/mL at pH 7.1

In a manner similar to Example H7, compositions of insulin glargine at 300 U/mL, of dulaglutide at 1.5 mg/mL and of co-polyamino acid are prepared. They are presented in Table 23.

TABLE 23

Compositions of co-polyamino acid/insulin glargine (300 U/mL)/dulaglutide (1.5 mg/mL).

| Composition | Co-polyamino acid | Insulin glargine (U/mL) | Dulaglutide (mg/mL) | Co-polyamino acid (mg/mL) |
|---|---|---|---|---|
| H8a | AB6 | 300 | 1.5 | 10.5 |
| H8b | AB17 | 300 | 1.5 | 9 |
| H8c | BB7 | 300 | 3.5 | 10.5 |
| H8d | BB5 | 300 | 1.5 | 13.5 |
| H8e | BB10 | 300 | 1.5 | 9 |
| H8f | BB14 | 300 | 1.5 | 13.5 |
| H8g | BB15 | 300 | 1.5 | 9 |

Part F: Pharmacokinetic and Pharmacodynamic Studies in Dogs

Example F1: Pharmacokinetic and Pharmacodynamic Study in Dogs of the Co-Polyamino Acid BB7 (7 mg/mL)/Insulin Glargine (200 U/mL)/Insulin Lispro (66 U/mL) Composition Studies in dogs were carried out for the purpose of evaluating the pharmacokinetics and the pharmacodynamics of an insulin solution composition.

The pharmacokinetic profiles and the hypoglycemic effects of this composition were compared to those of simultaneous but separate injections of insulin glargine (Lantus®) (pH 4) (Example C4) and a prandial insulin lispro (Humalog®) (Example C1) in the proportions of 75% of insulin glargine (Lantus®)/25% of insulin lispro (Humalog®).

Ten animals that had fasted for approximately 18 hours received injections in the neck above the interscapular region at the dose of 0.8 U/kg using a Junior Star pen. In the hour preceding the insulin injection(s), 2 blood samples are drawn in order to determine the basal glucose and insulin levels. Blood samples are then drawn during the 20 h following the injection(s). The glycemia is determined by means of a glucometer. The insulin levels are determined by an ELISA test.

The mean pharmacokinetic curves of insulin expressed in deviation from the basal level are presented in FIG. 1.

The mean pharmacodynamic curves of glucose expressed in percentage of the basal level are represented in FIG. 2.

The pharmacokinetic results obtained with the separate and simultaneous administrations of insulin lispro (Humalog®) and insulin glargine (Lantus®) in comparison to those obtained with the composition described in Example CB3j are presented in FIG. 1. The profiles are biphasic. The first phase corresponds to an insulin peak which appears very rapidly after the injection, in the 30 minutes after the injection. The peak extends up to approximately 3 h after the administration. The second phase is observed, it starts approximately 3 h after the administration and ends at the end of the profile and corresponds to a prolonged absorption of insulin leading to a flat profile. This second phase is the basal portion of the insulin profile while the first phase corresponds to the prandial portion thereof. These two phases are characteristic of a simultaneous injection of prandial insulin and basal insulin, and they are indeed reproduced with the composition of the invention presented in Example CB3j.

The pharmacodynamic results obtained with the separate and simultaneous administrations of insulin lispro (Humalog®) and insulin glargine (Lantus®) in comparison to those obtained with the composition described in Example CB3j are presented in FIG. 2. The hypoglycemic activity of the composition described in Example CB3j is biphasic. The first rapid phase is defined by a pronounced decrease of glycemia for approximately 60 minutes, which is characteristic of the rapid effect of insulin lispro. This first phase is also visible with the double Lantus®/Humalog® injection, indicating that the composition according to the invention does not modify the rapid character of Humalog®. After approximately 60 minutes, the glycemia rises up to 3 hours, before a second slower phase characterized by a less pronounced hypoglycemic activity lasting up to 18-20 hours post injection. This basal second phase is characteristic of the basal effect of insulin glargine, also visible with the double injection, indicating that the effect is indeed maintained with the composition according to the invention described in Example CB3j.

Example F2: The Pharmacokinetic and Pharmacodynamic Study in Dogs of the Co-Polyamino Acid BB15 (6 mg/mL)/Insulin Glargine (200 U/mL)/Insulin Lispro (66 U/mL) Composition The pharmacokinetic profiles and the hypoglycemic effects of this composition were compared with those of simultaneous but separate injections of insulin glargine (Lantus) (pH 4) (Example C4) and a prandial insulin lispro (Humalog®) (Example C1) in the proportions of 75% of insulin glargine (Lantus®)/25% of insulin lispro (Humalog®).

Ten animals that had fasted for approximately 18 hours received injections in the neck above the interscapular region at the dose of 0.8 U/kg using a Junior Star pen. In the hour preceding the injection(s) of insulin, 2 blood samples are drawn in order to determine the basal glucose and insulin levels. Blood samples are then drawn during the 20 h following the injection(s). The glycemia is determined by means of a glucometer. The insulin levels are determined by an ELISA test.

The mean pharmacokinetic curves of insulin, expressed in deviation from the basal level, are presented in FIG. 3.

The mean pharmacodynamic curves of glucose, expressed in percentage of the basal level, are represented in FIG. 4.

The pharmacokinetic results obtained with the simultaneous administrations of insulin lispro (Humalog) and insulin glargine (Lantus®) in comparison with the composition described in Example CB3o are presented in FIG. 3. The profiles are biphasic. The first phase corresponds to an insulin peak which appears very rapidly after the injection, in the 30 minutes after the injection. The peak extends up to approximately 3 h after the administration. The second phase is observed, it starts approximately 3 h after the administration and ends at the end of the profile and corresponds to a prolonged absorption of insulin leading to a flat profile. This second phase is the basal portion of the insulin profile while the first phase corresponds to the prandial phase thereof. These two phases are characteristic of a simultaneous injection of prandial insulin and basal insulin, and they are indeed reproduced with the composition of the invention presented in Example CB3o.

The pharmacodynamic results obtained with the separate and simultaneous administrations of insulin lispro (Humalog®) and insulin glargine (Lantus®) in comparison to those obtained with the composition described in Example CB3o are presented in FIG. 4. The hypoglycemic activity of the composition described in Example CB3o is biphasic. The first rapid phase is defined by a pronounced decrease of glycemia for approximately 60 minutes, which is characteristic of the rapid effect of insulin lispro. This first phase is also visible with the double insulin glargine (Lantus®)/insulin lispro (Humalog®) injection, indicating that the composition according to the invention does not modify the rapid character of the insulin lispro (Humalog®). After approximately 60 minutes, the glycemia rises up to 3 hours, before a second slower phase characterized by a less pronounced hypoglycemic activity which lasts up to 18-20 hours post injection. This second basal phase is characteristic of the basal effect of insulin glargine, also visible with the double injection, indicating that the effect is indeed maintained with the composition according to the invention described in Example CB3o.

Example F3: Pharmacokinetic and Pharmacodynamic Study in Dogs of the Co-Polyamino Acid BB15 (5 mg/mL)/Insulin Glargine (200 U/mL)/Insulin Lispro (66 U/mL)/Exenatide Composition Studies in dogs were carried out for the purpose of evaluating the pharmacokinetics and the pharmacodynamics of the insulin and after administration of compositions of co-polyamino acid and insulins (composition CB2a) and of co-polyamino acid, insulins and exenatide (composition CB2c).

The hypoglycemic effects and the pharmacokinetic profiles of the insulins of the composition CB2c were compared with those of the composition CB2a of identical composition but without exenatide.

Ten animals that had fasted for approximately 18 hours received injections in the neck above the interscapular region, at the dose of 0.67 U/kg of insulin for composition CB2a, and of 0.67 U/kg of insulin and 0.125 µg/kg of exenatide for composition CB2c. Under these conditions of administration widely spaced from the meal the pharmacodynamic effect can be attributed to the insulins alone. In the hour preceding the injection, a blood sample is drawn in order to determine the basal insulin level, and 3 samples are collected in order to determine the basal glucose level. Blood samples are then drawn during the 23 h after the administration in order to describe the pharmacokinetics of the insulins. The glycemia is determined for 24 h by means of a glucometer. The insulin levels are determined by an ELISA test.

The mean pharmacokinetic curves of the insulin, expressed in deviation from the basal level, are presented in FIG. 5.

The mean pharmacodynamic curves of the glucose, expressed in percentage of deviation of the basal level, are represented in FIG. 6.

The insulin pharmacokinetic results obtained after the administration of the composition without exenatide (composition CB2a) in comparison to those of the composition with exenatide (composition CB2c) are presented in FIG. 5. The profiles are biphasic. The first phase corresponds to an insulin peak which appears very rapidly after injection, in the 30 to 45 minutes after the injection. The peak extends up to approximately 3 h after the administration. The second phase is observed approximately 3 h after the administration until the end of the profile and corresponds to a prolonged absorption of insulin leading to a flat profile. This second phase is the basal portion of the insulin profile while the first part corresponds to the prandial portion thereof. These two phases are characteristic of separate and simultaneous injections of prandial insulin and basal insulin. The profiles are similar for the two compositions, which demonstrates that the presence of exenatide does not modify the kinetics of the insulins of composition CB2c.

The pharmacodynamic results obtained with the administration of the compositions CB2a and composition CB2c are presented in FIG. 6. The hypoglycemic activity of the compositions is biphasic. The first rapid phase is defined by a pronounced decrease of glycemia for approximately 60 minutes, which is characteristic of the rapid effect of insulin lispro. After approximately 60 minutes, the glycemia rises up to 3 hours, before a second slower phase which is characterized by a less pronounced hypoglycemic activity which lasts up to 18-24 hours post injection. This second basal phase is characteristic of the basal effect of insulin glargine. The profile is similar for the two compositions (CB2a and CB2c), indicating that the presence of exenatide does not modify the bioactivity of the composition CB2c.

Example F4: Pharmacodynamic Study in Dogs of the Composition of Co-Polyamino Acid BB15 (5 Mg/mL)/Insulin Glargine (200 U/mL)/Insulin Lispro (66 U/mL)/Exenatide Studies in dogs were carried out for the purpose of evaluating the pharmacodynamics of a liquid co-formulation of insulins and exenatide (composition CB2c).

The hypoglycemic effects of composition CB2c were compared to those of separate and simultaneous injections of insulin glargine (Lantus®) (pH 4), insulin lispro (Humalog®) in the presence of exenatide (Byetta®).

Ten animals that had fasted for 3 hours received injections in the neck above the interscapular region at the dose of 1 U/kg of insulin and 0.19 µg/kg of exenatide. Under these conditions of administration immediately after a meal, the pharmacodynamic effect can be attributed to the insulins and to exenatide. In the hour preceding the injection, 3 blood samples were collected in order to determine the basal glucose level. Blood samples are then collected during the 6 h after the administration. The glycemia is determined by means of a glucometer.

The mean pharmacodynamic curves of glucose, expressed as in percentage of deviation from the basal level, are represented in FIG. 7.

The pharmacodynamic results obtained after the administration of composition CB2c in comparison to those obtained after the separate and simultaneous administrations of insulin lispro (Humalog®), insulin glargine (Lantus®) and exenatide (Byetta®) (referred to as triple injection) are presented in FIG. 7. The hypoglycemic activity of composition CB2c is biphasic. The first rapid phase is defined by a pronounced decrease of glycemia for approximately 60 minutes, which is characteristic of the rapid effect of exenatide and of insulin lispro (Humalog®), as one can see in the profile of the triple injection. After approximately 60 minutes, the glycemia rises up to 3 hours, before a second slower phase characterized by a less pronounced hypoglycemic activity up to 6 hours post injection. This second basal phase is characteristic of the basal effect of the insulin glargine, and is observed similarly on the profile of the triple injection and of composition CB2c. These results show that the effects of exenatide and of insulins are indeed maintained with composition CB2c.

The invention claimed is:

1. A composition in the form of an injectable aqueous solution, the pH of which is from 6.0 to 8.0, comprising at least:

a) one basal insulin the isoelectric point (pI) of which is from 5.8 to 8.5, and b) a prandial insulin and/or a gastrointestinal hormone, and c) a co-polyamino acid consisting of glutamic or aspartic units bearing carboxylate charges and hydrophobic radicals Hy, and said hydrophobic radicals Hy being radicals of the following formula I:

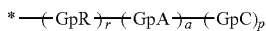

Formula I in which

GpR is a radical of formula II or II':

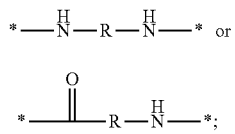

GpA is a radical of formula III or III':

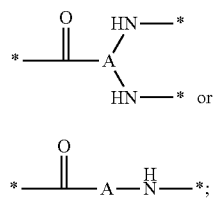

GpC is a radical of formula IV:

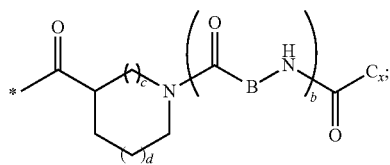

IV

Hy comprises more than 30 carbon atoms,
the * indicate the sites of attachment of the different groups bound by amide functions;
a is a whole number equal to 0 or 1;
b is a whole number equal to 0 or 1;
p is a whole number equal to 1 or 2, and
if p is equal to 1, then a is equal to 0 or 1 and GpA is a radical of formula III', and
if p is equal to 2, then a is equal to 1 and GpA is a radical of formula III;
c is a whole number equal to 0 or 1, and, if c is equal to 0, then d is equal to 1 or 2;
d is a whole number equal to 0, to 1 or 2;
r is a whole number equal to 0 or 1, and
if r is equal to 0, then the hydrophobic radical of formula I is bound to the co-polyamino acid via a covalent bond between a carbonyl of the hydrophobic radical and a nitrogen atom in N-terminal position of the co-polyamino acid, thus forming an amide function, and if r is equal to 1, then the hydrophobic radical of formula I is bound to the co-polyamino acid:
via a covalent bond between a nitrogen atom of the hydrophobic radical and a carbonyl of the co-polyamino acid, thus forming an amide function, or
via a covalent bond between a carbonyl of the hydrophobic radical and a nitrogen atom in N-terminal position of the co-polyamino acid, thus forming an amide function;
R is a radical selected from the group consisting of:
a linear or branched divalent alkyl radical comprising, if GpR is a radical of formula II, from 2 to 12 carbon atoms, or, if GpR is a radical of formula II', from 1 to 11 carbon atoms;
a linear or branched divalent alkyl radical comprising, if GpR is a radical of formula II, from 2 to 11 carbon atoms, or, if GpR is a radical of formula II', from 1 to 11 carbon atoms, said alkyl radical bearing one or more —CONH2 functions, and
an un-substituted ether or polyether radical comprising from 4 to 14 carbon atoms and from 1 to 5 oxygen atoms;
A is a linear or branched alkyl radical comprising from 1 to 6 carbon atoms;
B is a linear or branched alkyl radical, optionally comprising an aromatic ring, comprising from 1 to 9 carbon atoms;
$C_x$ is a linear or branched monovalent alkyl radical, in which x indicates the number of carbon atoms, and:
if p is equal to 1, x is from 11 to 25 ($11 \leq x \leq 25$);
if p is equal to 2, x is from 9 to 15 ($9 \leq x \leq 15$),
the ratio i between the number of hydrophobic radicals and the number of glutamic or aspartic units being between $0 < i \leq 0.5$;
when several hydrophobic radicals are borne by a co-polyamino acid, then they are identical or different,
the degree of polymerization DP in glutamic or aspartic units is from 5 to 250;
the free acid functions being in the form of a salt of an alkaline cation selected from the group consisting of $Na^+$ and $K^+$.

2. The composition according to claim 1, wherein said hydrophobic radicals are selected from the hydrophobic radicals of formula I in which p=1, represented by the following formula V:

formula V

GpR, GpA, GpC, r and a have the definitions given above.

3. The composition according to claim 1, wherein said hydrophobic radicals are selected from the hydrophobic radicals of formula I in which a=1 and p=2, represented by the following formula VI:

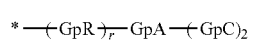

Formula VI in which

GpR, GpA, GpC, r and a have the definitions given above.

4. The composition according to claim 1, wherein the co-polyamino acid bearing carboxylate charges and hydrophobic radicals is selected from the co-polyamino acids of the following formula VII:

formula VII

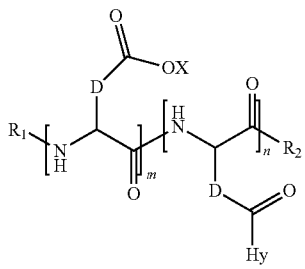

in which,

D represents, independently, either a —CH$_2$— group (aspartic unit) or a —CH$_2$—CH$_2$— group (glutamic unit), Hy is a hydrophobic radical selected from the hydrophobic radicals of formula I, V or VI, in which r=1 and GpR is a radical of Formula II, R$_1$ is a hydrophobic radical selected from the hydrophobic radicals of formula I, V or VI in which r=0 or r=1 and GpR is a radical of Formula II', or a radical selected from the group consisting of H, a C2 to C10 linear acyl group, a C4 to C10 branched acyl group, benzyl, a terminal "amino acid" unit and a pyroglutamate, R$_2$ is a hydrophobic radical selected from the hydrophobic radicals of formula I, V or VI in which r=1 and GpR is a radical of Formula II, an —NR'R" radical, R' and R" which are identical or different being selected from the group consisting of H, the C2 to C10 linear or branched or cyclic alkyls, benzyl, and said alkyl R' and R" together optionally forming one or more saturated, unsaturated and/or aromatic carbon rings and/or optionally comprising heteroatoms selected from the group consisting of O, N and S;

X represents a cationic entity selected from the group comprising the alkaline cations;

n+m represents the degree of polymerization DP of the co-polyamino acid, that is to say the average number of monomer units per co-polyamino acid chain, and 5≤n+m≤250.

5. The composition according to claim 4, wherein co-polyamino acid bearing carboxylate charges and hydrophobic charges is selected from the co-polyamino acids of formula VII, in which R$_1$=R'$_1$ and R$_2$=R'$_2$, of the following formula VIIa:

Formula VIIa

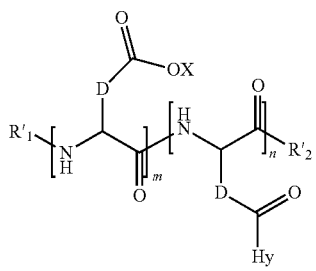

in which m, n, X, D and Hy have the definitions given above,

R'$_1$ is a radical selected from the group consisting of H, a C2 to C10 linear acyl group, a C4 to C10 branched acyl group, benzyl, a terminal "amino acid" unit and a pyroglutamate, R'$_2$ is a —NR'R" radical, R' and R" which are identical or different being selected from the group consisting of H, the C2 to C10 linear or branched or cyclic alkyls, benzyl, and said alkyl R' and R" together optionally forming one or more saturated, unsaturated and/or aromatic carbon rings and/or optionally comprising heteroatoms selected from the group consisting of O, N and S.

6. The composition according to claim 4, wherein the co-polyamino acid bearing carboxylate charges and hydrophobic radicals is selected from the co-polyamino acids of formula VII, in which n=0, of the following formula VIIb:

Formula VIIb

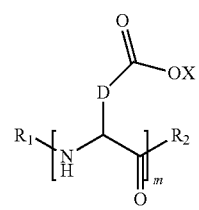

in which m, X, D, R$_1$ and R$_2$ have the definitions given above, and at least one R$_1$ or R$_2$ is a hydrophobic radical of formula I, V or VI.

7. The composition according to claim 6, wherein the co-polyamino acid bearing carboxylate charges and hydrophobic radicals is selected from the co-polyamino acids of formula VII, in which n=0, of formula VIIb, and R$_1$ or R$_2$ is a hydrophobic radical of formula I, V or VI.

8. The composition according to claim 6, wherein the co-polyamino acid bearing carboxylate charges and hydrophobic radicals is selected from the co-polyamino acids of formula VIIb, in which R$_2$ is a hydrophobic radical of formula I, V or VI, in which r=1 and GpR is of formula II.

9. The composition according to claim 4, wherein R$_1$ is a radical selected from the group consisting of a C$_2$ to C$_{10}$ linear acyl group, a C$_4$ to C$_{10}$ branched acyl group, benzyl, a terminal "amino acid" unit and a pyroglutamate.

10. The composition according to claim 9, wherein R$_1$ is a radical selected from the group consisting of a C$_2$ to C$_{10}$ linear acyl group or a C$_4$ to C$_{10}$ branched acyl group.

11. The composition according to claim 4, wherein the co-polyamino acid bearing carboxylate charges and hydrophobic radicals is selected from the co-polyamino acids of formula VII, VIIa or VIIb, in which the co-polyamino acid is selected from the co-polyamino acids in which group D is a —CH$_2$— group (aspartic unit).

12. The composition according to claim 4, wherein the co-polyamino acid bearing carboxylate charges and hydrophobic radicals is selected from the co-polyamino acids of formula VII, VIIa or VIIb, in which the co-polyamino acid is selected from the co-polyamino acids in which group D is a —CH$_2$—CH$_2$— group (glutamic unit).

13. The composition according to claim 1, wherein the basal insulin of which the isoelectric point is from 5.8 to 8.5 is insulin glargine.

14. The composition according to claim 1, wherein it comprises from 40 to 500 U/mL of basal insulin of which the isoelectric point is from 5.8 to 8.5.

15. The composition according to claim 1, wherein the concentration of co-polyamino acid bearing carboxylate charges and hydrophobic radicals is at most 60 mg/mL.

16. The composition according to claim 1, wherein the concentration of co-polyamino acid bearing carboxylate charges and hydrophobic radicals is at most 40 mg/mL.

17. The composition according to claim 1, wherein the concentration of co-polyamino acid bearing carboxylate charges and hydrophobic radicals is at most 20 mg/mL.

18. The composition according to claim 1, wherein the concentration of co-polyamino acid bearing carboxylate charges and hydrophobic radicals is at most 10 mg/mL.

19. The composition according to claim 1, comprising at least
    a) one basal insulin the isoelectric point (pI) of which is from 5.8 to 8.5,
    b) a prandial insulin, and
    c) a co-polyamino acid bearing carboxylate charges and at least one hydrophobic radical of the formula I.

20. The composition according to claim 19, wherein the prandial insulin is human insulin.

21. The composition according to claim 19, wherein it comprises in total from 40 to 500 U/mL of insulin with a combination of prandial insulin and of basal insulin of which the isoelectric point is from 5.8 to 8.5.

22. The composition according to claim 19, wherein the proportions between the basal insulin of which the isoelectric point is from 5.8 to 8.5 and the prandial insulin are, expressed in percentage, 25/75, 30/70, 40/60, 50/50, 60/40, 70/30, 80/20 or 90/10.

23. The composition according to claim 1, comprising at least:
    a) one basal insulin the isoelectric point (pI) of which is from 5.8 to 8.5,
    b) a gastrointestinal hormone, and
    c) a co-polyamino acid bearing carboxylate charges and at least one hydrophobic radical of the formula I.

24. The composition according to claim 1, comprising at least:
    a) one basal insulin the isoelectric point (pI) of which is from 5.8 to 8.5,
    b) a prandial insulin and a gastrointestinal hormone, and
    c) a co-polyamino acid bearing carboxylate charges and at least one hydrophobic radical of the formula I.

25. The composition according to claim 24, wherein the gastrointestinal hormone is selected from the group consisting of exenatide, liraglutide, lixisenatide, albiglutide and dulaglutide, the analogs or derivatives thereof, and the pharmaceutically acceptable salts thereof.

26. The composition according to claim 23, wherein the gastrointestinal hormone is dulaglutide, the analogs or derivatives thereof, and the pharmaceutically acceptable salts thereof.

27. The composition according to claim 23, wherein the gastrointestinal hormone is exenatide, the analogs or derivatives thereof, and the pharmaceutically acceptable salts thereof.

28. The composition according to claim 23, wherein the gastrointestinal hormone is liraglutide, the analogs or derivatives thereof, and the pharmaceutically acceptable salts thereof.

29. The composition according to claim 23, wherein the gastrointestinal hormone is lixisenatide, the analogs or derivatives thereof, and the pharmaceutically acceptable salts thereof.

30. The composition according to claim 23, wherein the concentration of gastrointestinal hormone is within an interval of 0.01 to 10 mg/mL.

31. The composition according to claim 24, wherein it comprises from 40 U/mL to 500 U/mL of basal insulin of which the isoelectric point is from 5.8 to 8.5, and from 0.05 to 0.5 mg/mL of exenatide.

32. The composition according to claim 24, wherein it comprises from 40 U/mL to 500 U/mL of basal insulin of which the isoelectric point is from 5.8 to 8.5, and from 1 to 10 mg/mL of liraglutide.

33. The composition according to claim 24, wherein it comprises from 40 U/mL to 500 U/mL of basal insulin of which the isoelectric point is from 5.8 to 8.5, and from 0.01 to 1 mg/mL of lixisenatide.

34. A single-dose formulation at a pH from 7 to 7.8, comprising a basal insulin of which the isoelectric point is from 5.8 to 8.5, and a prandial insulin.

35. A single-dose formulation at a pH from 7 to 7.8, comprising a basal insulin of which the isoelectric point is from 5.8 to 8.5, and a gastrointestinal hormone.

36. A single-dose formulation at a pH from 7 to 7.8, comprising a basal insulin of which the isoelectric point from 5.8 to 8.5, a prandial insulin, and a gastrointestinal hormone.

* * * * *